United States Patent
Link et al.

(10) Patent No.: US 7,547,701 B2
(45) Date of Patent: Jun. 16, 2009

(54) HALOALKYL CONTAINING COMPOUNDS AS CYSTEINE PROTEASE INHIBITORS

(75) Inventors: John O. Link, San Francisco, CA (US);
Craig J. Mossman, Campbell, CA (US);
Soon H. Woo, Palo Alto, CA (US);
Sheila M. Zipfel, Mountain View, CA (US)

(73) Assignee: Virobay, Inc., Menlo Park, CA (US)

( * ) Notice: Subject to any disclaimer, the term of this patent is extended or adjusted under 35 U.S.C. 154(b) by 589 days.

(21) Appl. No.: 10/943,768

(22) Filed: Sep. 17, 2004

(65) Prior Publication Data

US 2005/0182096 A1  Aug. 18, 2005

Related U.S. Application Data

(60) Provisional application No. 60/561,062, filed on Apr. 9, 2004, provisional application No. 60/504,680, filed on Sep. 18, 2003.

(51) Int. Cl.
*A61K 31/497* (2006.01)
*C07D 241/04* (2006.01)
*C07D 213/57* (2006.01)
*C07C 255/03* (2006.01)
*C07D 333/22* (2006.01)

(52) U.S. Cl. ............... 514/252.1; 514/357; 514/365; 514/396.1; 544/393; 544/400; 546/330; 548/204; 548/205; 558/404; 558/414; 558/431; 558/434

(58) Field of Classification Search ............... 514/252.1, 514/357, 365, 396, 521, 396.1; 544/393, 544/400; 546/330; 548/204, 205; 558/404, 558/414, 431, 434; 549/76, 77

See application file for complete search history.

(56) References Cited

U.S. PATENT DOCUMENTS

| | | | |
|---|---|---|---|
| 6,420,364 B1 | 7/2002 | Emmanuel et al. | |
| 6,730,671 B2 | 5/2004 | Cywin et al. | |
| 7,312,211 B2 | 12/2007 | Bekkali et al. | |
| 2004/0127426 A1 | 7/2004 | Graupe et al. | |
| 2005/0014941 A1 * | 1/2005 | Black et al. | 544/163 |
| 2005/0182096 A1 | 8/2005 | Link et al. | |
| 2005/0240023 A1 * | 10/2005 | Bayly et al. | 546/330 |
| 2006/0111440 A1 * | 5/2006 | Gauthier et al. | 514/519 |

FOREIGN PATENT DOCUMENTS

| | | |
|---|---|---|
| EP | 0 623 627 A1 | 11/1994 |
| WO | WO99/24460 | 5/1999 |
| WO | WO 99/24460 A3 | 5/1999 |
| WO | WO 00/51998 | 9/2000 |
| WO | WO 00/055125 A2 | 9/2000 |
| WO | WO00/55144 | 9/2000 |
| WO | WO01/19796 A1 | 3/2001 |
| WO | WO 01/19816 A1 | 3/2001 |
| WO | WO01/19816 A1 | 3/2001 |
| WO | WO 01/49288 A1 | 7/2001 |
| WO | WO01/68645 A2 | 9/2001 |
| WO | WO02/20485 A1 | 3/2002 |
| WO | WO 02/069901 A2 | 9/2002 |
| WO | WO02/098850 A2 | 12/2002 |
| WO | WO03/029200 A2 | 4/2003 |
| WO | WO03/075836 A2 | 9/2003 |
| WO | WO 03/097617 A1 | 11/2003 |
| WO | WO 2004/033445 A1 | 4/2004 |
| WO | WO2004/083182 A1 | 9/2004 |
| WO | WO 2004/108661 A1 | 12/2004 |
| WO | WO2005/021487 A1 | 3/2005 |
| WO | WO 2005/028429 A2 | 3/2005 |
| WO | WO 2005/028454 A1 | 3/2005 |
| WO | WO 2005/040124 A | 5/2005 |
| WO | WO 2005/058348 A1 | 6/2005 |
| WO | WO 2005/063742 A2 | 7/2005 |
| WO | WO 02/074904 A2 | 8/2005 |
| WO | WO 2005/074904 A2 | 8/2005 |
| WO | WO 2006/034004 A2 | 3/2006 |

OTHER PUBLICATIONS

Volonterio, et al., Solution/Solid-Phase Synthesis of Partially Modified Retro-ψ [NHCH(CF$_3$)]-Peptidyl Hydroxamates, Tetrahedron Letters, Feb. 23, 2001, pp. 3141-3144, vol. 42, Dipartimento di Chimica del Politecnico di Milano, Milan, Italy.

Greenspan, et al., Identification of Dipeptidyl Nitriles as Potent and Selective Inhibitors of Cathepsin B through Structure-Based Drug Design, J. Med. Chem., 2001, pp. 4524-4534, vol. 44, Amer. Chem Society, USA.

Bundgaard, et al. "A Novel Solution-Stable, Water-Soluble Prodrug Type for Drugs Containing a Hydroxyl or an NH-Acidic Group," J. Med. Chem., 19898, vol. 32, No. 12, pp. 2503-2507.

Gong, Y., et al., "Convenient Substitution of Hydroxypyridines with Trifluoroacetaldehyde Ethyl Hemiacetal," Journal of Heterocyclic Chemistry 2001, vol. 38, No. 1, p. 25-28.

* cited by examiner

*Primary Examiner*—James O. Wilson
*Assistant Examiner*—Ebenezer Sackey
(74) *Attorney, Agent, or Firm*—Townsend and Townsend and Crew LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

23 Claims, No Drawings

HALOALKYL CONTAINING COMPOUNDS AS CYSTEINE PROTEASE INHIBITORS

CROSS REFERENCE

This Application claims the right of priority under U.S.C. § 119(e) of U.S. Provisional Applications Nos. 60/504,680 and 60/561,062, filed on Sep. 18, 2003 and Apr. 9, 2004, respectively, the disclosures of which are incorporated herein by reference in their entirety.

FIELD OF THE INVENTION

The present invention is directed to compounds that are inhibitors of cysteine proteases, in particular, cathepsins B, K, L, F, and S and are therefore useful in treating diseases mediated by these proteases. The present invention is also directed to pharmaceutical compositions comprising these compounds and processes for preparing them.

STATE OF THE ART

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to asthma; and allogeneic immune reponses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of this class of enzymes, in particular molecules which inhibitor cathepsins B, K, L, F, and/or S, will therefore be useful as therapeutic agents.

SUMMARY OF THE INVENTION

In one aspect, this invention is directed to a compound of Formula (I):

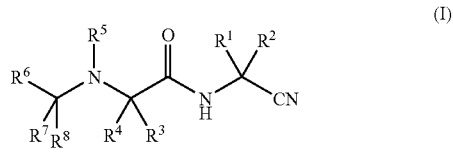

wherein:

$R^1$ is hydrogen, alkyl, haloalkyl, or alkoxyalkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl, (ii) a four atom heterocyclylalkylene ring, or (iii) heterocyclylalkylene optionally substituted with one to four $R^c$ independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, cycloalkyl, cycloalkylalkyl, aralkyl, aryloxycarbonyl, alkoxy, hydroxy, haloalkoxy, halo, carboxy, alkoxycarbonyl, amino, monsubstituted amino, disubstituted amino, or acyl;

$R^3$ is hydrogen or alkyl;

$R^4$ is 1-alkylcyclopentylmethyl, 1-alkylcyclopentylethyl, 1-alkylcyclohexylmethyl, 1-alkylcyclohexylethyl, aryl, aralkyl, heteroaryl, heteroaralkyl, heterocyclylalkyl, or -alkylene-$X^1$—$R^{22}$ (wherein $X^1$ is —$NR^{23}$—, —O—, —$S(O)_{n3}$—, —CO—, —COO—, —OCO—, —$NR^{23}CO$—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$—, or —NR$^{23}$SO$_2$NR$^{24}$— where R$^{23}$ and R$^{24}$ are independently hydrogen, alkyl, or acyl, n3 is 0-2, and R$^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl) wherein the alkylene chain in R$^4$ is optionally substituted with one to six halo and wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

R$^5$ is hydrogen or alkyl;

R$^6$ is hydrogen, alkyl, haloalkyl, cycloalkyl, aryl, aralkyl, heteroaryl, heteroaralkyl, heterocyclyl, or -alkylene-X$^2$—R$^{25}$ (where X$^2$ is —NR$^{26}$—, —O—, —S(O)$_{n4}$—, —CO—, —COO—, —OCO—, —NR$^{26}$CO—, —CONR$^{26}$—, —NR$^{26}$SO$_2$—, —SO$_2$NR$^{26}$—, —NR$^{26}$COO—, —OCONR$^{26}$—, —NR$^{26}$CONR$^{27}$—, or —NR$^{26}$SO$_2$NR$^{27}$— where R$^{26}$ and R$^{27}$ are independently hydrogen, alkyl, or acyl, n4 is 0-2, and R$^{25}$ is hydrogen, alkyl, haloalkyl, cycloalkyl, cycloalkylalkyl, heterocyclyl, heterocyclylalkyl, aryl, aralkyl, heteroaryl, or heteroaralkyl) wherein said alkylene chain in R$^6$ is optionally substituted with one to six halo and the aromatic or alicyclic rings in R$^6$ are optionally substituted by one, two, or three R$^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, aryl, aralkyl, aryloxy, aralkyloxy, arylsulfonyl, heteroaryl, heteroaralkyl, heteroaryloxy, heteroaralkyloxy, heteroarylsulfonyl, heterocyclyl, heterocyclylalkyl, cycloalkyl, cycloalkylalkyl, carboxy, alkoxycarbonyl, alkylsulfonyl, aminosulfonyl, or aminoalkyl and further where the aromatic or alicyclic ring in R$^e$ is optionally substituted with one, two or three R$^f$ independently selected from alkyl, alkoxy, haloalkyl, haloalkoxy, halo, hydroxy, carboxy, cyano, nitro, aryl or cycloalkyl;

R$^7$ is haloalkyl optionally substituted with alkoxy or alkoxyalkyloxy; and

R$^8$ is hydrogen, alkyl, alkoxyalkyl or haloalkyl; or

R$^6$ and R$^8$ together with the carbon atom to which they are attached form cycloalkylene or heterocyclylalkylene wherein said cycloalkylene is optionally substituted with one to four substituents independently selected from alkyl, halo, haloalkyl, hydroxy, or alkoxy and heterocyclylalkylene is optionally substituted with one or two substituents independently selected from alkyl, halo, haloalkyl, cycloalkyl, hydroxy, or alkoxy; or a pharmaceutically acceptable salt thereof.

Preferably, a compound of Formula (I) wherein:

R$^1$ is hydrogen or alkyl;

R$^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—R$^9$ (where X is —O—, —NR$^{10}$—, —CONR$^{11}$—, —S(O)$_{n1}$—, —NR$^{12}$CO—, —CO—, or —C(O)O— where n1 is 0-2, and R$^9$, R$^{10}$, R$^{11}$, and R$^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in R$^2$ is optionally substituted with one, two, or three R$^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl and further where the aromatic or alicyclic ring in R$^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or R$^1$ and R$^2$ taken together with the carbon atom to which both R$^1$ and R$^2$ are attached form (i) cycloalkylene optionally substituted with one or two R$^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl or (ii) heterocyclylalkylene optionally substituted with one to four R$^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R$^{14}$, -alkylene-S(O)$_{n2}$—R$^{15}$, —COOR$^{16}$, -alkylene-COOR$^{17}$, —CONR$^{18}$R$^{19}$, or -alkylene-CONR$^{20}$R$^{21}$ (where n2 is 0-2 and R$^{14}$-R$^{17}$, R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

R$^3$ is hydrogen or alkyl;

R$^4$ is 1-alkylcyclopentylmethyl, 1-alkylcyclopentylethyl, 1-alkylcyclohexylmethyl, 1-alkylcyclohexylethyl, aryl, aralkyl, heteroaryl, heteroaralkyl, heterocyclylalkyl, or -alkylene-X$^1$—R$^{22}$ (wherein X$^1$ is —NR$^{23}$—, —O—, —S(O)$_{n3}$—, —CO—, —COO—, —OCO—, —NR$^{23}$CO—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$—, or —NR$^{23}$SO$_2$NR$^{24}$— where R$^{23}$ and R$^{24}$ are independently hydrogen, alkyl, or acyl, n3 is 0-2, and R$^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl) wherein said alkylene chain in R$^4$ is optionally substituted with one to six halo and wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

R$^5$ is hydrogen or alkyl;

R$^6$ is hydrogen, alkyl, haloalkyl, cycloalkyl, aryl, aralkyl, heteroaryl, heteroaralkyl, heterocyclyl, or -alkylene-X$^2$—R$^{25}$ (wherein X$^2$ is —NR$^{26}$—, —O—, —S(O)$_{n4}$—, —CO—, —COO—, —OCO—, —NR$^{26}$CO—, —CONR$^{26}$—, —NR$^{26}$SO$_2$—, —SO$_2$NR$^{26}$—, —NR$^{26}$COO—, —OCONR$^{26}$—, —NR$^{26}$CONR$^{27}$—, or —NR$^{26}$SO$_2$NR$^{27}$— where R$^{26}$ and R$^{27}$ are independently hydrogen, alkyl, or acyl, n4 is 0-2, and R$^{25}$ is hydrogen, alkyl, haloalkyl, cycloalkyl, cycloalkylalkyl, heterocyclyl, heterocyclylalkyl, aryl, aralkyl, heteroaryl, or heteroaralkyl) wherein said alkylene chain in R$^6$ is optionally substituted with one to six halo and the aromatic or alicyclic ring in R$^6$ is optionally substituted with one, two, or three R$^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl and further where the aromatic or alicyclic rings in R$^e$ is optionally substituted by one, two or three R$^f$ independently selected from alkyl, alkoxy, haloalkyl, haloalkoxy, halo, hydroxy, carboxy, cyano, nitro, aryl or cycloalkyl;

$R^7$ is haloalkyl; and $R^8$ is hydrogen, alkyl, alkoxyalkyl or haloalkyl; or $R^6$ and $R^8$ together with the carbon atom to which they are attached form cycloalkylene or heterocyclylalkylene wherein said cycloalkylene is optionally substituted with one or two substituents independently selected from alkyl, haloalkyl, hydroxy, or alkoxy and heterocyclylalkylene is optionally substituted with one or two substituents independently selected from alkyl, haloalkyl, hydroxy, or alkoxy; or a pharmaceutically acceptable salt thereof.

Preferably, $R^1$ is hydrogen or alkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl or (ii) heterocyclylalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

$R^3$ is hydrogen or alkyl;

$R^4$ is aryl, aralkyl, heteroaryl, heteroaralkyl, heterocyclylalkyl, or -alkylene-$X^1$—$R^{22}$ (wherein $X^1$ is —$NR^{23}$, —O—, —$S(O)_{n3}$—, —CO—, —COO—, —OCO—, —$NR^{23}CO$—, —$NR^{23}SO_2$—, —$SO_2NR^{23}$—, —$NR^{23}COO$—, —$OCONR^{23}$—, —$NR_{23}CONR^{24}$, or —$NR^{23}SO_2NR^{24}$— where $R^{23}$ and $R^{24}$ are independently hydrogen, alkyl, or acyl, n3 is 0-2, and $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl) wherein said alkylene chain in $R^4$ is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

$R^5$ is hydrogen or alkyl;

$R^6$ is hydrogen, alkyl, haloalkyl, cycloalkyl, aryl, aralkyl, heteroaryl, heteroaralkyl, heterocyclyl, or -alkylene-$X^2$—$R^{25}$ (wherein $X^2$ is —$NR^{26}$, —O—, —$S(O)_{n4}$—, —CO—, —COO—, —OCO—, —$NR^{26}CO$—, —$CONR^{26}$—, —$NR^{26}SO_2$—, —$SO_2NR^{26}$—, —$NR^{26}COO$—, —$OCONR^{26}$—, —$NR^{26}CONR^{27}$—, or —$NR^{26}SO_2NR^{27}$— where $R^{26}$ and $R^{27}$ are independently hydrogen, alkyl, or acyl, n4 is 0-2, and $R^{25}$ is hydrogen, alkyl, haloalkyl, cycloalkyl, cycloalkylalkyl, heterocyclyl, heterocyclylalkyl, aryl, aralkyl, heteroaryl, or heteroaralkyl) wherein said alkylene chain in $R^6$ is optionally substituted with one to six halo and the aromatic or alicyclic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl and further where the aromatic or alicyclic rings in $R^e$ is optionally substituted by one, two or three $R^f$ independently selected from alkyl, alkoxy, haloalkyl, haloalkoxy, halo, hydroxy, carboxy, cyano, nitro, aryl or cycloalkyl;

$R^7$ is haloalkyl; and $R^8$ is hydrogen, alkyl, alkoxyalkyl or haloalkyl; or $R^6$ and $R^8$ together with the carbon atom to which they are attached form cycloalkylene or heterocyclylalkylene wherein said cycloalkylene is optionally substituted with one or two substituents independently selected from alkyl, haloalkyl, hydroxy, or alkoxy and heterocyclylalkylene is optionally substituted with one or two substituents independently selected from alkyl, haloalkyl, hydroxy, or alkoxy.

In a second aspect, this invention is directed to a pharmaceutical composition comprising a compound of Formula (I), individual stereoisomers or a mixture thereof; or a pharmaceutically acceptable salt thereof in admixture with one or more suitable excipients.

In a third aspect, this invention is directed to a method for treating a disease in an animal mediated by cysteine proteases, in particular cathepsin S, which method comprises administering to the animal a pharmaceutical composition comprising a therapeutically effective amount of a compound of Formula (I), individual stereoisomer or a mixture thereof; or a pharmaceutically acceptable salt thereof in admixture with one or more suitable excipients.

In a fourth aspect, this invention is directed to processes for preparing compounds of Formula (I) and the pharmaceutically acceptable salts thereof.

In a fifth aspect, this invention is directed to a method of treating a patient undergoing a therapy wherein the therapy causes an immune response, preferably a deleterious immune response, in the patient comprising administering to the patient a compound of Formula (I) or a pharmaceutically acceptable salt thereof. Preferably, the immune response is mediated by MHC class II molecules. The compound of this invention can be administered prior to, simultaneously, or after the therapy. Preferably, the therapy involves treatment with a biologic. Preferably, the therapy involves treatment with a small molecule.

Preferably, the biologic is a protein or an antibody, preferably a monoclonal antibody. More preferably, the biologic is Remicade®, Refacto®, Referon-A®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3. Preferably, the treatment involves use of heparin, low molecular weight heparin, procainamide or hydralazine.

In a sixth aspect, this invention is directed to a method of treating immune response in an animal that is caused by administration of a biologic to the animal which method comprises administering to the animal in need of such treatment a therapeutically effective amount of a compound of Formula (I) or a pharmaceutically acceptable salt thereof.

In a seventh aspect, this invention is directed to a method of conducting a clinical trial for a biologic comprising administering to an individual participating in the clinical trial a compound of Formula (I) or a pharmaceutically acceptable salt thereof with the biologic.

In an eighth aspect, this invention is directed to a method of prophylactically treating a person undergoing treatment with a biologic with a compound of Formula (I) or a pharmaceutically acceptable salt thereof to treat the immune response caused by the biologic in the person.

In a ninth aspect, this invention is directed to a method of determing the loss in the efficacy of a biologic in an animal due to the immune response caused by the biologic comprising administering the biologic to the animal in the presence and absence of a compound of Formula (I) or a pharmaceutically acceptable salt thereof.

In a tenth aspect, this invention is directed to a method of improving efficacy of a biologic in an animal comprising administering the biologic to the animal with a compound of of Formula (I) or a pharmaceutically acceptable salt thereof.

In an eleventh aspect, this invention is directed to the use of a compound of Formula (I) or a pharmaceutically acceptable salt thereof for the manufacture of a medicament. Preferably, the medicament is for use in the treatment of a disease mediated by Cathepsin S.

In a twelfth aspect, this invention is directed to the use of a compound of Formula (I) or a pharmaceutically acceptable salt thereof for the manufacture of a medicament for combination therapy with a biologic, wherein the compound of this invention treats the immune response caused by the biologic. Preferably, the compound(s) of the invention is administered prior to the administration of the biological agent. Preferably, the compound(s) of the invention is administered concomitantly with the biological agent. Preferably, the compound(s) of the invention is administered after the administration of the biological agent.

DETAILED DESCRIPTION OF THE INVENTION

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl and heterocyclyl rings as defined herein.

"Alkyl" represented by itself means a straight or branched, saturated aliphatic radical containing one to six carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene ($-CH_2-$), ethylene ($-CH_2CH_2-$), trimethylene ($-CH_2CH_2CH_2-$), tetramethylene ($-CH_2CH_2CH_2CH_2-$) 2-methyltetramethylene ($-CH_2CH(CH_3)CH_2CH_2-$), pentamethylene ($-CH_2CH_2CH_2CH_2CH_2-$), and the like.

"Amino" means $-NH_2$ radical. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Alkylamino" or "dialkylamino" refers to a —NHR and —NRR' radical respectively, where R and R' are independently alkyl group as defined above e.g., methylamino, dimethylamino, and the like.

"Alkoxy" refers to a —OR radical where R is an alkyl group as defined above e.g., methoxy, ethoxy, and the like.

"Alkoxycarbonyl" refers to a —C(O)OR radical where R is an alkyl group as defined above e.g., methoxycarbonyl, ethoxycarbonyl, and the like.

"Alkoxycarbonylalkyl" means an -(alkylene)-C(O)OR radical where R is alkyl as defined above e.g., methoxycarbonylmethyl, 2-, or 3-ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" refers to a —OR radical where R is alkoxyalkyl is as defined above e.g., methoxymethyloxy, methoxyethyloxy, and the like.

"Alkoxyalkyloxyalkyl" refers to a -(alkylene)-O-(alkylene)-OR radical where R is an alkyl group as defined above, e.g., 2-methoxyethyloxymethyl, 3-methoxypropyloxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —$COR^a$ where $R^a$ is alkyl, and R' is hydrogen or alkyl as defined above e.g., aminomethyl, methylaminoethyl, dimethylaminoethyl, 1,3-diaminopropyl, acetylaminopropyl, and the like e.g., aminosulfonyl, methylaminosulfonyl, dimethylaminosulfonyl, and the like.

"Aminosulfonyl" refers to a —$SO_2R$ radical where R is —NRR' where R is hydrogen, alkyl, or —$COR^a$ where $R^a$ is alkyl, and R' is hydrogen or alkyl as defined above e.g., aminosulfonyl, methylaminosulfonyl, dimethylaminosulfonyl, and the like.

"Alkylsulfonyl" refers to a —$SO_2R$ radical where R is an alkyl group as defined above e.g., methylsulfonyl, ethylsulfonyl, and the like.

"Acyl" refers to a —COR radical where R is hydrogen, alkyl, haloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are $sp^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aralkyl" refers to a -(alkylene)-R radical where R is aryl as defined above e.g., benzyl, phenethyl, and the like.

"Aryloxy" refers to a —OR radical where R is aryl as defined above e.g., phenoxy, and the like.

"Aralkyloxy" refers to a —OR radical where R is aralkyl as defined above e.g., benzyloxy, and the like.

"Aryloxyalkyl" refers to a -(alkylene)-OR radical where R is aryl as defined above e.g., phenoxymethyl, 2-, or 3-phenoxymethyl, and the like "Aryloxycarbonyl" refers to a —C(O)OR radical where R is aryl as defined above e.g., phenyloxycarbonyl, and the like.

"Arylsulfonyl" refers to a —SO$_2$R radical where R is an aryl group as defined above e.g., phenylsulfonyl, and the like.

"Biologic" means a therapeutic agent originally derived from living organisms for the treatment or management of a disease. Examples include, but are not limited to, proteins (recombinant and plasma derived), monoclonal or polyclonal, humanized or murine antibodies, toxins, hormones, and the like. Biologics are currently available for the treatment of a variety of diseases such as cancer, rheumatoid arthritis, and haemophilia.

"Carboxy" refers to —C(O)OH radical.

"Carboxyalkyl" refers to a -(alkylene)-C(O)OH radical e.g., carboxymethyl, carboxyethyl, and the like.

"Cycloalkyl" refers to a monovalent saturated or partially unsaturated, monocyclic ring containing three to eight ring carbon atoms e.g., cyclopropyl, cyclobutyl, cyclopentyl, cyclohexyl, cyclohexenyl, 2,5-cyclohexadienyl, and the like.

"Cycloalkylalkyl" refers to a -(alkylene)-R radical where R is cycloalkyl as defined above e.g., cyclopropylmethyl, cyclobutylethyl, cyclobutylmethyl, and the like "Cycloalkylene" refers to a divalent saturated or partially unsaturated monocyclic ring containing three to eight ring carbon atoms. For example, the instance wherein "R$^1$ and R$^2$ together with the carbon atom to which both R$^1$ and R$^2$ are attached form cycloalkylene" includes, but is not limited to, the following:

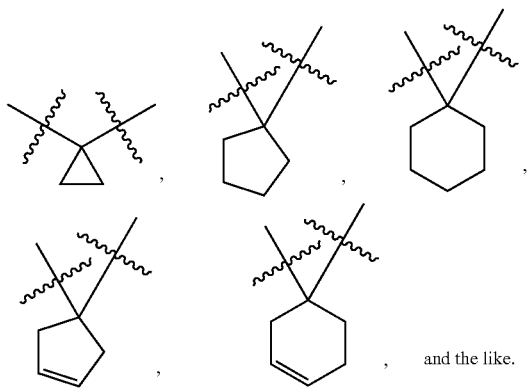

"1-Alkylcyclopentylmethyl or -ethyl and 1-Alkylcyclohexylmethyl or ethyl" means a radical having the formula:

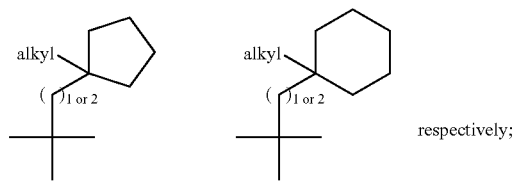

respectively;

e.g., 1-methylcyclopentylmethyl, 1-methylcyclohexylmethyl, and the like

"Disubstituted amino" refers to a —NRR' radical where R is alkyl, aryl, aralkyl, heteroaryl, heteroaralkyl, or heterocyclyl and R' is alkyl, aryl, aralkyl, heteroaryl, heteroaralkyl, cycloalkyl, heterocyclyl, cycloalkylalkyl, hydroxyalkyl, alkoxyalkyl, or acyl as defined herein. Representative examples include, but are not limited to, dimethylamino, methylphenylamino, benzylmethylamino, acetylmethylamino, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Deleterious immune response" means an immune response that prevents effective treatment of a patient or causes disease in a patient. As an example, dosing a patient with a murine antibody either as a therapy or a diagnostic agent causes the production of human antimouse antibodies that prevent or interfere with subsequent treatments. The incidence of antibody formation versus pure murine monoclonals can exceed 70%. (see Khazaeli, M. B. et al. *J. Immunother.* 1994, 15, pp 42-52; Dillman R. O. et al. *Cancer Biother.* 1994, 9, pp 17-28; and Reinsberg, *J. Hybridoma.* 1995, 14, pp 205-208). Additional examples of known agents that suffer from deleterious immune responses are blood-clotting factors such as factor VIII. When administered to hemophilia A patients, factor VIII restores the ability of the blood to clot. Although factor VIII is a human protein, it still elicits an immune response in hemophiliacs as endogenous factor VIII is not present in their blood and thus it appears as a foreign antigen to the immune system. Approximately 29-33% of new patients will produce antibodies that bind and neutralize the therapeutically administered factor VIII (see Lusher J. M. *Semin Thromb Hemost.* 2002, 28(3), pp 273-276). These neutralizing antibodies require the administration of larger amounts of factor VIII in order to maintain normal blood clotting parameters; an expensive regimen of treatment in order to induce immune tolerance (see Briet E et al. *Adv. Exp. Med. Bio.* 2001, 489, pp 89-97).

Another immunogenic example is adenoviral vectors. Retroviral therapy remains experimental and is of limited utility. One reason is that the application of a therapeutic virus generates an immune response capable of blocking any subsequent administration of the same or similar virus (see Yiping Yang et al. *J. of Virology.* 1995, 69, pp 2004-2015). This ensures that retroviral therapies must be based on the transient expression of a protein or the direct incorporation of viral sequence into the host genome. Directed research has identified multiple viral neutralizing epitopes recognized by host antibodies (see Hanne, Gahery-Segard et al. *J. of Virology* 1998. 72, pp 2388-2397) suggesting that viral modifications will not be sufficient to overcome this obstacle. This invention will enable a process whereby an adenoviral therapy will have utility for repeated application.

Another example of an immunogenic agent that elicits neutralizing antibodies is the well-known cosmetic agent Botox. Botulin toxin protein, is purified from the fermentation of *Clostridium botulinum*. As a therapeutic agent, it is used for muscle disorders such as cervical dystonia in addition to cosmetic application. After repeated exposure patients generate neutralizing antibodies to the toxin that results in reduced efficacy (see Birklein F. et al. *Ann Neurol.* 2002, 52, pp 68-73 and Rollnik, J. D. et al. *Neurol. Clin. Neurophysiol.* 2001, 2001(3), pp 2-4).

A "deleterious immune response" also encompasses diseases caused by therapeutic agents. A specific example of this is the immune response to therapy with recombinant human erythropoietin (EPO). Erythropoeitin is used to stimulate the growth or red cells and restore red blood cell counts in patients who have undergone chemotherapy or dialysis. A small percentage of patients develop antibodies to EPO and subsequently are unresponsive to both therapeutically administered EPO and their own endogenous EPO (see Casadevall, N. et al., *NEJM*. 2002, 346, pp 469-475). They contract a disorder, pure red cell aplasia, in which red blood cell production is severely diminished (see Gershon S. K. et. al. *NEJM*. 2002, 346, pp 1584-1586). This complication of EPO therapy is lethal if untreated. Another specific example is the murine antibody, OKT3 (a.k.a., Orthoclone) a monoclonal antibody directed towards CD-3 domain of activated T-cells. In clinical trials 20-40% of patients administered OKT3 produce antibodies versus the therapy. These antibodies besides neutralizing the therapy also stimulate a strong host immune reaction. The immune reaction is severe enough that patients with high titers of human anti-mouse antibodies are specifically restricted from taking the drug (see Orthoclone package label).

A final example is a human antibody therapeutic. Humira® is a monoclonal antibody directed against TNF and is used to treat rheumatoid arthritis patients. When taken alone ~12% of patients develop neutralizing antibodies. In addition, a small percentage of patients given the drug also contract a systemic lupus erthematosus-like condition that is an IgG-mediated immune response induced by the therapeutic agent (see Humira package label).

Another example of "deleterious immune response" is a host reaction to small molecule drugs. It is known to those skilled in the art that certain chemical structures will conjugate with host proteins to stimulate immune recognition (see Ju. C. et al. 2002. *Current Drug Metabolism* 3, pp 367-377 and Kimber I. et al. 2002, *Toxicologic Pathology* 30, pp 54-58.) A substantial portion of this host reactions are IgG mediated. Specific "deleterious immune responses" that are IgG mediated and include: hemolytic anemia, Steven-Johnson syndrome and drug induced Lupus.

"Four atom heterocyclylalkylene" refers to a saturated divalent monocyclic radical of 4 carbon ring atoms wherein one of the ring carbon atoms is replaced by a heteroatom selected from —NR— where R is hydrogen, alkyl, acyl, alkylsulfonyl, aminosulfonyl, hydroxyalkyl, or alkoxyalkyl, —O—, —S—, —SO—, or —S(O)$_2$—. Representative examples include, but are not limited to, rings such as:

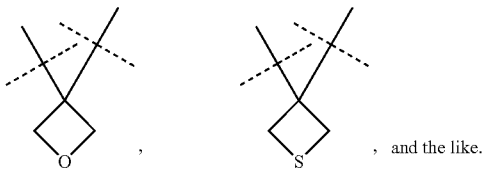

, and the like.

"Halo" refers to fluoro, chloro, bromo or iodo.

"Haloalkyl" refers to alkyl as defined above substituted by one or more, preferably one to five, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like).

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or multicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothienyl, benzimidazolyl, quinolinyl, isoquinolinyl, quinazolinyl, quinoxalinyl, pyrazolyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaryloxyalkyl" refers to a -(alkylene)-OR radical where R is heteroaryl as defined above e.g., furanyloxymethyl, 2-, or 3-indolyloxyethyl, and the like.

"Heteroaryloxy" refers to a —OR radical where R is heteroaryl as defined above.

"Heteroaralkyloxy" refers to a —OR radical where R is heteroaralkyl as defined above.

"Heteroarylsulfonyl" refers to a —SO$_2$R radical where R is an heteroaryl group as defined above e.g., pyridinylsulfonyl, and the like.

"Heterocyclyl" refers to a saturated or partially unsaturated, mono or bicyclic radical of 5 or 6 carbon ring atoms wherein one or more, preferably one, two, or three of the ring carbon atoms are replaced by a heteroatom selected from —N=, —N—, —O—, —S—, —SO—, or —S(O)$_2$— and further wherein one or two ring atoms are optionally replaced by a keto (—CO—) group. The heterocyclyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, quinuclidinyl, and the like.

"Heterocyclylalkyl" refers to a -(alkylene)-heterocyclyl radical as defined in this Application. Representative examples include, but are not limited to, imidazolidin-1-ylmethyl, morpholin-4-ylmethyl, thiomorpholin-4-ylmethyl, thiomorpholin-4-ylmethyl-1-oxide, indolinylethyl, piperazinylmethyl or ethyl, piperidylmethyl or ethyl, pyrrolidinylmethyl or ethyl, and the like.

"Heterocyclylalkylene" refers to a divalent heterocyclyl group, as defined in this Application, e.g., the instance wherein $R^1$ and $R^2$ together with the carbon atom to which both $R^1$ and $R^2$ are attached form heterocyclylalkylene" includes, but is not limited to, the following:

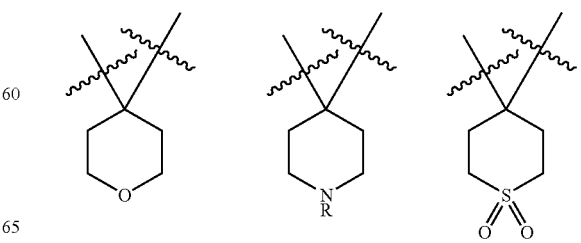

in which R is a substituent defined in the Summary of the Invention

"Hydroxy" means —OH radical. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkyloxy or hydroxyalkoxy" refers to a —OR radical where R is hydroxyalkyl as defined above e.g., hydroxymethoxy, hydroxyethoxy, and the like.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Keto or oxo" means (=O) radical.

"Monosubstituted amino" refers to a —NHR radical where R is alkyl, aryl, aralkyl, heteroaryl, heteroaralkyl, cycloalkyl, cycloalkylalkyl, hydroxyalkyl, alkoxyalkyl, or acyl as defined herein. Representative examples include, but are not limited to, methylamino, phenylamino, benzylamino, cycloalkylmethylamino, acetylamino, trifluoroacetyl, and the like.

"Nitro" means —NO$_2$ radical.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) ontaining a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999.

The expression "... wherein said alkylene chain in $R^4$ or $R^6$ is optionally substituted with one to six halo" in the Summary of the Invention refers to the alkylene chain in -alkylene-$X^1$—$R^{22}$ and -alkylene-$X^2$—$R^{25}$ respectively, being optionally substituted with halo.

The expression "... wherein the aromatic or alicyclic ring in $R^2$, $R^4$, or $R^6$ is optionally substituted with one to three $R^a$, $R^d$, or $R^e$, respectively..." refers to all the groups attached to $R^2$, $R^4$, or $R^6$ that contain an aromatic or alicyclic ring being optionally substituted with one to three $R^a$, $R^d$, or $R^e$ respectively. The aromatic or alicyclic ring may be directly attached to $R^2$, $R^4$, or $R^6$ or be part of a group that is directly attached to $R^2$, $R^4$, or $R^6$. For example, for $R^4$ it includes the aromatic or alicyclic ring in the 1-alkylcyclopentylmethyl, 1-alkylcyclopentylethyl, 1-alkylcyclohexylmethyl, 1-alkylcyclohexylethyl, aryl, aralkyl, heteroaryl, heteroaralkyl, heterocyclylalkyl, or -alkylene-$X^1$—$R^{22}$ (wherein $X^1$ is —$NR^{23}$—, —S(O)$_{n3}$—, —CO—, —COO—, —OCO—, —$NR^{23}$CO—, —$CONR^{23}$—, —$NR^{23}SO_2$—, —$SO_2NR^{23}$—, —$NR^{23}$COO—, —$OCONR^{23}$—, —$NR^{23}CONR^{24}$—, or —$NR^{23}SO_2NR^{24}$— where $R^{23}$ and $R^{24}$ are independently hydrogen, alkyl, or acyl, n3 is 0-2, and $R^{22}$ is cycloalkyl, cycloalkylalkyl, heterocyclyl, aryl, aralkyl, heteroaryl, heteroaralkyl, heterocyclyl, or heterocyclylalkyl) groups being optionally substituted with $R^d$.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Treatment" or "treating" with respect to combination therapy i.e., use with a biologic means any administration of a compound of the present invention and includes:

(1) preventing the immune response from occurring in an animal which may be predisposed to the immune response but does not yet experience or display the pathology or symptomatology of the immune response, (2) inhibiting the immune response in an animal that is experiencing or displaying the pathology or symptomatology of the immune response (i.e., arresting further development of the pathology and/or symptomatology), or (3) ameliorating the immune response in an animal that is experiencing or displaying the pathology or symptomatology of the immune response (i.e., reducing in degree or severity, or extent or duration, the overt manifestations of the immune response or reversing the pathology and/or symptomatology e.g., reduced binding and presentation of antigenic peptides by MHC class II molecules, reduced activation of T-cells and B-cells, reduced humoral and cell-mediated responses and, as appropriate to the particular immune response, reduced inflammation, congestion, pain, necrosis, reduced loss in the efficacy of a biologic agent, and the like).

PREFERRED EMBODIMENTS

Certain compounds of Formula (I) within the broadest scope and in the preferred embodiments set forth in the Summary of the Invention are preferred. For example:

A. One preferred group of compounds is that wherein $R^1$ and $R^2$ are hydrogen.

B. Another preferred group of compounds is that wherein $R^1$ and $R^2$ together with the carbon atom to which they are attached form cycloalkylene optionally substituted with one or two $R^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl. Preferably, $R^1$ and $R^2$ together with the carbon atom to which they are attached form cyclopropylene, cyclobutylene, cyclopentylene, or cyclohexylene optionally substituted with groups described immediately above. More preferably, $R^1$ and $R^2$ together with the carbon atom to which they are attached form cyclopropylene, cyclobutylene, cyclopentylene, cyclohexylene, cycloheptylene, 3-benzylcyclopentylene, 3-cyclohexylmethylcyclopentylene, 3-cyclopentyl-methylcyclopentylene, 3-phenylcyclopentylene, 3-cyclohexylcyclopentylene, 3-cyclopentyl-cyclopentylene, 3-pyridin-2-ylmethylcyclopentylene, 3-pyridin-3-ylmethylcyclopentylene, 3-pyridin-4-ylmethylcyclopropylene, 2-methylcyclopropylene, 2,3-dimethylcyclopropylene, 3-benzylcyclobutylene, 3-methylcyclopentylene, 3,4-dimethylcyclopentylene, 3-ethylcyclopentylene, 3-(1,1-dimethylpropyl)-cyclopentylene, 3-n-butylcyclopentylene, 3-ethoxycarbonylcyclopentylene, 3,4-diethoxycarbonyl-cyclopentylene, or 3-benzyl-4-dimethylaminocyclopentylene. Most preferably, $R^1$ and $R^2$ together with the carbon atom to which they are attached form cyclopropylene.

C. Yet another preferred group of compounds is that wherein $R^1$ and $R^2$ together with the carbon atom to which they are attached form heterocyclylalkylene optionally substituted with one to four $R^c$ which are independently selected from alkyl, haloalkyl, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}R^{14}$, -alkylene-S(O)$_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl.

Preferably, $R^1$ and $R^2$ together with the carbon atom to which they are attached form pyrrolidinyl, piperidinyl, tetrahydropyranyl, tetrahydrothiopyranyl, tetrahydrofuranyl, tetrahydrothiopyran-4-yl-1-oxide, tetrahydrothiopyran-4-yl-1,1-dioxide, hexahydropyrimidinyl, or hexahydropyridazinyl optionally substituted as described above.

More preferably, $R^1$ and $R^2$ together with the carbon atom to which they are attached form piperidin-4-yl substituted with one or two alkyl, haloalkyl, aminoalkyl, alkoxycarbonyl, alkoxyalkyl, alkoxyalkyloxyalkyl, heterocyclyl, heterocyclylalkyl, -alkylene-CONR$^{20}$R$^{21}$, or cycloalkyl. Most preferably, $R^1$ and $R^2$ together with the carbon atom to which they are attached form piperidin-4-yl optionally substituted at the 1-position with methyl, ethyl, propyl, n-butyl, n-pentyl, 3-dimethylaminopropyl, 4-dimethylaminobutyl, 3-morpholin-4-ylpropyl, 3-piperidin-1-yl-propyl, 3-(4-methylpiperazin-1-yl)propyl, 3-(1-methylpiperidin-4-yl)propyl, 4-morpholin-4-ylbutyl, 2-(2-methoxyethyloxy)ethyl, 4-methoxybutyl, 4-aminocarbonylbutyl, 3-aminocarbonylpropyl, morpholin-4-yl, 4-methylpiperazin-1-yl, 1-ethoxycarbonylpiperidin-4-yl, 1,1-dioxotetrahydrothiopyran-4-yl, hydroxy, 2,2,2-trifluoroethyl, tert-butyl, 1,2-dimethylpiperidin-4-yl, 1,2,6-trimethylpiperidin-4-yl, 1,2,2-trimethylpiperidin-4-yl, 1-methyl-2-oxopiperidin-4-yl, 1-methylpiperidin-3-yl, 1-tert-butoxycarbonylpiperidin-4-yl, 1-cyclohexylpiperidin-4-yl, 1-cyclopropylmethylpyrrolidin-3-yl, 1-benzylpyrrolidin-3-yl, 1-benzyloxycarbonylpyrrolidin-3-yl, pyrrolidin-3-yl, 1-hydroxypyrrolidin-3-yl, 1-methylpyrrolidin-3-yl, 1-ethypyrrolidin-3-yl, 1-n-propyl or n-butylpyrrolidin-3-yl, 1-cyclohexylpyrrolidin-3-yl, 1-ethyl-2,2-dimethylpyrrolidin-4-yl, 1-propyl-2-methoxy-carbonylpiperidin-4-yl, 2-oxopyrrolidin-3-yl, 1-ethyl-2-oxopyrrolidin-3-yl, morpholin-4-yl, 1-(1-methylpiperidin-4-ylcarbonyl)piperidin-4-yl, 1-ethoxycarbonylpiperidin-4-yl, 1-benzylazetidin-3-yl, tetrahydrothiopyran-4-yl-1-oxide, or tetrahydrothiopyran-4-yl-1,1-dioxide. Particularly preferably, $R^1$ and $R^2$ together with the carbon atom to which they are attached form piperidin-4-yl optionally substituted at the 1-position with methyl, ethyl, propyl, n-butyl, or 2,2,2-trifluoroethyl, tetrahydrothiopyran-4-yl, tetrahydrothiopyran-4-yl-1-oxide, tetrahydrothiopyran-4-yl-1,1-dioxide, or tetrahydropyran-4-yl.

(a) Within the above preferred groups (A-C) and the more preferred groups contained therein, an even more preferred group of compounds is that wherein:

$R^4$ is aralkyl, heteroaralkyl, heterocyclylalkyl, or -alkylene-X$^1$—R$^{22}$ (wherein X$^1$ is
—NR$^{23}$—, —O—, —S(O)$_{n3}$—, —CO—, —COO—, -OCO—, —NR$^{23}$CO—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$, or —NR$^{23}$SO$_2$NR$^{24}$— where R$^{23}$ and R$^{24}$ are independently hydrogen, alkyl, or acyl, n3 is 0-2, and R$^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl) wherein said alkylene chain in R$^4$ is optionally substituted with one to six halo and wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; and $R^3$ and $R^5$ are hydrogen.

Preferably, $R^4$ is tetrahydronaphthylmethyl, benzyl, 4-methoxybenzyl, 4-dimethylaminobutyl, 2-dimethylaminocarbonylethyl, dimethylaminocarbonylmethyl, methoxycarbonylmethyl, 3,4-dichlorobenzyl, 2-chlorobenzyl, 4-ethoxybenzyl, 4-nitrobenzyl, biphen-4-ylmethyl, naphth-1-ylmethyl, naphth-2-ylmethyl, 4-chlorobenzyl, 3-chlorobenzyl, 4-fluorobenzyl, 2-phenethyl, 4-hydroxybenzyl, 2-(4-hydroxyphenyl)ethyl, 2,6-difluorobenzyl, 2,2-difluoro-3-phenylpropyl, 2,2-dichloro-3-phenylpropyl, (cyanomethylmethylcarbamoyl)-methyl, biphenyl-3-ylmethyl, naphth-2-yl, 3-phenylpropyl, or 2,2-dimethyl-3-phenylpropyl and $R^3$ and $R^5$ are hydrogen.

Preferably, $R^4$ is ethylthiomethyl, ethylsulfinylmethyl, ethylsulfonylmethyl, isopropylthiomethyl, 2-methylthioethyl, 2-methylsulfinylethyl, 2-methysulfonylethyl,
2-methylpropylsulfonylmethyl, isobutylsulfanylmethyl, tert-butylthiomethyl, benzenesulfonylmethyl, 2-phenylsulfanylethyl, 2-phenylsulfonylethyl, naphth-2-ylmethane-sulfonylmethyl, biphenyl-2-ylmethanesulfonylmethyl, biphenyl-4-ylmethanesulfonylmethyl, phenylmethanesulfanylmethyl, phenylmethanesulfinylmethyl, phenylmethanesulfonylmethyl, 2-phenylmethanesulfonylethyl, 4-tert-butylphenylmethanesulfonylmethyl, 2-fluorophenyl-methanesulfanylmethyl, 2-fluorophenylmethanesulfonylmethyl, 3-fluorophenylmethane-sulfonylmethyl, 4-fluorophenylmethanesulfonylmethyl, 2-chlorophenylmethanesulfanylmethyl, 2-chlorophenylmethanesulfonylmethyl, 3-chlorophenylmethanesulfonylmethyl,
4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenylmethane-sulfonylmethyl, 2-trifluoromethylphenylmethane-sulfanylmethyl, 2-trifluoromethylphenyl-methanesulfonylmethyl, 3-trifluoromethylphenylmethanesulfonylmethyl,
4-trifluoromethylphenylmethanesulfonylmethyl, 2-cyanophenyl-methanesulfanylmethyl, 2-cyanophenylmethanesulfonylmethyl, 3-cyanophenylmethanesulfonylmethyl, 2-bromophenylmethanesulfonylmethyl, 2-nitrophenylmethanesulfanylmethyl, 2-nitrophenylmethanesulfonylmethyl, 2-methylphenylmethanesulfonylmethyl, 3-methylphenylmethanesulfonylmethyl,
4-methylphenylmethanesulfonylmethyl, 2-(4-trifluoromethoxy-benzenesulfonyl)ethyl, 2-(3-trifluoromethoxybenzenesulfonyl)-ethyl, 2-(2-trifluoromethoxy-benzenesulfonyl)-ethyl, 2-difluoromethoxyphenylmethanesulfonylmethyl, 3-difluoromethoxyphenylmethanesulfonylmethyl, 4-difluoromethoxyphenylmethanesulfonylmethyl, 2-(4-difluoromethoxybenzenesulfonyl)ethyl, 2-(2-difluoromethoxybenzene-sulfonyl)ethyl, 2-(3-difluoromethoxybenzenesulfonyl)ethyl, 3-chloro-2-fluorophenylmethane-sulfonylmethyl, 3,5-dimethylphenylmethanesulfonylmethyl, 3,5-bis-trifluoromethylphenylmethanesulfonylmethyl, 2,5-difluorophenylmethane-sulfonylmethyl, 2,6-difluorophenylmethanesulfonylmethyl, 2,3-difluorophenylmethane-sulfonylmethyl, 3,4-difluorophenylmethanesulfonylmethyl, 2,4-difluorophenylmethane-sulfonylmethyl, 2,5-dichlorophenylmethanesulfonylmethyl, 3,4-dichlorophenylmethane-sulfonylmethyl, 2,6-dichlorophenylmethanesulfonylmethyl, 2-fluoro-3-methylphenyl-methanesulfonyl-methyl, 4-fluoro-2-trifluoromethoxyphenylmethanesulfonylmethyl, 2-fluoro-6-trifluoromethyl-phenylmethanesulfonylmethyl, 2-fluoro-3-trifluoromethylphenyl-methanesulfonylmethyl, 2-fluoro-4-trifluoromethylphenylmethanesulfonylmethyl, 2-fluoro-5- trifluoromethyl-phenylmethanesulfonylmethyl, 4-fluoro-3-trifluoromethyl-phenylmethanesulfonylmethyl, 2-chloro-5-trifluoromethylphenylmethane-sulfonylmethyl, 2,4,6-trifluorophenylmethane-sulfonylmethyl, 2,4,5-trifluorophenylmethanesulfonylmethyl, 2,3,4-trifluorophenyl-methanesulfonylmethyl, 2,3,5-trifluorophenylmethanesulfonylmethyl, 2,5,6-trifluorophenylmethanesulfonyl-methyl, 3,4,5-trimethoxyphenylmethanesulfonylmethyl, pyridin-2-ylmethanesulfonylmethyl, pyridin-3-ylmethanesulfonylmethyl, pyridin-4-yl-methanesulfonylmethyl, 2-(pyridin-2-ylsulfonyl)ethyl, 2-(pyridin-4-ylsulfonyl)ethyl, oxypyridin-2-ylmethane-sulfonylmethyl, cyclohexylmethanesulfanylmethyl, cyclohexylmethanesulfinylmethyl, cyclohexylmethanesulfonylmethyl, cyclopropylmethane-sulfonylmethyl, thiophene-2-sulfonylmethyl, 5-chlorothien-2-ylmethanesulfonylmethyl, or 3,5-dimethyl-isoxazol-4-ylmethanesulfonylmethyl, preferably 2-(difluoromethoxy)phenyl-methanesulfonylmethyl and $R^3$ and $R^5$ are hydrogen.

Preferably, $R^4$ is 1-ethoxycarbonylpiperidin-4-ylmethyl, 1-methylpiperidin-4-ylmethyl, 2-tetrahydropyran-4-ylethyl, pyrrolidin-1-ylmethyl, piperidin-1-ylmethyl, morpholin-4-yl-methyl, 1-morpholin-4-ylethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothio-pyran-4-ylmethyl, 1,1-dioxotetrahydrothiopyran-4-ylmethyl, 1-methylpiperazin-4-ylmethyl, benzyloxymethyl, ethoxymethyl, isopropyloxymethyl, 2-dimethylaminoethyl, 2-piperidin-1-ylethyl, 2-pyrrolidin-1-ylethyl, tert-butyloxymethyl, imidazol-4-ylmethyl, indol-3-ylmethyl, 2-pyrrolidin-1-ylcarbonylethyl, pyrrolidin-1-ylcarbonylmethyl, indol-2-ylmethyl, 1-benzylimidazol-4-ylmethyl, 4-ethyl-4-methylpiperidin-1-ylmethyl, indol-1-ylmethyl, 1-methylpiperidin-2-ylmethyl, 2,2,-difluoro-3-thien-2-ylmethyl, or pyridin-4-ylmethyl and $R^3$ and $R^5$ are hydrogen.

Most preferably, $R^4$ is isopropylsulfonylmethyl, cyclopropylmethanesulfonylmethyl, 2-phenylsulfonylethyl, pyridin-4-ylsulfonylmethyl, pyridin-2-ylmethanesulfonylmethyl, pyridin-3-ylmethanesulfonylmethyl, benzylsulfonylmethyl i.e., phenylmethanesulfonylmethyl, 2-difluoromethoxyphenylmethanesulfonylmethyl, 2-chlorophenyl, or pyridin-4-yl-methyl; and $R^3$ and $R^5$ are hydrogen.

(b) Within the above preferred groups (A-C) and the more preferred groups contained therein, another even more preferred group of compounds is that wherein:

$R^4$ is 1-methylcyclopentylmethyl or 1-methylcyclohexylmethyl; and $R^3$ and $R^5$ are hydrogen.

(c) Within the above preferred groups (A-C) and the more preferred groups contained therein, yet another even more preferred group of compounds is that wherein:

$R^4$ is heteroaralkyl optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl. Preferably, pyrimidinylmethane-sulfanylmethyl, pyrimidinylmethanesulfmylmethyl, pyrimidinylmethanesulfonylmethyl, pyrazinylmethane-sulfanylmethyl, pyrazinylmethanesulfinylmethyl, pyrazinylmethane-sulfonylmethyl, pyridazinylmethanesulfanylmethyl, pyridazinyl methanesulfinylmethyl, or pyridazinylmethanesulfonylmethyl, preferably pyrazin-2-ylmethanesulfonylmethyl; and $R^3$ and $R^5$ are hydrogen.

(1) Within the above preferred, more preferred, and even more preferred groups above i.e., A, A(a-c), B, B(a-c), C and C(a-c), and preferred groups contained therein, a particularly preferred group of compounds is that wherein:

$R^6$ is alkyl, haloalkyl, cycloalkyl, phenyl, benzyl, naphthyl, alkylSO$_2$alkyl, cycloalkylSO$_2$alkyl, arylSO$_2$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein the aromatic or alicyclic ring in $R^6$ is optionally substituted by one, two, or three $R^e$;

each $R^e$ is independently alkyl, halo, hydroxy, oxo, carboxy, cyano, nitro, cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, alkoxy, —COR (where R is alkyl), alkoxycarbonyl, aryloxycarbonyl where the aromatic or alicyclic rings in $R^e$ may be further optionally substituted by one, two or three $R^f$ independently selected from alkyl, alkoxy, haloalkyl, haloalkoxy, halo, hydroxy, carboxy, cyano, nitro, aryl or cycloalkyl.

Preferably, $R^6$ is methyl, ethyl, isopropyl, trifluoromethyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, or pyrazinyl wherein the aromatic or alicylic rings in $R^6$ are optionally substituted with one, two, or three $R^e$ independently selected from methyl, ethyl, fluoro, chloro, bromo, iodo, hydroxy, oxo, carboxy, cyano, nitro, cyclopropyl, phenyl, pyrrolidinyl, piperidinyl, morpholinyl, thiomorpholinyl, piperazinyl, thienyl, imidazolyl, methoxy, acetyl, or methoxycarbonyl wherein the aromatic or alicyclic rings in $R^e$ are further optionally substituted with one, two, or three $R^f$ independently selected from methyl, cyclopropyl, phenyl, methoxy, fluoro, chloro, hydroxy, or carboxy. Preferably, $R^6$ is methyl.

Even more preferably, $R^6$ is phenyl, naphthyl, pyrrolidinyl, piperidinyl, morpholinyl, thiomorpholinyl, furanyl, thienyl, thiazolyl, imidazolyl, pyridinyl, or pyrazinyl wherein the aromatic or alicyclic rings in $R^6$ are optionally substituted with one, two, or three $R^e$ independently selected from methyl, fluoro, chloro, phenyl, thienyl, methoxy, acetyl, or methoxycarbonyl. Preferably, $R^6$ is phenyl, naphthyl, pyrrolidinyl, piperidinyl, furanyl, thienyl, thiazolyl, imidazolyl, pyridinyl, or pyrazinyl wherein the aromatic or alicyclic rings in $R^6$ are optionally substituted with one, two, or three $R^e$ independently selected from methyl, fluoro, chloro, phenyl, thienyl, methoxy, acetyl, or methoxycarbonyl. Most preferably, $R^6$ is phenyl, 4-methoxyphenyl, 4-chlorophenyl, 4-fluorophenyl, 2-fluorophenyl, 2-fluoro-4-chlorophenyl, naphthyl, piperidin-4-yl, furanyl, thienyl, pyridin-4-yl, or pyrazinyl. Particularly preferably, $R^6$ is phenyl, 4-fluorophenyl, thiophen-2-yl, furan-2-yl, 2-hydroxyphenyl, 1-methylpyrrol-2-yl, or indol-3-yl, preferably, phenyl, 4-fluorophenyl, thiophen-2-yl, or furan-2-yl.

(2) Within the above preferred, more preferred, and even more preferred groups above i.e., A, A(a-c), B, B(a-c), C and C(a-c), and preferred groups contained therein, a particularly preferred group of compounds is that wherein $R^8$ is hydrogen or haloalkyl, preferably hydrogen or trifluoromethyl.

Within the above preferred, more preferred, and even more preferred groups above i.e., A, A(a-c), A(a-c)(1), A(a-c)(2), B, B(a-c), B(a-c)(1), B(a-c)(2), C, C(a-c), C(a-c)(1), C(a-c)(2), and preferred groups contained therein, a particularly preferred group of compounds is that wherein $R^7$ is trifluoromethyl or 2,2,2-trifluoroethyl, more preferably trifluoromethyl; and $R^8$ is hydrogen.

(3) Within the above preferred, more preferred, and even more preferred groups above i.e., A, A(a-c), B, B(a-c), C and C(a-c), another particularly preferred group of compounds is that wherein:

$R^6$ and $R^8$ together with the carbon to which they are attached from cycloalkylene, preferably cyclopentylene, cyclopent-1-enylene, cyclohexylene, cyclohex-1-enylene.

(4) Within the above preferred, more preferred, and even more preferred groups above i.e., A, A(a-c), B, B(a-c), C and C(a-c), yet another particularly preferred group of compounds is that wherein:

$R^6$ and $R^8$ together with the carbon to which they are attached from heterocyclylalkylene, preferably tetrahydropyran-4-yl or 3,6-dihydro-2H-pyran-4-yl.

Within the above preferred, more preferred, and even more preferred groups above i.e., A(a-c)(3), A(a-c)(4), B(a-c)(3), B(a-c)(4), C(a-c)(3), and C(a-c)(4), and preferred groups contained therein, most preferred group of compounds is that wherein $R^7$ is trifluoromethyl or 2,2,2-trifluoroethyl, more preferably trifluoromethyl.

(d) Within the above preferred and more preferred groups (A-C) and more preferred groups contained therein, another even more preferred group of compounds is that wherein $R^6$ is phenyl, naphthyl, pyrrolidinyl, piperidinyl, morpholinyl, thiomorpholinyl, furanyl, pyranyl, thienyl, thiazolyl, imidazolyl, pyridinyl, or pyrazinyl wherein the aromatic or alicyclic rings in $R^3$ are optionally substituted with one, two, or three $R^e$ independently selected from methyl, fluoro, chloro, phenyl, thienyl, methoxy, acetyl, or methoxycarbonyl. Most preferably, $R^6$ is phenyl, 4-methoxyphenyl, 4-chlorophenyl, 4-fluorophenyl, 2-fluorophenyl, 2-fluoro-4-chlorophenyl, naphthyl, piperidin-4-yl, furanyl, thienyl, pyridin-4-yl, or pyrazinyl.

Within the above preferred, more preferred, and even more preferred groups above i.e., Ad, Bd, and Cd, and preferred groups contained therein, a more preferred group of compounds is that wherein $R^7$ is trifluoromethyl or 2,2,2-trifluoroethyl, more preferably trifluoromethyl; and $R^3$, $R^5$, and $R^8$ are hydrogen.

(D) Yet another preferred group of compounds of Formula (I) is that wherein:

$R^4$ is -alkylene-S(O)$_2$—$R^{22}$ where $R^{22}$ is aralkyl, heteroaralkyl, or cycloalkylalkyl wherein the alkylene chain in $R^4$ is optionally substituted with one to six halo and further wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl.

(i) Within this group (D), a more preferred group of compounds is that wherein:

$R^1$ and $R^2$ are hydrogen or $R^1$ and $R^2$ together with the carbon atom to which they are attached form cycloalkylene or heterocycloalkylene;

$R^3$ is hydrogen;

$R^4$ is -alkylene-S(O)$_2$—$R^{22}$ where $R^{22}$ is aralkyl, heteroaryalkyl, or cycloalkylalkyl wherein the the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, amino, monsubstituted amino, disubstituted amino, or acyl;

$R^5$ is hydrogen;

$R^6$ is aryl, or heteroaryl wherein the aromatic or alicyclic rings in $R^6$ are optionally substituted by one, two, or three $R^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, carboxy, alkoxycarbonyl, arylsulfonyl, alkylsulfonyl, aminosulfonyl, or aminoalkyl;

$R^7$ is haloalkyl; and $R^8$ is hydrogen.

(ii) Within this group (D), another more preferred group of compounds is that wherein:

$R^1$ and $R^2$ are hydrogen or $R^1$ and $R^2$ together with the carbon atom to which they are attached form cyclopropylene, preferably cyclopropylene;

$R^3$ is hydrogen;

$R^4$ is —CH$_2$—SO$_2$—$R^{22}$ where $R^{22}$ is aralkyl, heteroaryalkyl, or cycloalkylalkyl wherein the the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, amino, monsubstituted amino, disubstituted amino, or acyl, preferably methyl, ethyl, trifluoromethyl, methoxy, ethoxy, propoxy, hydroxyl, trifluoromethoxy, difluoromethoxy, chloro, fluoro, nitro, cyano, carboxy, methoxycarbonyl;

$R^5$ is hydrogen;

$R^6$ is aryl, or heteroaryl wherein the aromatic or alicyclic rings in $R^6$ are optionally substituted by one, two, or three $R^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, carboxy, alkoxycarbonyl, arylsulfonyl, alkylsulfonyl, aminosulfonyl, or aminoalkyl;

$R^7$ is haloalkyl; and $R^8$ is hydrogen.

With the group D, D(i) and D(ii), a more preferred group of compounds is that wherein:

$R^1$ and $R^2$ together with the carbon atom to which they are attached form cyclopropylene; and $R^4$ is phenylmethanesulfonylmethyl, 4-tert-butylphenylmethanesulfonylmethyl, 2-fluorophenylmethanesulfonylmethyl, 3-fluorophenylmethanesulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenylmethane-sulfonylmethyl, 2-trifluoromethylphenylmethane-sulfonylmethyl, 3-trifluoromethylphenylmethanesulfonylmethyl, 4-trifluoromethylphenyl-methanesulfonylmethyl, 2-cyanophenylmethanesulfonylmethyl, 3-cyanophenylmethane-sulfonylmethyl, 2-bromophenylmethanesulfonylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-difluoromethoxyphenylmethanesulfonylmethyl, 3-difluoromethoxyphenylmethanesulfonylmethyl, 4-difluoromethoxyphenylmethane-sulfonylmethyl, 3-chloro-2-fluorophenylmethane-sulfonylmethyl, 3,5-dimethylphenylmethanesulfonylmethyl, 3,5-bis-trifluoromethylphenylmethanesulfonylmethyl, 2,5-difluorophenylmethanesulfonylmethyl, 2,6- difluorophenylmethanesulfonylmethyl, 2,3-difluorophenylmethane-sulfonylmethyl, 3,4-difluorophenylmethanesulfonylmethyl, 2,4-difluorophenylmethanesulfonylmethyl, 2,5-dichlorophenylmethanesulfonylmethyl, 3,4-dichlorophenylmethanesulfonylmethyl, 2,6-dichlorophenylmethanesulfonylmethyl, 2-fluoro-3-methylphenylmethanesulfonyl-methyl, 4-fluoro-2-trifluoromethoxyphenylmethane-sulfonylmethyl, 2-fluoro-6-trifluoromethylphenyl-methanesulfonylmethyl, 2-fluoro-3-trifluoro-methylphenyl-methanesulfonylmethyl, 2-fluoro-4-trifluoromethylphenylmethanesulfonyl-methyl, 2-fluoro-5-trifluoromethyl-phenylmethanesulfonylmethyl, 4-fluoro-3-trifluoromethyl-phenylmethanesulfonylmethyl, 2-chloro-5-trifluoromethylphenylmethane-sulfonylmethyl, 2,4,6-trifluorophenylmethane-sulfonylmethyl, 2,4,5-trifluorophenylmethanesulfonylmethyl, 2,3,4-trifluorophenyl-methanesulfonylmethyl, 2,3,5-trifluorophenylmethanesulfonylmethyl, 2,5,6-trifluorophenylmethanesulfonyl-methyl, 3,4,5-trimethoxyphenylmethanesulfonylmethyl, pyridin-2-ylmethanesulfonylmethyl, pyridin-3-ylmethanesulfonylmethyl, pyridin-4-ylmethane-sulfonylmethyl, N-oxypyridin-2-ylmethanesulfonylmethyl, 2-trifluoropyridin-6-ylmethane-sulfonylmethyl, pyrazin-2-ylmethanesulfonylmethyl, cyclohexylmethane-sulfonylmethyl, cyclopropylmethanesulfonylmethyl, thiophene-2-sulfonylmethyl, 5-chlorothien-2-ylmethane-sulfonylmethyl, or 3,5-dimethylisoxazol-4-ylmethane-sulfonylmethyl.

With the group D, D(i), D(ii), D(i)(a) and D(ii)(a), a more preferred group of compounds is that wherein:
$R^1$ and $R^2$ together with the carbon atom to which they are attached form cyclopropylene;
$R^4$ is phenylmethanesulfonylmethyl, 4-fluorophenyl-methanesulfonylmethyl, cyclopropylmethanesulfonylmethyl, pyridin-2-ylmethanesulfonylmethyl, 2-trifluoromethylpyridin-6-ylmethanesulfonylmethyl, 2-difluoromethoxyphenylmethane-sulfonylmethyl, or pyrazin-2-ylmethanesulfonylmethyl;
$R^6$ is furan-2-yl, indol-3-yl, thiophen-2-yl, 1-methylpyrrol-2-yl, 1-phenylsulfonyl-pyrrol-2-yl, pyridin-2-yl, or phenyl optionally substituted with one, two, or three $R^e$ independently selected from alkyl, hydroxyl, or halo. Preferably, $R^6$ is furan-2-yl, indol-3-yl, thiophen-2-yl, 1-methylpyrrol-2-yl, 1-phenylsulfonylpyrrol-2-yl, pyridin-2-yl, phenyl, 2-hydroxyphenyl, 4-hydroxyphenyl, 3-chloro-4-hydroxyphenyl, 3-bromophenyl, 4-fluorophenyl, 3,4-difluorophenyl, or 3,4,5-trifluorophenyl. Even more preferably, $R^6$ is phenyl, 2-hydroxyphenyl, 4-hydroxyphenyl, or 4-fluorophenyl; and
$R^7$ is 2,2,3,3,3-pentafluoroethyl, trifluoromethyl or difluoromethyl, preferably trifluoromethyl.

With the group D, D(i), D(ii), D(i)(a) and D(ii)(a), a more preferred group of compounds is that wherein:
$R^1$ and $R^2$ together with the carbon atom to which they are attached form cyclopropylene;
$R^4$ is phenylmethanesulfonylmethyl, 4-fluorophenyl-methanesulfonylmethyl, cyclopropylmethanesulfonylmethyl, pyridin-2-ylmethanesulfonylmethyl, 2-trifluoromethylpyridin-6-ylmethanesulfonylmethyl, 2-difluoromethoxyphenylmethane-sulfonylmethyl, or pyrazin-2-ylmethanesulfonylmethyl;
$R^6$ is furan-2-yl, indol-3-yl, thiophen-2-yl, 1-methylpyrrol-2-yl, 1-phenylsulfonyl-pyrrol-2-yl, pyridin-2-yl, or phenyl optionally substituted with one, two, or three $R^e$ independently selected from alkyl, hydroxyl, or halo. Preferably, $R^6$ is furan-2-yl, indol-3-yl, thiophen-2-yl, 1-methylpyrrol-2-yl, 1-phenylsulfonylpyrrol-2-yl, pyridin-2-yl, phenyl, 2-hydroxyphenyl, 4-hydroxyphenyl, 3-chloro-4-hydroxyphenyl, 3-bromophenyl, 4-fluorophenyl, 3,4-difluorophenyl, or 3,4,5-trifluorophenyl. Even more preferably, $R^6$ is phenyl, 2-hydroxyphenyl, 4-hydroxyphenyl, or 4-fluorophenyl; and
$R^7$ is 2,2,3,3,3-pentafluoroethyl, trifluoromethyl or difluoromethyl, preferably trifluoromethyl.

Most preferably, in the compounds above the stereochemistry at the carbon to which $R^4$ is attached is (R) and to which $R^6$ is attached is (S) when $R^6$ is phenyl, 2-hydroxyphenyl, 4-hydroxyphenyl, or 4-fluorophenyl.

Reference to the preferred embodiments set forth above is meant to include all combinations of particular and preferred groups unless stated otherwise.

TABLE I

Compounds of Formula (I) where $R^3$, $R^5$ and $R^8$ are hydrogen, $R^1$, $R^2$, $R^4$, $R^6$ and $R^7$ are as defined in Table I below are

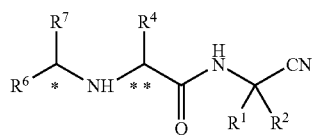

(I)

| Cpd # | Stereochem at (*C, **C) | $R^1 + R^2$ | $R^4$ | $R^6$ | $R^7$ |
|---|---|---|---|---|---|
| 1 | (S, R) | cyclopropyl | phenylmethanesulfonylmethyl | phenyl | $CF_3$ |
| 2 | (S, R) | 1-$C_2H_5$piperidin-4-yl | phenylmethanesulfonylmethyl | phenyl | $CF_3$ |
| 3 | (S, R) | 1,1-dioxohexa-hydro-1$\lambda^6$-thiopyran-4-yl | phenylmethanesulfonylmethyl | phenyl | $CF_3$ |
| 4 | (S, R) | cyclopropyl | phenylmethanesulfanylmethyl | 4-OHphenyl | $CF_3$ |
| 5 | (S, R) | cyclopropyl | cyclopropylmethanesulfonylmethyl | phenyl | $CF_3$ |
| 6 | (RS, R) | cyclopropyl | phenylmethanesulfanylmethyl | furan-2-yl | $CF_3$ |
| 7 | (RS, R) | cyclopropyl | phenylmethanesulfonylmethyl | furan-2-yl | $CF_3$ |
| 8 | (S, R) | cyclopropyl | cyclopropylmethanesulfonylmethyl | 3-Brphenyl | $CF_3$ |
| 9 | (PS, R) | cyclopropyl | phenylmethanesulfanylmethyl | indol-3-yl | $CF_3$ |
| 10 | (RS, R) | cyclopropyl | phenylmethanesulfonylmethyl | indol-3-yl | $CF_3$ |
| 11 | (RS, R) | cyclopropyl | phenylmethanesulfanylmethyl | thiophen-2-yl | $CF_3$ |
| 12 | (RS, R) | cyclopropyl | phenylmethanesulfonylmethyl | thiophen-2-yl | $CF_3$ |
| 13 | (S, R) | cyclopropyl | cyclopropylmethanesulfonylmethyl | 4-Fphenyl | $CF_3$ |

TABLE I-continued

Compounds of Formula (I) where $R^3$, $R^5$ and $R^8$ are hydrogen, $R^1$, $R^2$, $R^4$, $R^6$ and $R^7$ are as defined in Table I below are

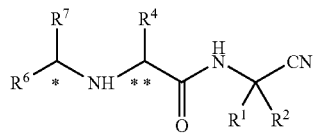

(I)

| Cpd # | Stereochem at (*C, **C) | $R^1 + R^2$ | $R^4$ | $R^6$ | $R^7$ |
|---|---|---|---|---|---|
| 14 | (S, R) | cyclopropyl | phenylmethanesulfonylmethyl | methyl | $CF_3$ |
| 15 | (S, R) | cyclopropyl | phenylmethanesulfonylmethyl | 1-$CH_3$pyrrol-2-yl | $CF_3$ |
| 16 | (S, S) | cyclopropyl | 1-methylcyclopentylmethyl | thiophen-2-yl | $CF_3$ |
| 17 | (R, S) | cyclopropyl | 1-methylcyclopentylmethyl | thiophen-2-yl | $CF_3$ |
| 18 | (S, R) | cyclopropyl | phenylmethanesulfonylmethyl | 4-Fphenyl | $CF_3$ |
| 19 | (RS, R) | cyclopropyl | pyridin-2-ylmethanesulfanylmethyl | phenyl | $CF_3$ |
| 20 | (S, R) | cyclopropyl | pyridin-2-ylmethanesulfonylmethyl | phenyl | $CF_3$ |
| 21 | (S, S) | cyclopropyl | 1-methylcyclopentylmethyl | 2-OH-phenyl | $CF_3$ |
| 22 | (R, S) | cyclopropyl | 1-methylcyclopentylmethyl | 4-OH-phenyl | $CF_3$ |
| 23 | (R, R) | cyclopropyl | pyridin-2-ylmethanesulfonylmethyl | phenyl | $CF_3$ |
| 24 | (S, S) | cyclopropyl | 1-methylcyclopentylmethyl | 4-OH-phenyl | $CF_3$ |
| 25 | (RS, S) | cyclopropyl | 2-Clbenzyl | phenyl | $CF_3$ |
| 26 | (RS, S) | cyclopropyl | 2-Clbenzyl | 4-F-phenyl | $CF_3$ |
| 27 | (RS, R) | cyclopropyl | pyridin-2-ylmethanesulfonylmethyl | 4-F-phenyl | $CF_3$ |
| 28 | (S, R) | cyclopropyl | phenylmethanesulfonylmethyl | 4-OH-phenyl | $CF_3$ |
| 29 | (R, R) | cyclopropyl | phenylmethanesulfanylmethyl | 3-Cl-4-OH-phenyl | $CF_3$ |
| 30 | (S, R) | cyclopropyl | phenylmethanesulfanylmethyl | 3-Cl-4-OH-phenyl | $CF_3$ |
| 31 | (R, R) | cyclopropyl | phenylmethanesulfonylmethyl | 3-Cl-4-OH-phenyl | $CF_3$ |
| 32 | (S, R) | cyclopropyl | phenylmethanesulfonylmethyl | 3-Cl-4-OH-phenyl | $CF_3$ |
| 33 | (R, S) | cyclopropyl | 1-methylcyclopentylmethyl | thiophen-2-yl | $CHF_2$ |
| 34 | (RS, R) | cyclopropyl | phenylmethanesulfanylmethyl | thiophen-2-yl | $CHF_2$ |
| 35 | (S, S) | cyclopropyl | 1-methylcyclopentylmethyl | 3-F-4-OH-phenyl | $CF_3$ |
| 36 | (RS, R) | cyclopropyl | phenylmethanesulfanylmethyl | pyridin-2-yl | $CF_3$ |
| 37 | (RS, S) | cyclopropyl | 2-pyridin-2-ylsulfanylethyl | 4-F-phenyl | $CF_3$ |
| 38 | (RS, S) | cyclopropyl | 2-pyridin-2-ylsulfonylethyl | 4-F-phenyl | $CF_3$ |
| 39 | (RS, R) | cyclopropyl | phenylmethanesulfonylmethyl | pyridin-2-yl | $CF_3$ |
| 40 | (R, R) | cyclopropyl | phenylmethanesulfonylmethyl | thiophen-2-yl | $CHF_2$ |
| 41 | (RS, R) | cyclopropyl | 2-$CHF_2$Ophenylmethanesulfanylmethyl | thiophen-2-yl | $CF_3$ |
| 42 | (PS, R) | cyclopropyl | 2-$CHF_2$Ophenylmethanesulfonylmethyl | thiophen-2-yl | $CF_3$ |
| 43 | (S, R) | cyclopropyl | pyridin-2-ylmethanesulfanylmethyl | 4-F-phenyl | $CF_3$ |
| 44 | (S, R) | cyclopropyl | pyridin-2-ylmethanesulfonylmethyl | 4-F-phenyl | $CF_3$ |
| 45 | (R, R) | cyclopropyl | pyridin-2-ylmethanesulfanylmethyl | 4-F-phenyl | $CF_3$ |
| 46 | (R, R) | cyclopropyl | pyridin-2-ylmethanesulfonylmethyl | 4-F-phenyl | $CF_3$ |
| 47 | (S, R) | cyclopropyl | cyclopropylmethanesulfonylmethyl | thiophen-3-yl | $CF_3$ |
| 48 | (RS, R) | cyclopropyl | cyclopropylmethanesulfanylmethyl | thiophen-2-yl | $CF_3$ |
| 49 | (PS, R) | cyclopropyl | cyclopropylmethanesulfonylmethyl | thiophen-2-yl | $CF_3$ |
| 50 | (S, R) | tetrahydropyran-4-yl | cyclopropylmethanesulfonylmethyl | 4-Fphenyl | $CF_3$ |
| 51 | (S, R) | cyclopropyl | cyclopropylmethanesulfonylmethyl | 3,4-diF-phenyl | $CF_3$ |
| 52 | (S, R) | cyclopropyl | cyclopropylmethanesulfonylmethyl | 1-$CH_3$-pyrrol-2-yl | $CF_3$ |
| 53 | (S, R) | cyclopropyl | cyclopropylmethanesulfonylmethyl | 1-oxo-1-$CH_3$-pyrrol-2-yl | $CF_3$ |
| 54 | (S, R) | cyclopropyl | cyclopropylmethanesulfonylmethyl | 3,4,5-trifluoro-phenyl | $CF_3$ |
| 55 | (S, R) | cyclopropyl | 4-F-phenylmethanesulfonylmethyl | 4-F-phenyl | $CF_3$ |
| 56 | (S, R) | tetrahydrothio-pyran-4-yl | 4-F-phenylmethanesulfonylmethyl | 4-F-phenyl | $CF_3$ |
| 57 | (S, R) | cyclopropyl | 4-F-phenylmethanesulfonylmethyl | 3-phenoxyphenyl | $CF_3$ |
| 58 | (S, R) | 1,1-dioxohexa-hydro-1$\lambda^6$-thiopyran-4-yl | 4-F-phenylmethanesulfonylmethyl | 4-F-phenyl | $CF_3$ |
| 59 | (RS, R) | cyclopropyl | 2-$CHF_2$O-phenylmethanesulfonylmethyl | 1-phenylsulfonyl-pyrrol-2-yl | $CF_3$ |
| 60 | (S, R) | cyclopropyl | 2-$CHF_2$O-phenylmethanesulfonylmethyl | 4-F-phenyl | $CF_3$ |
| 61 | (RS, R) | cyclopropyl | 2-$CF_3$-pyridin-6-ylmethanesulfonyl-methyl | 4-F-pbenyl | $CF_3$ |
| 62 | (RS, R) | cyclopropyl | cyclopropylmethanesulfonylmethyl | 1-phenylsulfonyl-pyrrol-2-yl | $CF_3$ |
| 63 | (R, R) | cyclopropyl | pyrazin-2-ylmethanesulfonylmethyl | 4-F-phenyl | $CF_3$ |
| 64 | (S, R) | cyclopropyl | pyrazin-2-ylmethanesulfonylmethyl | 4-F-phenyl | $CF_3$ |
| 65 | (S, R) | tetrahydropyran-4-yl | 2-$CHF_2$O-phenylmethanesulfonylmethyl | 4-F-phenyl | $CF_3$ |
| 66 | (S, R) | 1,1-dioxohexa-hydro-1$\lambda^6$-thiopyran-4-yl | 2-$CHF_2$O-phenylmethanesulfonylmethyl | 4-F-phenyl | $CF_3$ |
| 67 | (S, R) | cyclopropyl | 2-$CF_3$-pyridin-6-ylmethanesulfonyl-methyl | 4-F-phenyl | $CF_3$ |
| 68 | (R,R) | cyclopropyl | pyrazin-2-ylmethanesulfanylmethyl | 4-F-phenyl | $CF_3$ |
| 69 | (S, R) | cyclopropyl | pyrazin-2-ylmethanesulfanylmethyl | 4-F-phenyl | $CF_3$ |
| 70 | (S,R) | cyclopropyl | 1-oxo-pyridin-2-ylmethanesulfonyl-methyl | 4-F-phenyl | $CF_3$ |

71. N-(1-Cyanocyclopropyl)-3-(pyridin-2-ylmethanesulfonyl)-2-(2,2,2-trifluoro-1-phenyl-1-trifluoromethylethylamino)-propionamide.

and are named as:

N-(1-cyanocyclopropyl)-3-phenylmethanesulfonyl-2(R)-(2,2,2-trifluoro-1(S)-phenylethylamino)propionamide;

N-(4-cyano-1-ethylpiperidin-4-yl)-3-phenylmethanesulfonyl-2(R)-(2,2,2-trifluoro-1(S)-phenyl-ethylamino)propionamide;

N-(4-cyano-1,1-dioxohexahydro-1$\lambda^6$-thiopyran-4-yl)-3-phenylmethanesulfonyl-2(R)-(2,2,2-trifluoro-1(S)-phenyl-ethylamino)propionamide;

N-(1-cyanocyclopropyl)-3-phenylmethanesulfanyl-2(R)-(2,2,2-trifluoro-1(S)-4-hydroxyphenylethylamino)propionamide;

N-(1-cyanocyclopropyl)-3-cyclopropylmethanesulfonyl-2(R)-(2,2,2-trifluoro-1(S)-phenylethyl-amino)propionamide;

N-(1-cyanocyclopropyl)-3-phenylmethanesulfanyl-2(R)-(2,2,2-trifluoro-1(RS)-furan-2-ylethylamino)propionamide;

N-(1-cyanocyclopropyl)-3-phenylmethanesulfonyl-2(R)-(2,2,2-trifluoro-1(RS)-furan-2-ylethylamino)propionamide;

N-(1-cyanocyclopropyl)-3-cyclopropylmethanesulfonyl-2(R)-(2,2,2-trifluoro-1(S)-3-bromophenylethylamino)propionamide;

N-(1-cyanocyclopropyl)-3-phenylmethanesulfanyl-2(R)-(2,2,2-trifluoro-1(RS)-indol-3-ylethylamino)propionamide;

N-(1-cyanocyclopropyl)-3-phenylmethanesulfonyl-2(R)-(2,2,2-trifluoro-1(RS)-indol-3ylethyl-amino)propionamide;

N-(1-cyanocyclopropyl)-3-phenylmethanesulfanyl-2(R)-(2,2,2-trifluoro-1(RS)-thiophen-2-yl-ethylamino)propionamide;

N-(1-cyanocyclopropyl)-3-phenylmethanesulfonyl-2(R)-(2,2,2-trifluoro-1(RS)-thiophen-2-yl-ethylamino)propionamide;

N-(1-cyanocyclopropyl)-3-cyclopropylmethanesulfonyl-2(R)-(2,2,2-trifluoro-1(S)-4-fluoro-phenylethylamino)propionamide;

N-(1-cyanocyclopropyl)-3-phenylmethanesulfonyl-2(R)-(2,2,2-trifluoro-1(S)-methylethyl-amino)propionamide;

N-(1-cyanocyclopropyl)-3-phenylmethanesulfonyl-2(R)-(2,2,2-trifluoro-1(S)-1-methylpyrrol-2-yl-ethylamino)propionamide;

N-(1-cyanocyclopropyl)-3-(1-methylcyclopentyl)-2(S)-(2,2,2-trifluoro-1(S)-thiophen-2-ylethylamino)propionamide;

N-(1-cyanocyclopropyl)-3-(1-methylcyclopentyl)-2(S)-(2,2,2-trifluoro-1(R)-thiophen-2-ylethylamino)propionamide;

N-(1-cyanocyclopropyl)-3-phenylmethanesulfonyl-2(R)-(2,2,2-trifluoro-1(S)-4-fluoro-phenylethylamino)propionamide;

N-(1-cyanocyclopropyl)-3-pyridin-2-ylmethanesulfanyl-2(R)-(2,2,2-trifluoro-1(RS)-phenylethylamino)propionamide;

N-(1-cyanocyclopropyl)-3-pyrdin-2-ylmethanesulfonyl-2(R)-(2,2,2-trifluoro-1(S)-phenylethyl-amino)propionamide;

N-(1-cyanocyclopropyl)-3-(1-methylcyclopentyl)-2(S)-(2,2,2-trifluoro-1(S)-2-hydroxy-phenylethylamino)propionamide;

N-(1-cyanocyclopropyl)-3-(1-methylcyclopentyl)-2(S)-(2,2,2-trifluoro-1(R)-4-hydroxy-phenyl-ethylamino)propionamide;

N-(1-cyanocyclopropyl)-3-pyridin-2-ylmethanesulfonyl-2(R)-(2,2,2-trifluoro-1(R)-phenylethylamino)propionamide;

N-(1-cyanocyclopropyl)-3-(1-methylcyclopentyl)-2(S)-(2,2,2-trifluoro-1(S)-4-hydroxy-phenylethylamino)propionamide;

N-(1-cyanocyclopropyl)-3-(2-chlorophenyl)-2(S)-(2,2,2-trifluoro-1(RS)-phenyl-ethylamino)propionamide;

N-(1-cyanocyclopropyl)-3-(2-chlorophenyl)-2(S)-(2,2,2-trifluoro-1(RS)-4-fluorophenyl-ethylamino)-propionamide;

N-(1-cyanocyclopropyl)-3-pyridin-2-ylmethanesulfonyl-2(R)-(2,2,2-trifluoro-1(RS)-4-fluoro-phenylethylamino) propionamide;

N-(1-cyanocyclopropyl)-3-phenylmethanesulfonyl-2(R)-(2,2,2-trifluoro-1(S)-4-hydroxyphenylethylamino)propionamide;

N-(1-cyanocyclopropyl)-3-phenylmethanesulfanyl-2(R)-(2,2,2-trifluoro-1(R)-3-chloro-4-hydroxy-phenylethylamino)propionamide;

N-(1-cyanocyclopropyl)-3-phenylmethanesulfanyl-2(R)-(2,2,2-trifluoro-1(S)-3-chloro-4-hydroxyphenylethylamino)propionamide;

N-(1-cyanocyclopropyl)-3-phenylmethanesulfonyl-2(R)-(2,2,2-trifluoro-1(R)-3-chloro-4-hydroxyphenylethylamino)propionamide;

N-(1-cyanocyclopropyl)-3-phenylmethanesulfonyl-2(R)-(2,2,2-trifluoro-1(S)-3-chloro-4-hydroxy-phenylethylamino)propionamide;

N-(1-cyanocyclopropyl)-3-(1-methylcyclopentyl)-2(S)-(2,2-difluoro-1(R)-thiophen-2-ylethylamino)propionamide;

N-(1-cyanocyclopropyl)-3-phenylmethanesulfanyl-2(R)-(2,2-difluoro-1(RS)-thiophen-2-yl-ethylamino)propionamide;

N-(1-cyanocyclopropyl)-3-(1-methylcyclopentyl)-2(S)-(2,2,2-trifluoro-1(S)-3-fluoro-4-hydroxyphenylethylamino)propionamide;

N-(1-cyanocyclopropyl)-3-phenylmethanesulfanyl-2(R)-(2,2,2-trifluoro-1(RS)-pyridin-2-yl-ethylamino)propionamide;

N-(1-cyanocyclopropyl)-4-pyridin-2-ylsulfanyl-2(S)-(2,2,2-trifluoro-1(RS)-4-fluoro-phenylethylamino)butyramide;

N-(1-cyanocyclopropyl)-4-pyridin-2-ylsulfonyl-2(S)-(2,2,2-trifluoro-1(RS)-4-fluoro-phenyl-ethylamino)butyramide;

N-(1-cyanocyclopropyl)-3-phenylmethanesulfonyl-2(R)-(2,2,2-trifluoro-1(RS)-pyridin-2-yl-ethylamino)propionamide;

N-(1-cyanocyclopropyl)-3-phenylmethanesulfonyl-2(R)-(2,2-difluoro-1(R)-thiophen-2-ylethylamino)propionamide;

N-(1-cyanocyclopropyl)-3-(2-difluoromethoxyphenyl-methanesulfanyl)-2(R)-(2,2,2-trifluoro-1(RS)-thiophen-2-ylethylamino)propionamide;

N-(1-cyanocyclopropyl)-3-(2-difluoromethoxyphenyl-methanesulfonyl)-2(R)-(2,2,2-trifluoro-1(RS)-thiophen-2-ylethylamino)propionamide;

N-(1-cyanocyclopropyl)-3-pyridin-2-ylmethanesulfanyl-2(R)-(2,2,2-trifluoro-(S)-4-fluoro-phenylethylamino)propionamide;

N-(1-cyanocyclopropyl)-3-pyridin-2-ylmethanesulfonyl-2(R)-(2,2,2-trifluoro-1(S)-4-fluorophenylethylamino)propionamide;

N-(1-cyanocyclopropyl)-3 -pyridin-2-ylmethanesulfanyl-2(R)-(2,2,2-trifluoro-1(R)-4-fluorophenylethylamino)propionamide;

N-(1-cyanocyclopropyl)-3 -pyridin-2-ylmethanesulfonyl-2(R)-(2,2,2-trifluoro-1(R)-4-fluorophenylethylamino)propionamide;

N-(1-cyanocyclopropyl)-3-cyclopropylmethanesulfonyl-2(R)-(2,2,2-trifluoro-1(S)-thiophen-3-ylethylamino)propionamide;

N-(1-cyanocyclopropyl)-3-cyclopropylmethanesulfanyl-2(R)-(2,2,2-trifluoro-1(RS)-thiophen-2-ylethylamino)propionamide;

N-(1-cyanocyclopropyl)-3-cyclopropylmethanesulfonyl-2(R)-(2,2,2-trifluoro-1(RS)-thiophen-2-ylethylamino)propionamide;

N-(1-cyanotetrahydropyran-4-yl)-3-cyclopropylmethanesulfonyl-2(R)-(2,2,2-trifluoro-1(S)-4-fluorophenylethylamino)propionamide;

N-(1-cyanocyclopropyl)-3-cyclopropylmethanesulfonyl-2(R)-(2,2,2-trifluoro-1(S)-3,4-difluoro-phenylethylamino)propionamide;

N-(1-cyanocyclopropyl)-3-cyclopropylmethanesulfonyl-2(R)-(2,2,2-trifluoro-1(S)-1-methylpyrrol-2-ylethylamino)propionamide;

N-(1-cyanocyclopropyl)-3-cyclopropylmethanesulfonyl-2(R)-(2,2,2-trifluoro-1(S)-1-oxo-1-methyl-pyrrol-2-ylethylamino)propionamide;

N-(1-cyanocyclopropyl)-3-cyclopropylmethanesulfonyl-2(R)-(2,2,2-trifluoro-1(S)-3,4,5-trifluoro-phenylethylamino)propionamide;

N-(1-cyanocyclopropyl)-3-(4-fluorophenylmethanesulfonyl)-2(R)-(2,2,2-trifluoro-1(S)-4-fluoro-phenylethylamino)propionamide;

N-(1-cyanotetrahydrothiopyran-4-yl)-3-(4-fluorophenyl-methanesulfonyl)-2(R)-(2,2,2-trifluoro-1(S)-4-fluorophenyl-ethylamino)propionamide;

N-(1-cyanocyclopropyl)-3-(4-fluorophenylmethanesulfonyl)-2(R)-(2,2,2-trifluoro-1(S)-3-phenoxy-phenylethylamino)propionamide;

N-(1-cyano-1,1-dioxohexahydro-1λ⁶-thiopyran-4-yl)-3-(4-fluorophenylmethane-sulfonyl)-2(R)-(2,2,2-trifluoro-1(S)-4-fluorophenylethylamino)propionamide;

N-(1-cyanocyclopropyl)-3-(2-difluoromethoxyphenyl-methanesulfonyl)-2(R)-(2,2,2-trifluoro-1(RS)-1-phenylsulfonylpyrrol-2-ylethylamino)propionamide;

N-(1-cyanocyclopropyl)-3-(2-difluoromethoxyphenyl-methanesulfonyl)-2(R)-(2,2,2-trifluoro-1(S)-4-fluorophenyl-ethylamino)propionamide;

N-(1-cyanocyclopropyl)-3-(2-trifluoromethylpyridin-6-ylmethanesulfonyl)-2(R)-(2,2,2-trifluoro-1(RS)-4-fluorophenyl-ethylamino)propionamide;

N-(1-cyanocyclopropyl)-3-cyclopropylmethanesulfonyl-2(R)-(2,2,2-trifluoro-1(RS)-1-phenyl-sulfonylpyrrol-2-yl-ethylamino)propionamide;

N-(1-cyanocyclopropyl)-3-pyrazin-2-ylmethanesulfonyl-2(R)-(2,2,2-trifluoro-1(R)-4-fluorophenyl-ethylamino)propionamide;

N-(1-cyanocyclopropyl)-3-pyrazin-2-ylmethanesulfonyl-2(R)-(2,2,2-trifluoro-1(S)-4-fluorophenyl-ethylamino)propionamide;

N-(1-cyanotetrahydropyran-4-yl)-3-(2-difluoromethoxyphenylmethanesulfonyl)-2(R)-(2,2,2-trifluoro-1(S)-4-fluorophenylethylamino)propionamide;

N-(1-cyano1,1-dioxohexahydro-1λ⁶-thiopyran-4-yl)-3-(2-difluoromethoxyphenyl-methanesulfonyl)-2(R)-(2,2,2-trifluoro-1(S)-4-fluorophenylethylamino)propionamide;

N-(1-cyanocyclopropyl)-3-(2-trifluoromethylpyridin-6-ylmethanesulfonyl)-2(R)-(2,2,2-trifluoro-1(S)-4-fluorophenyl-ethylamino)propionamide;

N-(1-cyanocyclopropyl)-3-pyrazin-2-ylmethanesulfanyl-2(R)-(2,2,2-trifluoro-1(R)-4-fluorophenyl-ethylamino)propionamide;

N-(1-cyanocyclopropyl)-3-pyrazin-2-ylmethanesulfanyl-2(R)-(2,2,2-trifluoro-1(S)-4-fluorophenyl-ethylamino)propionamide;

N-(1-cyanocyclopropyl)-3-(1-oxopyridin-2-ylmethanesulfonyl)-2(R)-(2,2,2-trifluoro-1(S)-4-fluorophenyl-ethylamino)propionamide; and N-(1-cyanocyclopropyl)-3-(pyridin-2-ylmethanesulfonyl)-2-(2,2,2-trifluoro-1-phenyl-1-trifluoromethylethylamino)-propionamide.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1999.

Compounds of Formula (I) where $R^1$, $R^2$, $R^3$, $R^4$, $R^5$, $R^6$, and $R^7$ are as defined in the Summary of the Invention and $R^8$ is hydrogen can be prepared by proceeding as in the following Reaction Scheme 1 below.

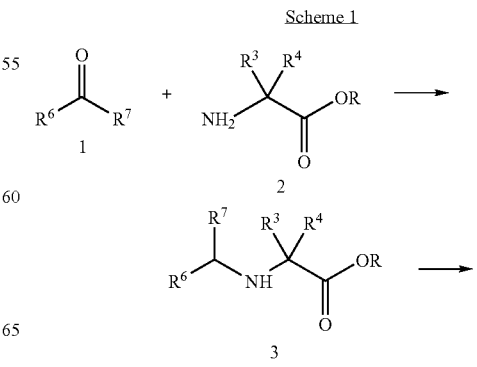

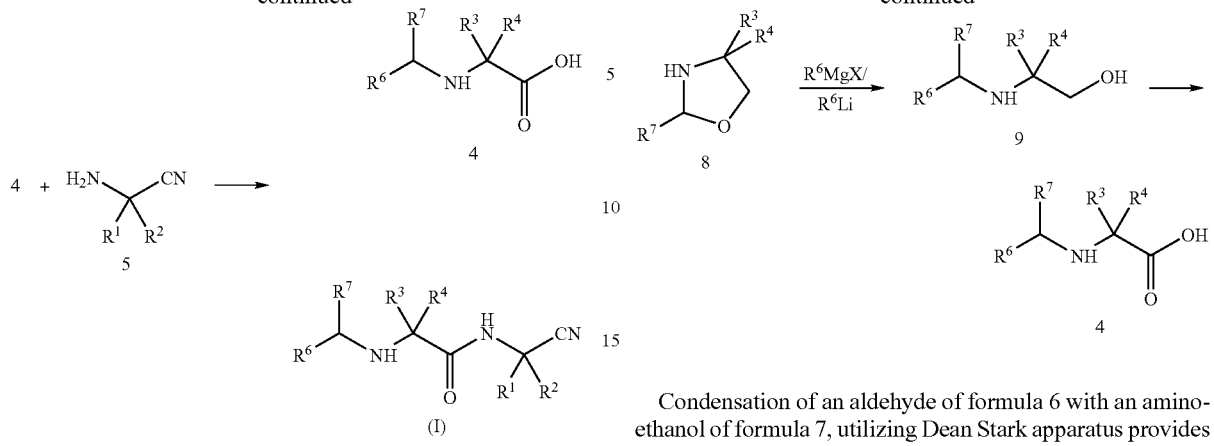

Reaction of a ketone of formula 1 where $R^6$ is as defined in the Summary of the Invention and $R^7$ is a haloalkyl (preferably trifluoromethyl) with an α-amino ester of formula 2 where R is a carboxy protecting group, preferably an alkyl group, preferably methyl, and $R^3$ and $R^4$ are as defined in the Summary of the Invention under reductive amination reaction conditions provide a compound of formula 3. The reaction is carried out in the presence of a suitable dehydrating agent such as $TiCl_4$, magnesium sulfate, isopropyl trifluoroacetate, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, ethanol, and the like.

Compounds of formula 1 such as 2,2,2-trifluoromethylacetophenone and 2,2,2-trifluoromethyl-4-phenylphenylethanone are commercially available. Others can be prepared by methods well known in the art. α-Amino esters of formula 2 of alanine, cysteine, aspartic acid, glutamic acid, phenylalanine, histidine, and lysine are commercially available. Others can be prepared by methods well known in the art. Some such methods are described in PCT Applications Publication Nos. WO 03075836, WO 00/55144, WO 01/19816, WO 02/20485, WO 03/029200, U.S. Provisional Application No. 60/422, 337, U.S. Pat. No. 6,353,017B1, 6,492,662B1, 353,017 B1 and 6,525,036B1, 6,229,011B1, 6,610,700, the disclosures of which are incorporated herein by reference in their entirety.

Hydrolysis of the ester group provides a compound of formula 4. The hydrolysis conditions depend on the nature of the protecting group. For example, when R is alkyl the hydrolysis is carried out under aqueous basic hydrolysis reaction conditions to give the corresponding acid of formula 4. The reaction is typically carried out with cesium carbonate, lithium hydroxide, and the like in an aqueous alcohol such as methanol, ethanol, and the like.

Alternatively, compounds of formula 4 can be prepared as shown below in Method (i) below.

Method (i)

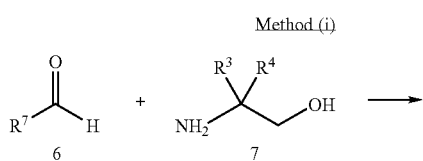

Condensation of an aldehyde of formula 6 with an aminoethanol of formula 7, utilizing Dean Stark apparatus provides a cyclic aminal of formula 8 which upon reaction with a Grignard reagent of formula $R^6MgX$ (where X is halo) or an organolithium reagent of formula $R^6Li$ provides a compound of formula 9. Oxidation of 9 with a suitable oxidizing agent such as Jones oxidizing reagent or $H_5IO_6/CrO_3$, and the like, then provides a compound of formula 4. Compound 7 can be prepared by reducing a compound of formula 2 where R is hydrogen with a suitable reducing agent such as lithium aluminum hydride, and the like under conditions well known in the art.

Compound 4 is then reacted with an α-aminoacetonitrile of formula 5 to give a compound of Formula (I). The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 4 into an active acid derivative such as succinimide ester and then reacting it with an amine of formula 5. The reaction typically requires 2 to 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

The above method can also be used to prepared compounds of Formula (I) where $R^8$ is other than hydrogen utilizing the procedure described in method (i) above, by substituting $R^6COH$ with a ketone of formula $R^6R^7CO$ and then treating the resulting cyclic aminal with $R^8Li/R^8MgX$, followed by oxidation to give the free acid. The free acid is then condensed with 5 under conditions described above to give compound (I).

It will be apparent to a person skilled in the art, that compounds of Formula (I) can also be prepared by first condensing 5 with the N-protected amino acid of formula 2 where R is hydrogen followed by removal of the amino protecting group and reacting the free amino compound with a compound of formula 1 as described in Scheme 1 above. Suitable amino acid protecting groups and reaction conditions for putting them on and removing them can be found in Greene, T. W.; and Wuts, P. G. M.; *Protecting Groups in Organic Synthesis;* John Wiley & Sons, Inc. 1999.

Alternatively, a compound of Formula (I) can be prepared as illustrated and described in Scheme 2 below.

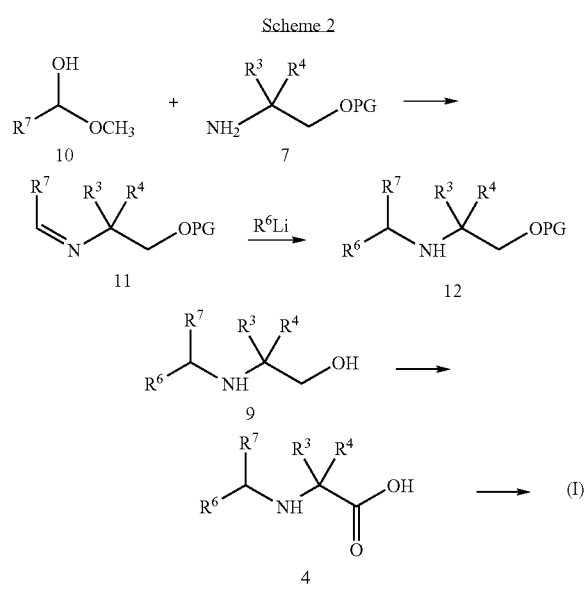

Reaction of a compound of formula 7 where $R^3$ and $R^4$ are as defined in the Summary of the Invention and PG is a suitable oxygen protecting group with a hemiacetal of formula 10 where $R^7$ is as defined in the Summary of the Invention provides an imine compound of of formula 11. Treatment of 11 with an organic lithium compound of formula $R^6Li$ where $R^6$ is as defined in the Summary of the Invention provides compound 12. Removal of the oxygen protecting group, followed by oxidation of the resulting alcohol 9 provides a compound of formula 4 which is then converted to a compound of Formula (I) as described in Scheme 1 above. Suitable oxygen protecting groups and reaction conditions for putting them on and removing them can be found in Greene, T. W.; and Wuts, P. G. M.; *Protecting Groups in Organic Synthesis;* John Wiley & Sons, Inc. 1999.

Alternatively, a compound of Formula (I) where $R^6$ is aryl or heteroaryl can be prepared as illustrated and described in Scheme 3 below.

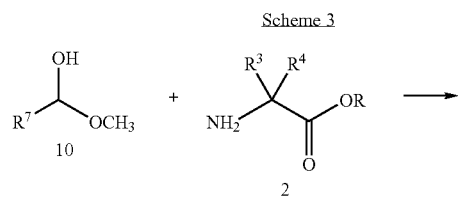

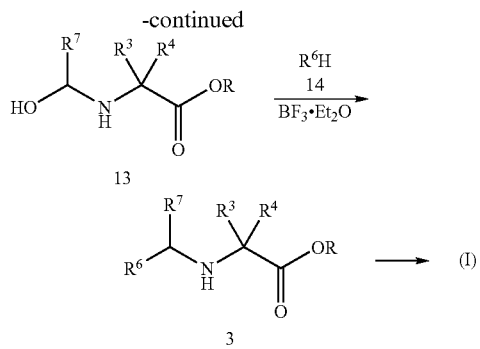

Reaction of a compound of formula 2 where R is alkyl and $R^3$ and $R^4$ are as defined in the Summary of the Invention with a hemiacetal compound of formula 10 where $R^7$ is as defined in the Summary of the Invention provides a 2-(1-hydroxymethylamino)acetate compound of formula 13. The reaction is carried out in the presence of a catalytic amount of an acid such as p-toluenesulfonic acid and in an aromatic hydrocarbon solvent such as toluene, benzene, and the like.

Treatment of 13 with a compound of formula 14 which is an aryl or heteroaryl ring under Friedel-Crafts reaction conditions provides a compound of formula 3 which is then converted to a compound of Formula (I) as described above.

Alternatively, a compound of Formula (I) can be prepared as illustrated and described in Scheme 4 below.

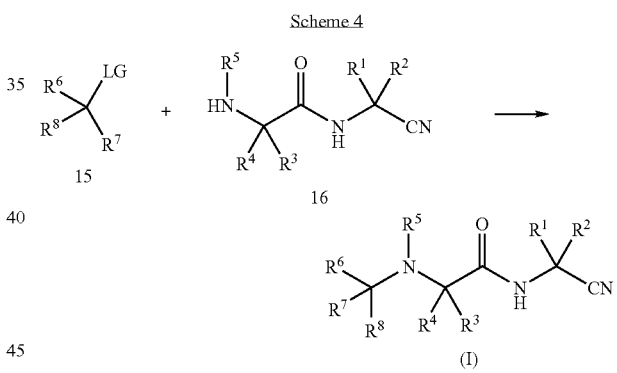

Reaction of a compound of formula 15 where LG is a suitable leaving group such as trifluoromethansulfonate, and the like, and $R^6$, $R^7$, and $R^8$ are as defined in Summary of the Invention with a compound of formula 16 where $R^1$-$R^5$ are as defined in the Summary of the Invention provides a compound of Formula (I). The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Preferably, the reaction is carried out at room temperature.

Compounds of formula 15 can be prepared by methods well known in the art. For example, a compound of formula 15 where $R^6$ is phenyl or 4-fluorophenyl, $R^7$ is trifluoromethyl, and $R^8$ is hydrogen can be readily prepared from commercially available 2,2,2-trifluoroacetophenone or 2,2,2,4'-tetrafluoroacetophenone respectively, by reducing the keto group to an alcoholic group by suitable reducing agent such as sodium borohydride, lithium aluminum hydride, and the like. The solvent used depends on the type of reducing agent. For example, when sodium borohydride is used the reaction is carried out in an alcoholic organic solvent such as methanol, ethanol, and the like. When lithium aluminum hydride is used the reaction is carried out in an ethereal solvent such as tetrahydrofuran, and the like. Reaction of 2,2,2-trifluoro-1-phenylethanol or 2,2,2-trifluoro-1-(4-fluorophenyl)ethanol with triflic anhydride provides the desired compound.

Optically enriched compound of formula 15 can be obtained by reduction of the corresponding halogenated acetophenone with a suitable reducing agent such as catecholborane or $BH_3$-DMS complex in the presence of a suitable catalyst such as (S) or (R)-CBS catalyst or (S) or (R)-α, α-diphenyl-2-pyrrolidine-methanol in the presence of BBN to provide chiral alcohol which is then converted to compound (a) as described above. Compounds of formula 16 can be prepared by reacting a compound of formula 2 where R is hydrogen with a compound of formula 5 as described in Scheme 1 above.

Alternatively, the compound of Formula (I) can be prepared as illustrated and described in Scheme 5 below.

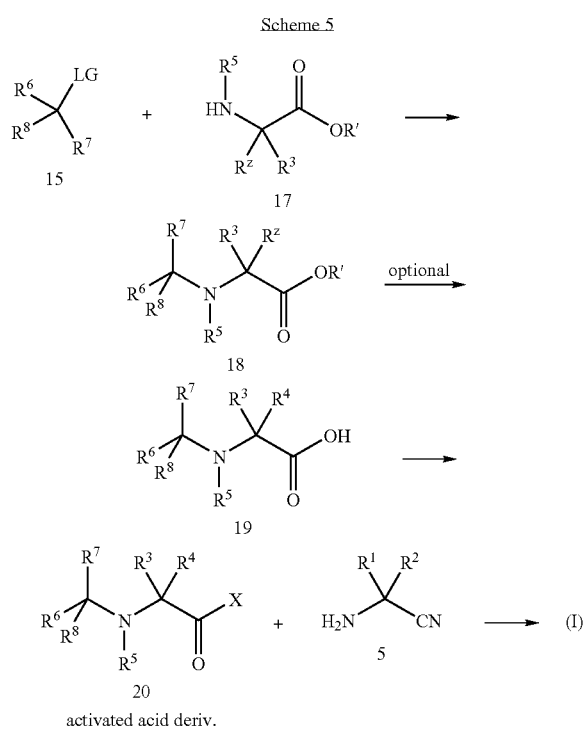

activated acid deriv.

Reaction of a compound of formula 15 where LG is a suitable leaving group such as trifluoromethansulfonate, and the like, and $R^6$, $R^7$, and $R^8$ are as defined in Summary of the Invention with a compound of formula 17 where $R^5$ is as defined in the Summary of the Invention, preferably hydrogen, $R^3$ is as defined in the Summary of the Invention, $R^Z$ is $R^4$ as defined in the Summary of the Invention or -(alkylene)-$X^1$-Z where $X^1$ is as defined in the Summary of the Invention and Z is a protecting group e.g., trityl, and the like, and R' is hydrogen or a suitable carboxy protecting group such as alkyl, and the like, under the reaction conditions described in Scheme 4 above, provides a compound of formula 18. Other suitable carboxy protecting and Z protecting groups and reaction conditions for putting them on and removing them can be found in Greene, T. W.; and Wuts, P. G. M.; *Protecting Groups in Organic Synthesis;* John Wiley & Sons, Inc. 1999, the disclosure of which is incorporated herein by reference in its entirety.

A compound of formula 18 where $R^Z$ is -(alkylene)-$X^1$-Z can be converted to a corresponding compound of formula 18 where $R^4$ is -(alkylene)-$X^1$—$R^{22}$ where $R^{22}$ is as defined in the Summary of the invention by methods well known in the art. For example, a compound of formula 18 where $X^1$ is —$S(O)_{n3}$— where n3 is 0-2 and $R^Z$ is trityl protecting group can be easily converted to a corresponding compound of formula 18 where $R^Z$ is $R^4$ where $R^4$ is -(alkylene)-$S(O)_{n3}$—$R^{22}$ where $R^{22}$ is alkyl, cycloalkylalkyl, heterocyclylalkyl, aralkyl or heteroaralkyl by removing the trityl group and reacting the resulting thiol group with suitable alkylating agent of the formula $R^{22}$LG where LG is a leaving group such as halo, tosylate, mesylate, triflate, and the like, in the presence of a base and optionally oxidizing the sulfur atom to sulfoxide or sulfone with an oxidizing agent such as OXONE®, and the like.

Similarly, other compounds of formula 18 where $R^Z$ is $R^4$ where $R^4$ is -(alkylene)-$X^1$—$R^{22}$ where $X^1$ is —$NR^{23}$—, —O—, —$S(O)_{n3}$—, —CO—, —COO—, —OCO—, —$NR^{23}$CO—, —$CONR^{23}$—, —$NR^{23}SO_2$—, —$SO_2NR^{23}$—, —$NR^{23}$COO—, —$OCOONR^{23}$—, —$NR^{23}CONR^{24}$—, or —$NR^{23}SO_2NR^{24}$— where $R^{22}$, $R^{23}$ and $R^{24}$ are as defined in the Summary of the Invention can be prepared from commercially available compound of formula 17 such as lysine, glutamic acid, aspartic acid, serine, and homoserine by methods well known in the art. Some such methods are described in U.S. Pat. No. 6,136,844 the disclosure of which is incorporated herein by reference in its entirety.

Compounds of formula 17 are either commercially available or they can be prepared by methods well known in the art. For example, alanine, cysteine, aspartic acid, glutamic acid, phenylalanine, histidine, and lysine are commercially available. Others can be prepared by methods well known in the art. Some such methods are described in PCT Applications Publication Nos. WO 03/075836, WO 00/55144, WO 01/19816, WO 02/20485, WO 03/029200, U.S. Provisional Application No. 60/422,337, U.S. Pat. Nos. 6,353,017B1, 6,492,662B1, 353,017 B1 and 6,525,036B1, 6,229,011B1, 6,610,700, the disclosures of which are incorporated herein by reference in their entirety.

Removal of the carboxy protecting group from a compound of formula 18 where R' is a protecting group provides a compound of formula 19. The conditions used to remove the carboxy protecting group depend on the nature of the carboxy protecting group. For example, if R' is alkyl, it is removed under basic hydrolysis reaction conditions utilizing aqueous base such as aqueous lithium hydroxide, sodium hydroxide, and the like in an alcoholic solvent such as methanol, ethanol, and the like.

Compound 19 is then converted to an activated acid derivative 20 (X is a leaving group) and which upon reaction with an aminoacetonitrile compound of formula 5 provides a compound of Formula (I). The activated acid derivative can be prepared and then reacted with compound 5 in a stepwise manner or the acid derivative can be generated in situ in the presence of compound 5. For example, if the activated acid is acid halide it is first prepared by reacting 19 with a halogenating agent such as thionyl chloride, oxalyl, chloride and the like and then reacted with compound 5.

Alternatively, the activated acid derivative is generated in situ by reacting compound 19 and 5 in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Alternatively, the activated acid can be reacted with $CR^1R^2(NH_2)CONH_2$ where $R^1$ and $R^2$ are as described in the Summary of the Invention, followed by conversion of the —$CONH_2$ group to the cyano group by methods well known in the art.

Alternatively, the compound of Formula (I) can be prepared as illustrated and described in Scheme 6 below.

protecting group can be found in Greene, T. W.; and Wuts, P. G. M.; *Protecting Groups in Organic Synthesis;* John Wiley & Sons, Inc. 1999.

Compounds 22 where R" is hydrogen and 23 are then converted to a compound of formula 24 utilizing a suitable oxidizing agent such as Jones oxidizing reagent, $H_5IO_6/CrO_3$, and the like. Compound 24 is then converted to a compound of Formula (I) as described above.

A compound of Formula (I) can be converted to other compounds of Formula (I). For example:

A compound of Formula (I) where $R^6$ is an aromatic ring substituted with halo can be reacted with appropriated boronic acid under palladium catalyzed Suzuki coupling reaction conditions to provide a correspond compound of Formula (I) where $R^6$ is further substituted with an aryl or heteroaryl ring.

A compound of Formula (1) containing a hydroxy group may be prepared by de-alkylation/benzylation of an alkoxylbenzyloxy substituent; those containing an acid group, by hydrolysis of an ester group; and those containing a cyano, by displacement of a bromine atom on the corresponding compounds of Formula (I). A compound of Formula (I) containing a halo group such as chloro can be converted to a corre-

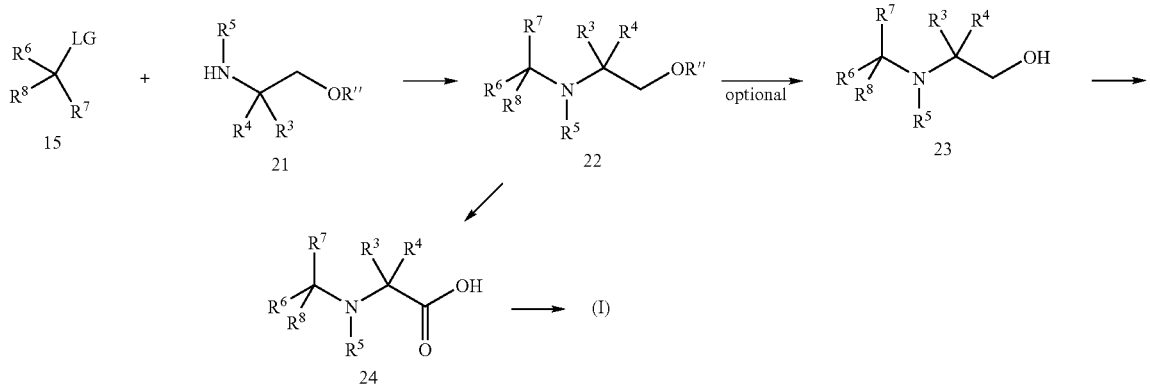

Scheme 6

Reaction of a compound of formula 15 where LG is a suitable leaving group such as trifluoromethansulfonate, and the like, and $R^6$, $R^7$, and $R^8$ are as defined in Summary of the Invention with a compound of formula 21 where $R^3$-$R^8$ are as defined in the Summary of the Invention and R" is a suitable hydroxyl protecting group such as trialkylsilyl, and the like, under the reaction conditions described in Scheme 4 above, provides a compound of formula 22. Suitable hydroxy protecting groups and reaction conditions for putting them on and removing them can be found in Greene, T. W.; and Wuts, P. G. M.; *Protecting Groups in Organic Synthesis;* John Wiley & Sons, Inc. 1999. Compounds of formula 21 can be prepared from corresponding natural and unnatural amino acids by methods well known in the art. Some such procedures are described in PCT Application Publication No. WO 03/075836, the disclosure of which is incorporated herein by reference in its entirety.

Compound 22 where R" is a hydroxy protecting group is then converted to a corresponding compound of formula 23 where R" is hydrogen by removal of the hydroxyl protecting group. Suitable reaction conditions for removing hydroxy sponding compound of Formula (I) containing an methylthio by treating it with sodium thiomethoxide. The methylthio group can be oxidized to methylsulfonyl using a suitable oxidizing agent such as OXONE®. A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

Preparation of Biological Agents

In practicing this invention several processes for the generation or purification of biological agents are used. Methods for preparing the biologics are well known in the art as discussed below.

Monoclonal antibodies are prepared using standard techniques, well known in the art, such as by the method of Kohler and Milstein, *Nature* 1975, 256:495, or a modification thereof, such as described by Buck et al. 1982, *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

Chimeric antibodies composed of human and non-human amino acid sequences may be formed from the mouse monoclonal antibody molecules to reduce their immunogenicity in humans (Winter et al. *Nature* 1991 349:293; Lobuglio et al. *Proc. Nat. Acad. Sci.* USA 1989 86:4220; Shaw et al. *J. Immunol.* 1987 138:4534; and Brown et al. *Cancer Res.* 1987 47:3577; Riechmann et al. *Nature* 1988 332:323; Verhoeyen et al. *Science* 1988 239:1534; and Jones et al. *Nature* 1986 321:522; EP Publication No.519,596, published Dec. 23, 1992; and U.K. Patent Publication No. GB 2,276,169, published Sep. 21, 1994).

Antibody molecule fragments, e.g., F(ab').sub.2, FV, and sFv molecules, that are capable of exhibiting immunological binding properties of the parent monoclonal antibody molecule can be produced using known techniques. Inbar et al. *Proc. Nat. Acad. Sci.* USA 1972 69:2659; Hochman et al. *Biochem.* 1976 15:2706; Ehrlich et al. *Biochem.* 1980 19:4091; Huston et al. *Proc. Nat. Acad. Sci.* USA 1988 85(16):5879; and U.S. Pat. Nos. 5,091,513 and 5,132,405, and U.S. Pat. No. 4,946,778.

In the alternative, a phage-display system can be used to expand the monoclonal antibody molecule populations in vitro. Saiki, et al. *Nature* 1986 324:163; Scharf et al. *Science* 1986 233:1076; U.S. Pat. Nos. 4,683,195 and 4,683,202; Yang et al. *J. Mol. Biol.* 1995 254:392; Barbas, III et al. *Methods: Comp. Meth Enzymol.* 1995 8:94; Barbas, III et al. *Proc. Natl. Acad. Sci.* USA 1991 88:7978.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. *Nature* 1978 275:615, Goeddel et al. *Nature* 1979 281:544, Goeddel et al. *Nucleic Acids Res.* 1980 8:4057, European Application No. EP 36,776, U.S. Pat. No. 4,551,433, deBoer et al. *Proc. Natl. Acad. Sci.* USA 1983 80:21-25, and Siebenlist et al. *Cell* 1980 20:269.

Expression systems in yeast include those described in Hinnen et al. *Proc. Natl. Acad. Sci.* USA 1978 75:1929, Ito et al. *J. Bacteriol.* 1983 153:163, Kurtz et al. *Mol. Cell. Biol.* 1986 6:142, Kunze et al. *J. Basic Microbiol.* 1985 25:141, Gleeson et al. *J. Gen. Microbiol.* 1986 132:3459, Roggenkamp et al. *Mol. Gen. Genet.* 1986 202:302, Das et al. *J. Bacteriol.* 1984 158:1165, De Louvencourt et al. *J. Bacteriol.* 1983 154:737, Van den Berg et al. *Bio/Technology* 1990 8:135, Kunze et al. *J. Basic Microbiol.* 1985 25:141, Cregg et al. *Mol. Cell. Biol.* 1985 5:3376, U.S. Pat. Nos. 4,837,148 and 4,929,555, Beach et al. *Nature* 1981 300:706, Davidow et al. *Curr. Genet.* 1985 10:380, Gaillardin et al. *Curr. Genet.* 1985 10:49, Ballance et al. *Biochem. Biophys. Res. Commun.* 1983 112:284-289, Tilburn et al. *Gene* 1983 26:205-221, Yelton et al. *Proc. Natl. Acad. Sci.* USA 1984 81:1470-1474, Kelly et al. *EMBO J.* 1985 4:475479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. *J. Gen. Virol.* 1988 69:765-776, Miller et al. *Ann. Rev. Microbiol.* 1988 42:177, Carbonell et al. *Gene* 1988 73:409, Maeda et al. *Nature* 1985 315:592-594, Lebacq-Verheyden et al. *Mol. Cell. Biol.* 1988 8:3129, Smith et al. *Proc. Natl. Acad. Sci.* USA 1985 82:8404, Miyajima et al. *Gene* 1987 58:273, and Martin et al. *DNA* 1988 7:99. Numerous baculoviral strains and variants and corresponding permissive insect host cells from hosts are described in Luckow et al. *Bio/Technology* 1988 6:47-55, Miller et al. *GENETIC ENGINEERING*, Setlow, J. K. et al. eds., Vol. 8, Plenum Publishing, pp. 1986 277-279, and Maeda et al. *Nature* 1985 315:592-594.

Mammalian expression can be accomplished as described in Dijkema et al. *EMBO J.* 1985 4:761, Gorman et al. *Proc. Natl. Acad Sci.* USA 1982 79:6777, Boshart et al. *Cell* 1985 41:521, and U.S. Pat. No. 4,399,216. Other features of mammalian expression can be facilitated as described in Ham et al. *Meth. Enz.* 1979 58:44, Barnes et al. *Anal. Biochem.* 1980 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195.

The production of recombinant adenoviral vectors are described in U.S. Pat. No. 6,485,958. Botulinum toxin type A can be obtained by establishing and growing cultures of *Clostridium botulinum* in a fermenter and then harvesting and purifying the fermented mixture in accordance with known procedures. Any of the above-described protein production methods can be used to provide the biologic that would benefit from the present invention.

Pharmacology And Utility

The compounds of the invention are selective inhibitors of cysteine proteases such as cathepsin S, K, B, and/or F, and in particular cathepsin S, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1-5, infra.

Administration And Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described in Example 1 below.

EXAMPLES

The present invention is further exemplified, but not limited by, the following examples that illustrate the preparation of compounds of Formula (I) (Examples) and intermediates (References) according to the invention.

Example A

Synthesis of 2(RS)-benzyloxycarbonylamino-4(RS)-(2-methoxyphenyl)pentanoic acid

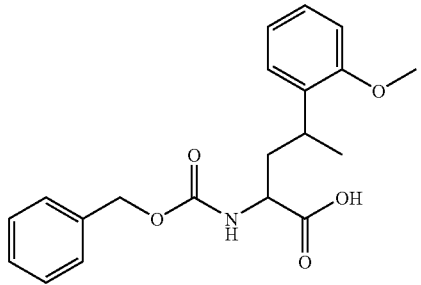

To d,l-2-methoxy-α-methylbenzyl alcohol (0.5 g, 3.29 mmol) was added 48% aq. HBr (2 mL) and the reaction mixture was stirred rapidly for 1.5 h. The reaction mixture was diluted with hexane (30 mL), washed with water, dried with $MgSO_4$, filtered, and evaporated under vacuum. The crude d,l-2-methoxy-α-methylbenzyl bromide was added to a solution of tributyltin hydride (0.67 mL, 2.49 mmol), Z-dehydroalanine methyl ester (0.25 g, 1.06 mmol), and 2,2'-azobisisobutyronitrile (15 mg, 0.09 mmol) in benzene (5 mL). The reaction mixture was heated at 80° C. under a nitrogen atmosphere for 5 h. Benzene was removed under vacuum and the residue was dissolved in methanol (20 mL). 2N KOH (5 mL) was added and the mixture was rapidly stirred at room temperature over night. Methanol was removed under vacuum and the residue was diluted with water (20 mL). The aqueous solution was washed with ether to remove the tin by products. The aqueous layer was acidified with 6 N HCl (aq.) and the product was extracted with ethyl acetate. The combined organic layers were washed with brine, dried with $MgSO_4$, filtered, and evaporated under vacuum to give 2-benzyloxy-carbonylamino-4-(2-methoxyphenyl)pentanoic acid (190 mg, 0.53 mmol) as a mixture of diastereomers in sufficiently pure form to be used without further purification. MS: $(M^++H)$ 358, $(M^+-H)$ 356.

Following the procedure described above, and utilizing appropriate starting materials the following amino acids were prepared:

2-benzyloxy-carbonylamino-4-(2-methoxyphenyl)hexanoic acid;

2-benzyloxy-carbonylamino-4-(4-fluorophenyl)pentanoic acid;

2-benzyloxy-carbonylamino-4-(4-chlorophenyl)pentanoic acid;

2-benzyloxy-carbonylamino-4-(4-methoxyphenyl)pentanoic acid;

2-benzyloxy-carbonylamino-4-(2-trifluoromethylphenyl)pentanoic acid;

2-benzyloxy-carbonylamino-4-(3-trifluoromethylphenyl)pentanoic acid;

2-benzyloxy-carbonylamino-4-(napth-1-yl)pentanoic acid;

2-benzyloxy-carbonylamino-4-(2,6-dimethylphenyl)pentanoic acid;

2-benzyloxy-carbonylamino-4-(2,4-difluorophenyl)pentanoic acid;

2-benzyloxy-carbonylamino-4-(2,4-dimethylphenyl)pentanoic acid;

2-benzyloxy-carbonylamino-4-(2,5-dimethylphenyl)pentanoic acid; and 2-benzyloxy-carbonylamino-4-(2,4-dichlorophenyl)pentanoic acid.

The benzyloxycarbonyl group can be removed as described in Example B below to give the corresponding free amino acid.

Example B

Synthesis of 2(S)-2,6-difluorophenylalanine

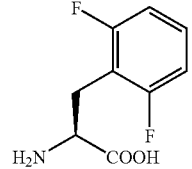

Step 1

N-(Benzyloxycarbonyl)-α-phosphonoglycine trimethyl ester (Aldrich No. 37,635-3; 6.7 g, 20 mmol) and 1,8-diazabicyclo[5,4,0]undec-7-ene (Aldrich No. 13, 900-9; 3.3 mL, 22 mmol) were dissolved in methylene chloride (11 mL) and stirred at room temperature for 15 min, and then cooled to <–30° C. A solution of 2,6-difluorobenzaldehyde (1.9 mL, 20 mmol) in methylene chloride (25 mL) was added to the reaction mixture dropwise over 20 min. The reaction mixture was stirred for another 20 min, and then allowed to warm up to room temperature for 30 min. The reaction mixture was then poured into ethyl ether (300 mL) and washed with 1 N HCl, brine and dried over $MgSO_4$. Rotary evaporation gave crude 2-benzyloxycarbonylamino-3-(2,6-difluorophenyl)acrylic acid methyl ester which was purified by chromatography on a Medium Pressure Liquid Column (MPLC) eluting with 20% ethyl acetate/80% hexane to give pure product (5 g, 72% yield, liquid).

Step 2

A mixture of 2-benzyloxycarbonylamino-3-(2,6-difluorophenyl)acrylic acid methyl ester (14.4 mmol), and catalyst, (+)-1,2-bis-[(2S, 5S)2,5-diethylphopholano]benzene (cyclooctadiene)rhodium (1) trifluoromethanesulfonate (Strem. Chemical No. 45-0151; 104 mg, 0.14 mmol) was dissolved in ethanol (150 mL). Hydrogenation was performed at 50 psi $H_2$ at room temperature over 2 days. The solvent was then removed by rotary evaporation to give 2(S)-benzyloxycarbonylamino-3-(2,6-difluorophenyl)propionic acid methyl ester.

Step 3

2(S)-Benzyloxycarbonylamino-3-(2,6-difluorophenyl) propionic acid methyl ester (5 g, 14.4 mmol) was dissolved in methanol (60 mL) and cooled on ice. 1 N NaOH (22 mL, 22 mmol) was added dropwise over 15 min. The reaction mixture was removed from cooling bath and stirring was continued at room temperature for 4 h. The solvent was then removed by rotary evaporation and the residue was treated with water (100 mL) and then with 1 N HCl to adjust the pH to 4. The product was extracted with ethyl acetate (300 mL, 200 mL). Evaporation of the solvent and crystallization of the residue from methylene chloride/hexane gave 2(S)-benzyloxycarbonylamino-3-(2,6-difluorophenyl)propionic acid (4.6 g, 13.7 mmol, 94% yield).

Step 4

2(S)-Benzyloxycarbonylamino-3-(2,6-difluorophenyl) propionic acid was hydrogenated at 50 psi in ethanol (25 mL) in the presence of 5% palladium on activated carbon (600 mg) for 24 h. The catalyst was removed by filtration through Celite® and the solvent evaporated to give a residue which was crystalized from ethyl ether to give 2(S)-2,6-difluorophenylalanine (2.2 g, 11 mmol, 80% yield). $^1$H NMR (DMSO-d$_6$): δ 7.28 (m, 1H), 7.0 (t, J=7.6 Hz, 2H), 2.77 (m, 2H). MS: 202.2 (M+1), 199.7(M−1).

Example C

Synthesis of 2(RS)-amino-4-methyl-4-phenylpentanoic acid

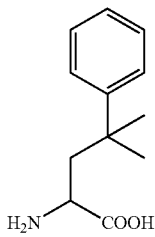

Step 1

4-Methyl-4-phenyl-1-pentene was prepared by reacting 2-phenyl-2-propanol with 3-(trimethylsilyl)propene by the method of Cella, *J. Org. Chem.*, 1982, 47, 2125-2130.

Step 2

4-Methyl-4-phenyl-1-pentene was ozonolyzed at −78° C. in dichloromethane followed by dimethyl sulfide quenching to give crude product which was purified by silica gel chromatography to give 3-methyl-3-phenylbutanal which was then converted to the title compound by proceeding as described in PCT application publication No. WO 2004/052921, Referenc C, on page 68 of the application.

Example D

Synthesis of 2(S)-benzyloxycarbonylamino-3-pyrazol-1-ylpropionic acid

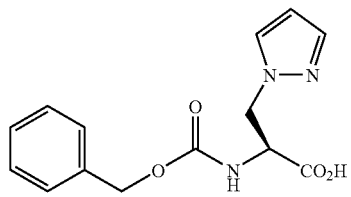

The title compound was prepared by treating S-benzyloxycarbonylserine-β-lactone with pyrazole in acetonitrile at 60° C. for 16 h (see *J. Am. Chem. Soc.,* 1985, 107, 7105-7109).

Following the procedure described above, but substituting pyrazole with 1,2,4-triazole and 1,2,3-triazole provided 2(S)-benzyloxycarbonylamino-3-[1.2.4]-triazol-1-ylpropionic acid and 2(S)-benzyloxycarbonylamino-3-[1.2.3]-triazol-1-ylpropionic acid respectively.

Example E

Synthesis of 2(S)-(tert-butoxycarbonyl)amino-3-thiazol-2-ylpropionic acid

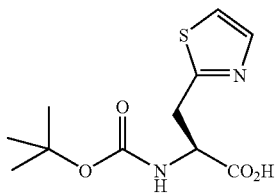

To 2-tert-butoxycarbonylamino-3-thiazol-2-ylpropionic acid methyl ester (500 mg, 1.75 mmol) in a mixture of acetonitrile (6 mL) and 0.2 M aqueous NaHCO$_3$ (12 mL) was added Alcalase (2.4 L, 0.08 mL), and the solution was stirred vigorously at room temperature for about 2.5 h. The reaction mixture was then evaporated at 30° C. to remove acetonitrile, and the aqueous residue was washed with ether. The aqueous phase was acidified with 6N HCl to pH 3 and the solution was extracted with ethyl acetate. The combined organic layers were then dried and evaporated to yield 2(S)-tert-butoxycarbonylamino-3-thiazol-2-ylpropionic acid (204 mg).

Reference F

Synthesis of 4-amino-4-cyano-1-ethylpiperidine

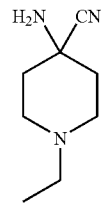

A mixture of 1-ethyl-4-piperidone (13.2 mL, 100 mmol), ammonium chloride (21.4 g, 400 mmol), sodium cyanide (19.6 g, 400 mmol) and water (550 mL) was stirred at room temperature for 48 h. The pH of the reaction mixture was adjusted to 10.1 and the product was extracted with ethyl acetate. The organic extracts were washed with brine and dried over magnesium sulfate. Rotary evaporation of the solvent gave a mixture of 4-amino-4-cyano-1-ethylpiperidine and 4-hydroxy-4-cyano-1-ethylpiperidine (7.67 g). This mixture of products was treated with 7M ammonia in methanol (20 mL) and allowed to stand at room temperature for 24 h. The methanol and excess ammonia were removed in vacuo and the residue was cooled to give 4-amino-4-cyano-1-ethylpiperidine as a crystalline solid (7.762 g).

Reference G

Synthesis of 2(S)-benzyloxycarbonylamino-3-(1-methylcyclopentyl)propionic acid

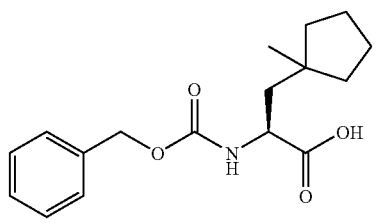

Step 1

1-Methylcyclopentanol (20 g, 0.2 mol) was added to hydrobromic acid (40 mL) at room temperature. After stirring for 1 h, the solution was extracted with hexane and the hexane was washed with brine and dried with magnesium sulfate. After concentration of the organic layer, 20.5 g of 1-methylcyclopentyl bromide was obtained.

Step 2

Tributyltin hydride (37.8 g, 130 mmol) was added at reflux to a 500 mL of flask charged with benzene (200 mL) was added Z-dehydro-Ala methyl ester (15 g, 64 mmol), 1-methylcyclopentyl bromide (20.5 g) and AIBN (1.9 g). After 2 h, the solvent was removed and the residue was purified by column chromatograph to yield 2-benzyloxycarbonylamino-3-(1-methylcyclopentyl)propionic acid methyl ester (7.9 g).

Step 3

2-Benzyloxycarbonylamino-3-(1-methylcyclopentyl)propionic acid methyl ester (7.6 g, 23.8 mmol) was dissolved in a mixture of acetonitrile (82 mL) and 0.2 M aqueous NaHCO$_3$ (158 mL) and Alcalase 2.4L (1.1 mL) was added and the reaction mixture was stirred vigorously for 8 h. The reaction mixture was then evaporated at 30° C. to remove acetonitrile, and the aqueous residue was washed with ether. The ethereal layer was concentrated to yield (R)-2-benzyloxycarbonylamino-3-(1-methylcyclopentyl)propionic acid methyl ester (1.9 g). The aqueous phase was filtered with Celite®, the pH was adjusted to 3 with 6N HCl, and the solution was extracted with ethylacetate. The ethyl acetate layer was dried and evaporated to yield 2(S)-benzyloxycarbonylamino-3-(1-methylcyclopentyl)propionic acid (1.4 g).

Reference H

Synthesis of trifluoromethanesulfonic acid 2,2,2-trifluoro-1-(4-fluorophenyl)ethyl ester

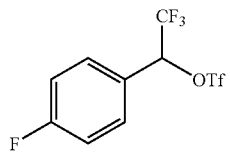

Step 1

To a stirred solution of 2,2,2,4'-tetrafluoroacetophone (10 g, 52.1 mmol) in methanol (50 mL) was added NaBH$_4$ (0.98 g, 26.5 mmol) at 0° C. After stirring at 25° C. for 2 h, the reaction mixture was quenched by adding 1N HCl (100 mL) and then extracted with ethyl ether. The ether extract was washed with brine, dried with MgSO$_4$, and concentrated to give 2,2,2-trifluoro-1-(4-fluorophenyl)ethanol (11.32 g) which was used in next step without further purificaiton.

Step 2

NaH (640 mg, 16 mmol, 60% in mineral oil) was washed twice with hexane (20 mL) and then suspended in dried diethyl ether (20 mL). A solution of 2,2,2-trifluoro-1-(4-fluoro-phenyl)ethanol (1.94 g, 10 mmol) in diethyl ether (10 mL) was added at 0° C. After stirring for 2 h at room temperature, a solution of trifluoromethanesulfonyl chloride (1.68 g, 10 mmol) in diethyl ether (10 mL) was added. After 2 h, the reaction mixture was quenched by adding a solution of NaHCO$_3$ and the product was extracted with diethyl ether. The extracts were washed with brine and dried, and the solvent was removed to yield trifluoromethanesulfonic acid 2,2,2-trifluoro-1-(4-fluorophenyl)ethyl ester (3.3 g).

Proceeding as described in Example H above, trifluoromethanesulfonic acid 2,2,2-trifluoro-1-phenylethyl ester was prepared.

Reference I

Synthesis of 2,2,2-trifluoro-1(R)-(4-fluorophenyl)ethanol

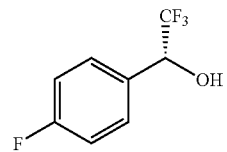

To a −78° C. toluene (25 mL)/dichloromethane (25 mL) solution of 2,2,2,4'-tetrafluoroacetophenone (2.5 g, 13.01 mmol) and 1M S-CBS catalyst (1.3 mL, 1.3 mmol) was added freshly distilled catecholborane (1.66 mL, 15.62 mmol). The reaction mixture was maintained at −78° C. for 16 h at which time 4N HCl (5 mL in dioxane) was added and the reaction mixture was allowed to warm to room temperature. The reaction mixture was diluted with ethyl acetate and washed with a saturated brine solution. The organic layer was dried over magnesium sulfate, filtered and concentrated to provide a solid. The solid was suspended in hexanes and filtered off. The hexanes filtrate containing the desired product was concentrated and the residue subjected to flash chromatography (10 hexanes: 1 ethylacetate) to provide the title compound as colorless oil (2.2 g, 87% yield). The ratio of enantiomers was determined to be 95:5 by chiral HPLC (Chiralcel OD column, 95 hexanes: 5 isopropanol mobile phase. Ret. time major product 6.757 min. Ret. time minor isomer 8.274 min.).

Reference J

Synthesis of 2(R)-3-cyclopropylmethylsulfanyl-2-(2,2,2-trifluoro-1(RS)-phenyl-ethylamino)propan-1-ol

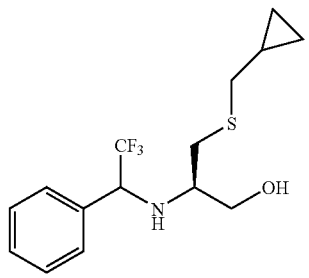

Step 1

An ice water bath cooled solution of L-cysteine in 1N sodium hydroxide (740 mL) and dioxane (740 mL) was treated with bromomethylcyclopropane (50 g, 370 mmol). The reaction mixture was allowed to warm to room temperature and stirred for 16 h. Dioxane was removed under reduced pressure and the resulting aqueous solution was adjusted to pH 6 with 6N HCl and placed in a refrigerator for 20 h. The product was collected by vacuum filtration, washed with hexanes and lyophilized to give 2(R)-amino-3-cyclopropylmethylsulfanylpropionic acid (57.28 g) as a white solid.

Step 2

To an ice water cooled solution of lithium aluminum hydride (200 mL of 1.0 M) was added solid 2(R)-amino-3-cyclopropylmethylsulfanylpropionic acid. The addition was done by tapping in portions through a funnel in such a manner as to control hydrogen gas evolution. The ice bath was removed, and the reaction mixture was heated at reflux for 16 h. The reaction mixture was removed from heat and cooled in an ice water bath. Diethyl ether (110 mL) was added, followed by dropwise addition of water (5 mL), 15% aqueous sodium hydroxide (5 mL), and water (15 mL). After stirring in the ice water bath for 1.5 h, the reaction mixture was filtered. The filtrate was dried over anhydrous sodium sulfate, and concentrated to give 2(R)-amino-3-cyclopropylmethylsulfanyl-propan-1-ol (14.9 g).

Step 3

To a stirred solution of 2(R)-amino-3-cyclopropylmethylsulfanylpropan-1-ol (80.5 mg, 0.5 mmol) in anhydrous THF (3 mL) were added activated 4A molecular sieves (250 mg) and N-methylmorpholine (51 mg, 0.5 mmol). After stirring for 10 min, trifluoromethanesulfonic acid 2,2,2-trifluoro-1-phenylethyl ester (190.5 mg, 0.5 mmol) was added and the reaction was stirred at room temperature for 2 days. The reaction mixture was filtered and the filtrate was concentrated. The residue was purified by flash column chromatography to afford the desired mixture of diastereomers of 2(R)-3-cyclopropylmethyl-sulfanyl-2-(2,2,2-trifluoro-1(RS)-phenylethylamino)-propan-1-ol. LC-MS: 318.3(M−1), 320.8 (M+1).

Reference K

Synthesis of 1-aminocyclopropanecarbonitrile hydrochloride

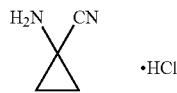

Step 1

A mixture of benzophenone imine (25 g, 0.138 mol, Aldrich) and aminoacetonitrile hydrochloride (25 g, 0.270 mol, Lancaster) in dichloromethane (1000 mL) was stirred in a 2L Erlenmeyer flask under nitrogen at room temperature for 5 days. The reaction mixture was filtered to remove the precipitated ammonium chloride and the filtrate was evaporated to dryness in vacuo. The resulting residue was dissolved in ether (400 mL) washed with water (200 mL) and brine. After drying over magnesium sulfate the solution was evaporated to give (benzhydrylideneamino)-acetonitrile (47.89 g).

Step 2

A solution of sodium hydroxide (91 g, 2.275 mol) in water (91 mL) in a 2L flask was cooled on ice under nitrogen and then treated with benzyl triethyl ammonium chloride (2.0 g, 0.0088 mol, Aldrich) and (benzhydrylideneamino)acetonitrile (47.89 g) in toluene (100 mL). 1,2-Dibromoethane (23 mL, 122.4 mmol, Aldrich) was then added dropwise over 25 min, to the reaction mixture with mechanical stirring and cooling to maintain the internal temperature near +10° C. The reaction mixture was then stirred vigorously for 24 h at room temperature and then poured into ice water and extracted with toluene. The combined extracts were washed with brine and then treated with MgSO4 and Norite. After filtering, toluene was removed by rotary evaporation to give an oil (67 g). The residue was dissolved in boiling hexane (400 mL), treated with Norite and filtered hot and allowed to cool. A dark oil separated and which was removed by pipet (~2 mL). Scratching induced crystallization in the remaining solution which was cooled on ice for 2 h. Light yellow crystals were collected by filtration and washed with cold hexane to give 1-(benzhydrylideneamino)cyclopropane-carbonitrile (30.56 g).

Step 3

A mixture of 1-(benzhydrylideneamino)cyclopropanecarbonitrile (30.56 g, 0.124 mol) in concentrated HCl (12 mL) in water (100 mL) and ether (100 mL) was stirred at room temperature for 15 h. The ether layer was discarded and the aqueous layer was washed with ether. The aqueous layer was then freeze dried to give the title compound as a tan powder (13.51 g).

Reference L

Synthesis of 2(R)-amino-3-[2-(difluoromethoxy)phenylmethanesulfanyl]propionic acid

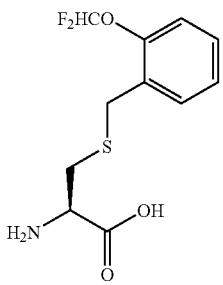

A solution of L-cysteine (5.1 g, 42.2 mmol) in 2N NaOH (42.2 mL) was cooled in an ice water bath. Neat 1-bromomethyl-2-difluoromethoxybenzene (10 g, 42.2 mmol) was added and the reaction mixture was allowed to stir and warm to room temperature over 4 h. The reaction mixture was cooled in an ice bath and the pH was adjusted 6 using 3N HCl, then 1N HCl when the white precipitate that formed became too thick to allow stirring. The precipitates were collected by vacuum filtration, washed with hexanes and dried by lyophilization to give the title compound (11.14 g) as a white solid.

Reference M

Synthesis of 4-amino-1-(2,2,2-trifluoroethyl)piperidine-4-carbonitrile hydrochloride

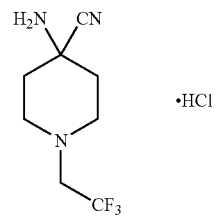

Step 1

In a solution of 1,4-dioxa-8-aza-spiro[4.5]decane (14.3 g, 100 mmol) in CH$_2$Cl$_2$ (200 mL) was added Et$_3$N (15.2 g, 150 mmol), DMAP (30 mg) and trifloroacetic acid anhydride (25.2 g, 150 mmol) at 0° C., then allowed to warm-up to room temperature and stirred for 12 h. The reaction mixture was quenched with water and washed with 1N HCl and brine, dried with MgSO$_4$. Removal of the solvent, yielded 1-(1,4-dioxa-8-aza-spiro[4.5]dec-8-yl)-2,2,2-trifluoroethanone (35 g). The crude product was used in the next reaction.

Step 2

In the solution of 1-(1,4-dioxa-8-aza-spiro[4.5]dec-8-yl)-2,2,2-trifluoroethanone (20 g, 83.7 mmol) in THF, borane-methyl sulfide complex (83.7 mL, 2M solution in THF) was added at 0° C. After refluxing the reaction mixture for 12 h, the reaction was cooled and quenched with MeOH. After removal of THF, the residue was extracted with ethyl acetate and washed with brine, dried with MgSO$_4$ and concentrated to give 8-(2,2,2-trifluoroethyl)-1,4-dioxa-8-aza-spiro[4.5] decane (19 g) was obtained.

Step 3

8-(2,2,2-Trifluoroethyl)-1,4-dioxa-8-aza-spiro[4.5]decane (3.7 g, 16 mmol) was added to a solution of 5% HCl (45 mL) and acetone (8 mL). After refluxing for 12 h, the solvent was removed to give crude 1-(2,2,2-trifluoroethyl)piperidin-4-one hydrochloride which was used in the next reaction.

Step 4

A solution of ammonium chloride (3.2 g, 60 mmol) and potassium cyanide (2.94 g, 60 mmol) was prepared in water (25 mL) and 1-(2,2,2-trifluoroethyl)-piperidin-4-one hydrochloride (3.5 g, 15 mmol) was added and the reaction mixture was stirred for 2 days. The solution was then brought to pH 11 with sodium carbonate and the reaction mixture was extracted with ethyl acetate. After drying over Na$_2$SO$_4$, the solvent was removed to yield a mixture of 4-hydroxy-1-(2,2,2-trifluoroethyl)piperidine-4-carbonitrile and 4-amino-1-(2,2,2-trifluoroethyl)piperidine-4-carbonitrile. This mixture was then treated with 7N ammonia solution in MeOH for 12 h at room temperature. After removal of the solvent, the residue was dissolved in ethyl ether and treated with 4N HCl solution in dioxane. The solids were filtered and dried under vacuum, to yield 4-amino-1-(2,2,2-trifluoroethyl)piperidine-4-carbonitrile hydrochloride (2.5 g).

Example 1

Synthesis of N-(1-cyanocyclopropyl)-3-phenyl-methanesulfonyl-2(R)-(2,2,2-trifluoro-1(RS)-thiophen-2-yl-ethylamino)propionamide

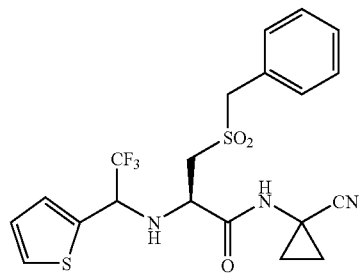

Step 1

To a cold (0° C.), stirred solution of 2(R)-amino-3-phenyl-methanesulfanylpropionic acid (commercially available) (4.01 g, 19.0 mmol) in methanol (100 mL) was introduced HCl gas for 15 min and the reaction mixture was sealed and stirring was continued at rt overnight. The solvent was then evaporated under vacuum to give methyl 2(R)-amino-3-phenyl-methanesulfanylpropionate HCl in quantitative yield (4.98 g).

Step 2

A mixture of methyl 2(R)-amino-3-phenylmethanesulfanylpropionate HCl salt (4.95 g, 18.9 mmol) and trifluoroacetaldehyde methyl hemiacetal (3.12 g, 24.0 mmol) containing p-toluenesulfonic acid (0.19 g) in benzene (60 mL) was stirred at rt overnight. The reaction mixture was diluted with ethyl acetate (100 mL), washed with 100% sodium bicarbonate, and then water. The organic phase was dried (MgSO$_4$) and the solvent was removed under reduced pressure to give methyl 3-phenylmethanesulfanyl-2(R)-(2,2,2-trifluoro-1(RS)-hydroxyethylamino)-propionate as a mixture of diastereomers in about 3:2 ratio. This crude material was used for the next step without purification.

Step 3

To a cold (0° C.) stirred mixture of methyl 3-phenyl-methanesulfanyl-2(R)-(2,2,2-trifluoro-1(RS)-hydroxyethyl-amino)propionate (524 mg, 1.65 mmol) and thiophene (415 mg, 4.95 mmol) in dichlomethane (3 mL) was added BF$_3$.Et$_2$O (0.25 mL, 1.98 mmol) dropwise via a micro syringe and the reaction mixture was allowed to warm to rt over 1 h. After being stirred at rt for additional 4 h, the reaction mixture was quenched by addition of about 0.2 mL methanol. The reaction mixture was stirred for 5 min, diluted with dichloromethane, and partitioned with water. The combined organic extracts were dried (MgSO$_4$), concentrated under reduced pressure, and the residue was purified by flash chromatography on silica gel (eluted with 1:6 EtOAc/hexanes) to yield methyl 3-phenylmethanesulfanyl-2(R)-(2,2,2-trifluoro-1 (RS)-thiophen-2-yl-ethylamino)propionate (200 mg) as a mixture of diastereomers in a 3:2 ratio.

Step 4

To a stirred solution of the methyl 3-phenylmethanesulfanyl-2(R)-(2,2,2-trifluoro-1(RS)-thiophen-2-yl-ethylamino)-propionate (200 mg, 0.514 mmol) in methanol (3 mL) at room temperature was added aqueous 1N KOH solution (0.77 mL). After being stirred overnight, the reaction mixture was concentrated, diluted with water (5 mL), acidified with 1N HCl (pH=ca. 3), and then extracted with ethyl acetate. The combined organic layers were dried over MgSO$_4$, and concentrated to give 3-phenylmethanesulfanyl-2(R)-(2,2,2-trifluoro-1(RS)-thiophen-2-yl-ethylamino)-propionic acid (191 mg) which was used directly without further purification.

Step 5

To a solution of 3-phenylmethanesulfanyl-2(R)-(2,2,2-trifluoro-1(RS)-thiophen-2-yl-ethylamino)propionic acid (190 mg, 0.52 mmol), 1-aminocyclopropanecarbonitrile HCl salt (92 mg, 0.78 mmol) in DMF (3 mL) at rt was added HATU (237 mg, 0.624 mmol), followed by diisopropylethylamine (0.45 mL, 2.6 mmol). After being stirred at rt overnight, the reaction mixture was concentrated under reduced pressure and then partitioned between ethyl acetate and brine. The combined organic extracts were dried (MgSO$_4$), concentrated under reduced pressure, and the residue was purified by flash chromatography on silica gel (eluted with 1:2 EtOAc/hexanes) to yield 3-phenylmethanesulfanyl-N-(1-cyanocyclopropyl)-2(R)-(2,2,2-trifluoro-1(RS)-thiophen-2-ylethylamino)-propionamide (164 mg) as a mixture of diastereomers in a 3:2 ratio. $^1$H NMR for a major isomer (400 MHz, CDCl$_3$): δ 7.8-6.95(9H, m) 4.39(1H, q), 3.78(2H, s), 3.35(1H, s), 2.82(2H, m), 1.65-1.01(4H, m). MS: 440.1(M+1).

Step 6

A solution of OXONE® (290 mg, 0.47 mmol) in water (1.5 mL) was added to a solution of 3-phenylmethanesulfanyl-N-(1-cyanocyclopropyl)-2(R)-(2,2,2-trifluoro-1(RS)-thiophen-2-ylethylamino)propionamide (159 mg, 0.362 mmol) in methanol (3 mL). The reaction mixture was stirred at rt for 4 h and then removed the solvent under reduced pressure. The residue obtained was partitioned between ethyl acetate and brine. The combined organic extracts were dried (MgSO$_4$), concentrated under reduced pressure. The crude was purified by passing through a short pad of a Celite® to give the title compound as a mixture of diastereomers in a 3:2 ratio.

$^1$H NMR (400 MHz, CDCl$_3$): δ 7.57(1H, s), 7.40-7.25 (6H, m), 7.00 (1H, d), 6.89 (1H, t), 4.58 (1H, q), 4.48-4.19 (2H, m), 3.69 (1H,m), 3.30(1H, dd), 3.09 (1H, dd), 1.45-0.79 (4H, m). MS: 472.5(M+1).

Proceeding as described above, the following compounds were prepared:

N-(1-cyanocyclopropyl)-3-phenylmethanesulfonyl-2(R)-(2,2,2-trifluoro-1(RS)-furan-2-yl-ethylamino)propionamide as a mixture of diastereomers in a 3:2 ratio. $^1$H NMR (400 MHz, DMSO-d6): δ 9.01(1H, s), 7.63(1H, s), 7.39(5H, m), 6.60-6.40(2H, m), 4.58(2H, m), 4.45(1H, m), 3.69(1H, m), 3.80-3.05(3H, m), 3.09(1H, dd), 1.45-0.79(4H, m). MS: 456.0 (M+1).

N-(1-cyanocyclopropyl)-3-phenylmethanesulfonyl-2(R)-[2,2,2-trifluoro-1(S)-(1-methyl-1H-pyrrol-2-yl)ethylamino]propionamide.

$^1$H NMR (400 MHz, CDCl$_3$): δ 7.50-7.35(6H, m), 6.56 (1H, m), 6.06(1H, m), 4.45(2H, m), 4.22(1H, q), 3.73(1H, dd), 3.33(1H, dd), 3.04(1H, dd), 1.55-1.00(4H, m). MS: 469.2 (M+1).

N-(1-cyanocyclopropyl)-3-phenylmethanesulfonyl-2(R)-[2,2,2-trifluoro-1(S)-(4-hydroxy-phenyl)ethylamino]propionamide.

$^1$H NMR (400 MHz, DMSO-d$_6$): δ 9.60(1H, s), 9.02(1H, s), 7.40 (5H, m), 7.18(2H, m), 6.73(2H, m), 4.70(1H, d), 4.50(1H, d), 4.21(m, 1H), 3.69(1H, m), 3.45-3.09(3H, m), 1.40-0.60(4H, m). MS: 482.1(M+1).

N-(1-cyanocyclopropyl)-3-phenylmethanesulfonyl-2(R)-[2,2,2-trifluoro-1(RS)-(1H-indol-3-yl)ethylamino]propionamide as a mixture of diastereomers in a 5:4 ratio.

$^1$HMR (400 MHz, CDCl$_3$): δ 8.40 (s, 1H), 7.60-7.0(10 H, m), 4.58(1H, m), 4.38-4.05(2H, m), 3.62(1H, m), 3.80-2.95 (4H, m), 1.40-0.69(4H, m). MS: 505.4(M+1).

N-(1-cyanocyclopropyl)-3-cyclopropylmethanesulfonyl-2(R)-(2,2,2-trifluoro-1(RS)-1-phenylsulfonylpyrrol-2-yl-ethylamino)propionamide (using commercially available 1-phenylsulfonylpyrrole). MS: 559.3 (M+1).

N-(1-cyanocyclopropyl)-3-(2-difluoromethoxyphenyl-methanesulfonyl)-2(R)-(2,2,2-trifluoro-1(RS)-1-phenylsulfonylpyrrol-2-ylethylamino)propionamide. MS: 661.6 (M+1).

N-(1-cyanocyclopropyl)-3-cyclopropylmethanesulfonyl-2(R)-(2,2,2-trifluoro-1(S)-1-methylpyrrol-2-ylethylamino)propionamide. MS: 432.9 (M+1).

N-(1-cyanocyclopropyl)-3-cyclopropylmethanesulfonyl-2(R)-(2,2,2-trifluoro-1(RS)-thiophen-2-yl-ethylamino)propionamide. MS: 436.2 (M+1).

N-(1-cyanocyclopropyl)-3-(2-difluoromethoxyphenyl-methanesulfonyl)-2(R)-(2,2,2-trifluoro-1(RS)-thiophen-2-ylethylamino)propionamide. MS: 538.2 (M+1)

N-(1-cyanocyclopropyl)-3-(1-methylcyclopentyl)-2(S)-(2,2,2-trifluoro-1(S)-3-fluoro-4-hydroxyphenylethylamino)propionamide. MS: 428.1 (M+1).

N-(1-cyanocyclopropyl)-3-phenylmethanesulfonyl-2(R)-(2,2,2-trifluoro-1(S)-3-chloro-4-hydroxyphenylethylamino)propionamide. MS: 516.3 (M+1).

N-(1-cyanocyclopropyl)-3-(1-methylcyclopentyl)-2(S)-(2,2,2-trifluoro-1(S)-4-hydroxyphenylethylamino)propionamide. MS: 410.2 (M+1).

N-(1-cyanocyclopropyl)-3-(1-methylcyclopentyl)-2(S)-(2,2,2-trifluoro-1(S)-2-hydroxyphenylethylamino)propionamide. MS: 410.2 (M+1).

N-(1-cyanocyclopropyl)-3-(1-methylcyclopentyl)-2(S)-(2,2,2-trifluoro-1(R)-thiophen-2-yl-ethylamino)propionamide. MS: 400.2 (M+1).

N-(1-cyanocyclopropyl)-3-phenylmethanesulfonyl-2(R)-(2,2,2-trifluoro-1(S)-methylethylamino)propionamide. MS: 404.1 (M+1).

N-(1-cyanocyclopropyl)-3-phenylmethanesulfanyl-2(R)-(2,2,2-trifluoro-1(S)-4-hydroxyphenylethylamino)propionamide. MS: 450.2 (M+1).

N-(1-cyanocyclopropyl)-3-phenylmethanesulfanyl-2(R)-(2,2,2-trifluoro-1(RS)-furan-2-ylethylamino)propionamide. MS: 424.0 (M+1).

N-(1-cyanocyclopropyl)-3-phenylmethanesulfanyl-2(R)-(2,2,2-trifluoro-1(RS)-indol-3-yl-ethylamino)propionamide. MS: 473.4 (M+1).

N-(1-cyanocyclopropyl)-3-phenylmethanesulfanyl-2(R)-(2,2,2-trifluoro-1(RS)-thiophen-2-ylethyl-amino)propionamide. MS: 440.1 (M+1).

N-(1-cyanocyclopropyl)-3-phenylmethanesulfonyl-2(R)-(2,2,2-trifluoro-1(RS)-thiophen-2-ylethylamino)propionamide. MS: 472.5 (M+1).

N-(1-cyanocyclopropyl)-3-(1-methylcyclopentyl)-2(S)-(2,2,2-trifluoro-1(S)-thiophen-2-ylethylamino)propionamide. MS: 422.4 (M+23).

N-(1-cyanocyclopropyl)-3-(1-methylcyclopentyl)-2(S)-(2,2,2-trifluoro-1(R)-4-hydroxyphenylethylamino)propionamide. MS: 410.2 (M+1).

N-(1-cyanocyclopropyl)-3-phenylmethanesulfanyl-2(R)-(2,2,2-trifluoro-1(R)-3-chloro-4-hydroxyphenylethylamino)propionamide. MS: 484.2 (M+1).

N-(1-cyanocyclopropyl)-3-phenylmethanesulfonyl-2(R)-(2,2,2-trifluoro-1(S)-3-chloro-4-hydroxy-phenylethylamino)propionamide. MS: 484.2 (M+1).

N-(1-cyanocyclopropyl)-3-phenylmethanesulfonyl-2(R)-(2,2,2-trifluoro-1(R)-3-chloro-4-hydroxyphenylethylamino)propionamide. MS: 516.3 (M+1).

N-(1-cyanocyclopropyl)-3-(2-difluoromethoxyphenyl-methanesulfanyl)-2(R)-(2,2,2-trifluoro-1(RS)-thiophen-2-ylethylamino)propionamide. MS: 506.3 (M+1).

N-(1-cyanocyclopropyl)-3-cyclopropylmethanesulfanyl-2(R)-(2,2,2-trifluoro-1(RS)-thiophen-2-yl-ethylamino)propionamide. MS: 404.1 (M+1).

N-(1-cyanocyclopropyl)-3-cyclopropylmethanesulfonyl-2(R)-(2,2,2-trifluoro-1(S)-1-oxo-1-methylpyrrol-2-ylethylamino)propionamide. MS: 449.2 (M+1).

Proceeding as described above but substituting trifluoroacetaldehyde methyl hemiacetal with difluoroacetaldehyde ethyl acetal and 2(R)-amino-3-phenylmethanesulfanylpropionic acid with 2(S)-benzyloxycarbonylamino-3-(1-methylcyclopentyl)propionic acid provided N-(1-cyanocyclopropyl)-3-(1-methylcyclopentyl)-2(S)-(2,2-difluoro-1(R)-thiophen-2-yl-ethylamino)propionamide. $^1$HNMR (DMSO-d$_6$): δ 8.80 (1H, s), 7.56 (1H, dd), 7.08 (1H, m), 7.03 (1H, m), 6.07 (1H, dt), 4.15 (1H, m), 3.23 (1H, m), 1.50 (12H, m), 0.95 (2H, m), 0.94 (3H, s).

Proceeding as described above but substituting trifluoroacetaldehyde methyl hemiacetal with difluoroacetaldehyde ethyl acetal provided N-(1-cyanocyclopropyl)-3-phenylmethanesulfanyl-2(R)-(2,2-difluoro-1(RS)-thiophen-2-yl-ethylamino)propionamide. ¹HNMR (DMSO-$d_6$): δ 8.92-8.88 (1H, s), 7.61-7.55 (1H, d), 7.30 (5H, m), 7.10 (2H, m), 6.11 (1H, dt), 4.35-4.20 (1H, m), 3.30-3.20 (1H, m), 2.88-2.81 (1H, m), 2.64 (1H, m), 2.58 (2H, m), 1.52-145 (2H, m), 1.16 (1H, m), 1.00 (1H, m). LC/MS: M+1: 422.2.

N-(1-cyanocyclopropyl)-3-phenylmethanesulfanyl-2(R)-(2,2-difluoro-1(RS)-thiophen-2-yl-ethylamino)propionamide was oxidized as described above and N-(1-cyanocyclopropyl)-3-phenylmethanesulfanyl-2(R)-(2,2-difluoro-1(R)-thiophen-2-yl-ethylamino)propionamide. ¹HNMR: δ 9.01-9.04 (1H, s), 7.62-7.56 (1H, dd), 7.40 (5H, m), 7.14 (1H, m), 7.09-7.05 (1H, m), 6.18 (1H, dt), 4.73 (1H, m), 4.55 (1H, m), 4.40-4.25 (1H, m), 3.40-3.25 (1H, m), 3.40 (3H, m), 3.20 (1H, m) 1.50 (2H, m), 1.10 (2H, m). LC/MS, M+1: 454.1.

Example 2

Synthesis of N-(1-cyanocyclopropyl)-3-cyclopropyl-methanesulfonyl-2(R)-(2,2-trifluoro-1(S)-phenyl-ethylamino)propionamide

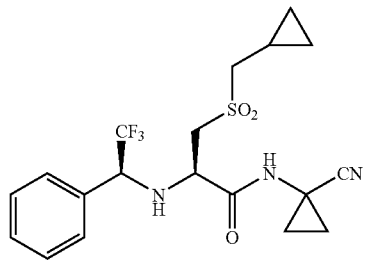

Step 1

An ice water bath cooled solution of L-cysteine in 1N sodium hydroxide (740 mL) and dioxane (740 mL) was treated with bromomethylcyclopropane (50 g, 370 mmol). The reaction mixture was allowed to warm to room temperature and stirred for 16 h. Dioxane was removed under reduced pressure and the resulting aqueous solution was adjusted to pH 6 with 6N HCl and placed in a refrigerator for 20 h. The product was collected by vacuum filtration, washed with hexanes and lyophilized to give 2(R)-amino-3-cyclopropylmethylsulfanylpropionic acid (57.28 g) as a white solid.

Step 2

To an ice water cooled solution of lithium aluminum hydride (200 mL of 1.0 M) was added solid 2(R)-amino-3-cyclopropylmethylsulfanylpropionic acid. The addition was done by tapping in portions through a funnel in such a manner as to control hydrogen gas evolution. The ice bath was removed, and the reaction mixture was heated at reflux for 16 h. The reaction mixture was removed from heat and cooled in an ice water bath. Diethyl ether (110 mL) was added, followed by dropwise addition of water (5 mL), 15% aqueous sodium hydroxide (5 mL), and water (15 mL). After stirring in the ice water bath for 1.5 h, the reaction mixture was filtered. The filtrate was dried over anhydrous sodium sulfate, and concentrated to give 2(R)-amino-3-cyclopropylmethylsulfanyl-propan-1-ol (14.9 g).

Step 3

A solution of 2(R)-amino-3-cyclopropylmethylsulfanyl-propan-1-ol (14.9 g, 93 mmol), tert-butyldimethylchlorosilane (15.4 g, 102 mmol), 4-(N,N-dimethylamino)pyridine (182 mg, 1.49 mmol) and triethylamine (20.7 mL, 149 mmol) in dichloromethane (190 mL) was stirred at room temperature for 3.5 h. Saturated ammonium chloride (300 mL) was added and the layers were separated. The aqueous layer was extracted with dichloromethane and the combined organic layers were washed with brine, dried over anhydrous sodium sulfate, and concentrated to give 1-(tert-butyldimethylsilanyloxy)-2(R)-cyclopropylmethylsulfanylmethylethylamine (24.06 g).

Step 4

A mixture of 1-(tert-butyldimethylsilanyloxy)-2(R)-cyclopropylmethylsulfanyl-methylethylamine (24 g, 87.5 mmol), trifluoroacetaldehyde methyl hemiacetal (11.4 g, 87.5 mmol) and toluene (90 mL) was heated at reflux with Dean Stark trapping of water for 22 h. The reaction mixture was concentrated and chromatographed on silica gel using 9:1 hexanes: ethyl acetate to give [1-(tert-butyldimethylsilanyloxy)-2(R)-cyclopropylmethylsulfanylmethylethyl]-(2,2,2-trifluoro-ethylidene)amine (22.5 g) as a pale tan oil.

Step 5

To a solution of phenyllithium (6 mL of 1.8 M solution in di-n-butyl ether, 10.8 mmol) and anhydrous tetrahydrofuran (19.5 mL) cooled in a dry ice acetone bath was added [1-(tert-butyldimethylsilanyloxy)-2(R)-cyclopropylmethylsulfanyl-methylethyl]-(2,2,2-trifluoroethylidene)-amine (3.55 g, 10.0 mmol) in anhydrous tetrahydrofuran (4.9 mL) dropwise. The reaction mixture was then transferred to an acetonitrile dry ice bath and allowed to stir for 2.5 h. It was then kept in a freezer for 12 h. The reaction mixture was poured into ice and saturated ammonium chloride and was extracted with ethyl acetate. The organic layer was dried over anhydrous sodium sulfate, concentrated to give [1-(tert-butyldimethylsilanyloxymethyl)-2(R)-cyclopropylmethyl-sulfanylethyl]-(2,2,2-trifluoro-1(S)-phenylethyl)amine and [1-(tert-butyldimethylsilanyloxymethyl)-2(R)-cyclopropylmethyl-sulfanylethyl]-(2,2,2-trifluoro-1(R)-phenylethyl)amine (5.65 g) as a approx. 2:1 mixture which was used in the next step without further purification.

Step 6

To an ice water bath cooled anhydrous tetrahydrofuran solution (25 mL) of [1-(tert-butyldimethylsilanyloxymethyl)-2(R)-cyclopropylmethyl-sulfanylethyl]-(2,2,2-trifluoro-1(S)-phenylethyl)amine and [1-(tert-butyldimethylsilanyloxymethyl)-2(R)-cyclopropylmethyl-sulfanylethyl]-(2,2,2-trifluoro-1(R)-phenylethyl)amine was added tetrabutylammonium fluoride (10 mL of 1.0 M) in tetrahydrofuran dropwise. The reaction mixture was placed in a 4° C. freezer for 16 h and then poured into cold saturated ammonium chloride and was extracted with ethyl acetate. The organic layer was washed with water and brine, dried over anhydrous sodium sulfate and concentrated to a liquid product that was further purified by silica gel chromatography using 4:1 hexanes:ethyl acetate eluent to give a mixture of 3-cyclopropylmethylsulfanyl-2(R)-(2,2,2-trifluoro-1(S)-phenylethylamino)propan-1-ol and 3-cyclopropylmethylsulfanyl-2(R)-(2,2,2-trifluoro-1(R)-phenylethylamino)propan-1-ol (1.91 g) as a pale yellow oil.

Step 7

To an ice water bath cooled solution of 3-cyclopropylmethylsulfanyl-2(R)-(2,2,2-trifluoro-1S-phenylethylamino)propan-1-ol and 3-cyclopropylmethylsulfanyl-2(R)-(2,2,2-trifluoro-1(R)-phenylethylamino)propan-1-ol (1.75 g, 5.5 mmol) in anhydrous acetonitrile (26 mL) was added $H_5IO_6$/$CrO_3$ (26.3 mL of 0.41M) in acetonitrile [Note: $H_5IO_6$ (11.4 g, 50 mmol), $CrO_3$ (23 mg) and anhydrous acetonitrile (114 mL) were stirred at room temperature for 3 h before use]. The cooling bath was removed and the reaction mixture was stirred for 4 h. An additional oxidant solution (5 mL) was added and the reaction mixture was stirred an additional 0.5 h. Saturated aqueous $KH_2PO_4$ (50 mL) was added and the reaction mixture was extracted with ethyl acetate. The combined organic layers were washed with 1:1 water: brine, then 1:1 dilute $NaHSO_3$, brine, dried over anhydrous sodium sulfate, and concentrated. The crude product was dissolved in saturated sodium bicarbonate washed with diethyl ether. This diethyl ether layer contained some unreacted alcohol starting material. The aqueous layer was pH adjusted to 4.3 with 6N HCl and extracted with ethyl acetate. The organic layers were dried over anhydrous sodium sulfate, concentrated to give a mixture of 3-cyclopropylmethanesulfonyl-2(R)-(2,2,2-trifluoro-1(S)-phenylethylamino)-propionic acid and 3-cyclopropylmethanesulfonyl-2(R)-(2,2,2-trifluoro-1(R)-phenylethylamino)-propionic acid (150 mg).

Step 8

A solution of 3-cyclopropylmethanesulfonyl-2(R)-(2,2,2-trifluoro-1(S)-phenylethylamino)-propionic acid and 3-cyclopropylmethanesulfonyl-2(R)-(2,2,2-trifluoro-1(R)-phenylethylamino)-propionic acid (140 mg, 0.38 mmol), 1-aminocyclopropane-carbonitrile hydrochloride (45 mg, 0.38 mmol) HATU (173 mg, 0.46 mmol) and N-methylmorpholine (100 µL, 0.91 mmol) in anhydrous DMF (0.75 mL) was stirred at room temperature for 16 h. The reaction mixture was partitioned between ethyl acetate and saturated aqueous sodium bicarbonate. The aqueous layer with extracted again with ethyl acetate. The combined ethyl acetate layers were washed with brine, dried over anhydrous sodium sulfate, and concentrated. The crude product was purified by silica gel chromatography using 1:1 hexanes: ethyl acetate to give a fraction that was further purified by crystallization from diethyl ether and hexanes to give N-(1-cyanocyclopropyl)-3-cyclopropyl-methanesulfonyl-2(R)-(2,2,2-trifluoro-1(S)-phenylethylamino)propionamide (6.77 mg).

$CDCl_3$, 400 MHz. δ 7.59 (1H, br s), 7.44 (3H, m), 7.39 (2H m), 4.38 (1H, q, J=6.8 Hz), 3.68 (1H, m), 3.64 (1H, dd, J=14.0 Hz, 6.4 Hz), 3.39 (1H, dd, J=14.4 Hz, 4.0 Hz), 3.03 (2H, d, J=7.2 Hz), 1.57 (2H, m), 1.21 (3H, m), 0.79 (2H, m), 0.49 (2H, m).

Proceeding as described above, but using commercially available 2(R)-amino-3-benzylsulfanylpropan-1-ol, N-(1-cyanocyclopropyl)-3-phenylmethanesulfonyl-2(R)-(2,2,2-trifluoro-1(S)-phenylethylamino)propionamide was prepared. MS: 466.2 (M+1); 488.1 (M+23); 464.1 (M−1).

Proceeding as described above, but substituting 1-aminocyclopropanecarbonitrile hydrochloride with 4-amino-4-cyano-1-ethylpiperidine hydrochloride salt and 2(R)-amino-3-cyclopropylmethylsulfanyl-propan-1-ol with 2(R)-amino-3-benzylsulfanylpropan-1-ol provided N-(4-cyano-1-ethylpiperidin-4-yl)-3-cyclopropylphenylmethanesulfonyl-2 (R)-(2,2,2-trifluoro-1(S)-phenylethylamino)propionamide.

Proceeding as described in Example 2 above but substituting 1-aminocyclopropane-carbonitrile with 1-aminotetrahydrothiopyran-4-ylcarbonitrile (prepared as described in J. Med. Chem., 1978, 1070 or PCT application publication No. WO 01/19816 as described on page 141, Example 2 substituting tetrahydropyran-4-one with tetrahydrothiopyran-4-one) and 2(R)-amino-3-cyclopropylmethylsulfanylpropan-1-ol with 2(R)-amino-3-benzylsulfanylpropan-1-ol provided N-(4-cyanotetrahydrothiopyran-4-yl)-3-phenylmethanesulfanyl-2(R)-(2,2,2-trifluoro-1(S)-phenylethylamino)-propionamide which upon oxidation as provided in Example 3 below provided N-(4-cyano-1-hexahydro-1λ$^6$-thiopyran-4-yl)-3-phenylmethanesulfonyl-2(R)-(2,2,2-trifluoro-1(S)-phenylethylamino)-propionamide. MS: 526.3 (M+1); 548.1 (M+23); 524.2 (M−1).

N-(1-cyanocyclopropyl)-3-cyclopropylmethanesulfonyl-2(R)-(2,2,2-trifluoro-1(S)-3-bromophenylethylamino)propionamide. MS: 508 (M+1).

N-(1-cyanocyclopropyl)-3-phenylmethanesulfonyl-2(R)-(2,2,2-trifluoro-1(S)-4-fluorophenylethylamino)propionamide. MS: 484.0 (M+1)

N-(1-cyanocyclopropyl)-3-cyclopropylmethanesulfonyl-2(R)-(2,2,2-trifluoro-1(S)-thiophen-3-ylethylamino)propionamide. MS: 435.9 (M+1)

N-(1-cyanotetrahydropyran-4-yl)-3-cyclopropylmethanesulfonyl-2(R)-(2,2,2-trifluoro-1(S)-4-fluorophenylethylamino)propionamide. MS: 492.0 (M+1)

N-(1-cyanocyclopropyl)-3-(4-fluorophenylmethanesulfonyl)-2(R)-(2,2,2-trifluoro-1(S)-4-fluorophenylethylamino) propionamide. MS: 502.2 (M+1)

N-(1-cyanotetrahydrothiopyran-4-yl)-3-(4-fluorophenylmethanesulfonyl)-2(R)-(2,2,2-trifluoro-1(S)-4-fluorophenyl-ethylamino)propionamide. MS: 562.1 (M+1)

N-(1-cyancyclopropyl)-3-(4-fluorophenylmethanesulfonyl)-2(R)-(2,2,2-trifluoro-1(S)-3-phenoxyphenylethylamino)propionamide. MS: 476.1 (M+1)

N-(1-cyano-1,1-dioxohexahydro-1λ$^6$-thiopyran-4-yl)-3-(4-fluorophenylmethane-sulfonyl)-2(R)-(2,2,2-trifluoro-1 (S)-4-fluorophenylethylamino)propionamide. MS: 494.2 (M+1).

Example 3

Synthesis of N-(4-cyano-1,1-dioxohexahydro-1λ$^6$-thiopyran-4-yl)-3-cyclopropylmethanesulfonyl-2(R)-(2,2,2-trifluoro-1(S)-phenylethylamino)propionamide

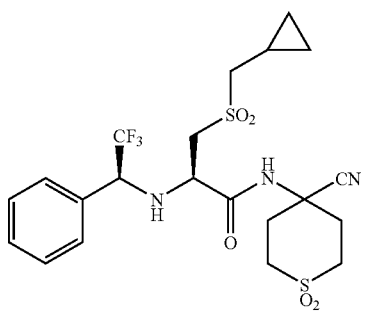

A solution of N-(4-cyanotetrahydrothiopyran-4-yl)-3-cyclopropylmethanesulfanyl-2(R)-(2,2,2-trifluoro-1(S)-phenylethylamino)-propionamide (0.131 mmol) in methanol (3 mL) was treated with a solution of OXONE® (245 mg) in water (3 mL) and stirred for 30 h at room temperature. The reaction mixture was extracted with diethyl ether and the organic layer was washed with brine, dried over anhydrous sodium sulfate, and concentrated. The crude product was purified by silica gel chromatography using 50% ethyl acetate in hexane to 100% ethyl acetate gradient as eluent to give the title compound (9 mg) after trituration with diethyl ether.

M+1=558.4; M+23=580.7; M−1=556.4.

Example 4

Synthesis of N-(1-cyanocyclopropyl)-3-pyridin-2-ylmethanesulfonyl-2(R)-(2,2,2-trifluoro-1(S)-4-fluorophenylethylamino)propionamide

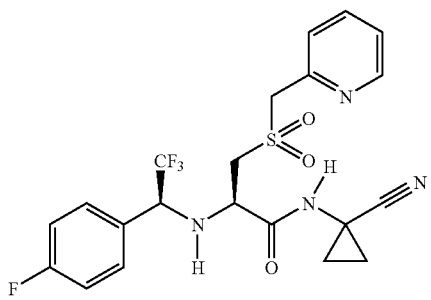

Step 1

To a solution of (Boc-Cys-OH)$_2$ (20 g, 45.4 mmol) and P(CH$_2$CH$_2$COOH)$_3$.HCl (15.61 g, 54.47 mmol) in DMF (162 mL) was added 5N KOH (109 mL) slowly over 20 min. After stirring overnight, 2-picolylchloride hydrochloride (22.34 g, 136.2 mmol) was added in one portion and the reaction mixture was stirred at room temperature for 2.5 h. The pH of the solution was adjusted to 3 with 10N HCl and the product was extracted with methylene chloride. The combined organic extract was washed with sat. NaHCO$_3$, dried over MgSO$_4$, filtered and concentrated to give 2(R)-N-tert-butoxycarbonylamino-3-(pyridin-2-ylmethylsulfanyl)propionic acid which was crystallized from methylene chloride and hexane mixture to give pure product (13.70 g) as a white solid.

Step 2

2(R)-N-tert-Butoxycarbonylamino-3-(pyridin-2-ylmethylsulfanyl)propionic acid (3.12 g, 10 mmol) was dissolved in mixture of methanol (10 mL) and benzene (10 mL). Trimethylsilyl-diazomethane (10 mL, 2.0 M solution in hexane, 20 mM) was added slowly. After 1 h, the solvent was removed to give methyl 2(R)-N-tert-butoxycarbonylamino-3-(pyridin-2-ylmethylsulfanyl)-propionate as a yellow oil.

Step 3

Methyl 2(R)-N-tert-butoxycarbonylamino-3-(pyridin-2-ylmethylsulfanyl)-propionate was dissolved in dioxane and 3 equiv. of 4M HCl in dioxane was added. After stirring at room temperature for 3 h, the solvent was removed under reduced pressure to give methyl 2(R)-amino-3-(pyridin-2-ylmethylsulfanyl)propionate hydrochloride as a hygroscopic solid.

Step 4

To a mixture of methyl 2(R)-amino-3-(pyridin-2-ylmethylsulfanyl)-propionate hydrochloride (1.31 g, 5 mmol), 2,2,2-trifluoro-1-(4-fluorophenyl)ethanone (0.875 g), DIPEA (2.39 g, 18.5 mmol), in dichloromethane (20 mL) was added titanium tetrachloride (4.65 mmol) dropwise over 5 min. After stirring for 3 h at ambient temperature, additional titanium tetrachloride (0.3 mmol) was added. After an additional hour of stirring, NaCNBH$_4$ (0.973 g, 15.5 mmol) was added in methanol (10 mL). After 1 h, the reaction mixture was diluted with ethyl acetate (200 mL) and poured onto magnesium sulfate. After filtration and concentration, the residue was purified by flash chromatography to afford methyl 3-(pyridin-2-yl-methylsulfanyl)-2(R)-[2,2,2-trifluoro-1(RS)-(4-fluorophenyl)ethylamino]-propionate (640 mg, 1.59 mmol).

Step 5

To a solution of methyl 3-(pyridin-2-ylmethylsulfanyl)-2(R)-[2,2,2-trifluoro-1(RS)-(4-fluorophenyl)ethylamino]propionate (0.64 g, 1.59 mmol) in methanol (9 mL) was added 1N sodium hydroxide (4.77 mL). The resulting solution was stirred for 2 h at ambient temperature and then methanol was removed in vacuo. The residue was portioned between water and ethyl acetate. The aqueous layer was extracted twice more with ethyl acetate and the combined organic layers were dried over magnesium sulfate. Removal of the solvents provided 3-(pyridin-2-ylmethylsulfanyl)-2(R)-[2,2,2-trifluoro-1(RS)-(4-fluorophenyl)ethylamino]propionic acid (0.410 g, 1.06 mmol) as a white solid which was a mixture of diastereomers. 3-(Pyridin-2-ylmethylsulfanyl)-2(R)-[2,2,2-trifluoro-1(RS)-(4-fluorophenyl)ethylamino]propionic acid was converted to of N-(1-cyano-cyclopropyl)-3-(pyridin-2-ylmethylsulfanyl)-2(R)-[2,2,2-trifluoro-1(RS)-(4-fluorophenyl)-ethylamino]propionamide by proceeding as described in Example 2, Step 8 above. N-(1-Cyanocyclopropyl)-3-pyridin-2-ylmethanesulfanyl-2(R)-(2,2,2-trifluoro-1(S)-4-fluorophenyl-ethylamino)propionamide (95 mg) was obtained from the diasteriomeric mixture by flash chromatography and was converted to the title compound (50 mg) by proceeding as described in Example 1, Step 6 above.

NMR (CDCl$_3$): 1.16(q, 2H), 1.54(q, 2H), 3.50(dd, 2H), 3.72(dd, 1H), 3.80(b, 1H), 4.37(q, 1H), 4.57(d, 1H), 4.75(d, 1H), 7.13(t, 2H), 7.41(t, 2H), 7.47(t, 1H), 7.56(d, 1H), 7.69(s, 1H), 7.90(t, 1H), 8.67(d, 1H). MS: 507.0 (M+23), 484.9 (M+1), 483.2 (M−1).

Proceeding as described in Example 4 above, following compounds of the invention were prepared.

N-(1-cyanocyclopropyl)-3-pyridin-2-ylmethanesulfanyl-2(R)-(2,2,2-trifluoro-(RS)-phenylethylamino)propionamide. MS: 467 (M+1).

N-(1-cyanocyclopropyl)-3-pyridin-2-ylmethanesulfonyl-2(R)-(2,2,2-trifluoro-1(S)-phenylethyl-amino)propionamide. MS: 467 (M+1).

N-(1-cyanocyclopropyl)-3-pyridin-2-ylmethanesulfonyl-2(R)-(2,2,2-trifluoro-1(R)-phenylethylamino)propionamide. MS: 467 (M+1).

N-(1-cyanocyclopropyl)-3-pyridin-2-ylmethanesulfonyl-2(R)-(2,2,2-trifluoro-1(RS)-4-fluorophenylethylamino)propionamide. MS: 485 (M+1).

N-(1-cyanocyclopropyl)-3-phenylmethanesulfanyl-2(R)-(2,2,2-trifluoro-1(RS)-pyridin-2-ylethyl-amino)propionamide. MS: 437 (M+1).

N-(1-cyanocyclopropyl)-4-pyridin-2-ylsulfanyl-2(R)-(2,2,2-trifluoro-1(RS)-4-fluorophenyl-ethylamino)butyramide. MS: 453 (M+1).

N-(1-cyanocyclopropyl)-4-pyridin-2-ylsulfonyl-2(R)-(2,2,2-trifluoro-1(RS)-4-fluorophenyl-ethylamino)butyramide. MS: 485 (M+1).

N-(1-cyanocyclopropyl)-3-phenylmethanesulfonyl-2(R)-(2,2,2-trifluoro-1(RS)-pyridin-2-yl-ethylamino)propionamide. MS: 467 (M+1).

N-(1-cyanocyclopropyl)-3-pyridin-2-ylmethanesulfanyl-2(R)-(2,2,2-trifluoro-1(S)-4-fluoro-phenylethylamino)propionamide. MS: 453 (M+1).

N-(1-cyanocyclopropyl)-3-pyridin-2-ylmethanesulfanyl-2(R)-(2,2,2-trifluoro-1(R)-4-fluoro-phenylethylamino)propionamide. MS: 453 (M+1).

N-(1-cyanocyclopropyl)-3-pyridin-2-ylmethanesulfonyl-2(R)-(2,2,2-trifluoro-1(R)-4-fluoro-phenylethylamino)propionamide. MS: 485 (M+1).

N-(1-cyanocyclopropyl)-3-(1-oxopyridin-2-ylmethanesulfonyl)-2(R)-(2,2,2-trifluoro-1(S)-4-fluorophenylethylamino)propionamide. MS: 501 (M+1); 499 (M−1).

Example 5

Synthesis of N-(1-cyanocyclopropyl)-3-(pyridin-2-ylmethanesulfanyl)-2(R)-(2,2,2-trifluoro-1(RS)-phenylethylamino)propionamide

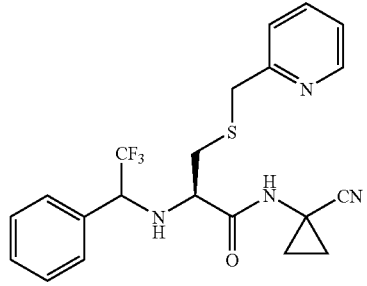

Step 1

2(R)-tert-Butoxycarbonylamino-3-(pyridin-2-ylmethylsulfanyl)propionic acid (1.644 g, 5.3 mmol) was dissolved in DMF, 1-aminocyclopropanecarbonitrile hydrochloride (747 mg, 6.3 mmol), HATU (2.4 g, 6.3 mmol) and N-methylmorpholine (2.3 mL, 21.2 mmol) were added and the reaction mixture was stirred at room temperature for 4 h. Saturated NaHCO$_3$ solution and ethyl acetate were added after stirring for 20 min at room temperature, aqueous layer was extracted by ethyl acetate. Combined organic layers was dried by MgSO$_4$ and removed under the reduced pressure. Purified by flash column (ethyl acetate) provided [1-(1-cyanocyclopropylcarbamoyl)-2(R)-(pyridin-2-ylmethylsulfanyl)ethyl]carbamic acid tert-butyl ester (1.28 g).

Step 2

[1-(1-Cyanocyclopropylcarbamoyl)-2(R)-(pyridin-2-ylmethylsulfanyl)ethyl]-carbamic acid tert-butyl ester (1.28 g, 3.4 mmol) was dissolved in THF, methanesulfonic acid (0.65 mL, 10 mmol) was added and the reaction mixture was stirred overnight at room temperature. Water (1 mL) and solid NaHCO$_3$ were added until no bubbles were observed. The product was extracted with ethyl acetate. The organic layer was dried with MgSO$_4$ and removed under the reduced pressure to get 2(R)-amino-N-(1-cyanocyclopropyl)-3-(pyridin-2-ylmethylsulfanyl)propionamide as an oil (100% yield).

Step 3

To a stirred solution of 2(R)-amino-N-(1-cyanocyclopropyl)-3-(pyridin-2-ylmethyl-sulfanyl)propionamide (110 mg, 0.4 mmol) in anhydrous THF (2 mL) were added activated 4A molecular sieves (250 mg) and N-methylmorpholine (40 mg, 0.4 mmol). After 10 min, trifluoromethanesulfonic acid 2,2,2-trifluoro-1-phenylethyl ester (152 mg, 0.4 mmol) was added and the reaction mixture was stirred at room temperature for 2 days. The reaction mixture was filtered and the filtrate was concentrated and the residue was purified by flash column chromatography to afford a mixture of N-(1-cyanocyclopropyl)-3-(pyridin-2-ylmethylsulfanyl)-2(R)-(2,2,2-trifluoro-1(R)-phenylethylamino)propionamide and N-(1-cyanocyclopropyl)-3-(pyridin-2-ylmethylsulfanyl)-2(R)-(2,2,2-trifluoro-1(S)-phenylethylamino)propionamide (65 mg). LC-MS: 433.3 (M−1), 435.1 (M+1), 457.1 (M+Na).

Example 6

Synthesis of N-(1-cyanocyclopropyl)-3-(2-difluoromethoxyphenylmethanesulfonyl)-2(R)-[2,2,2-trifluoro-1(S)-(4-fluorophenyl)ethylamino]propionamide

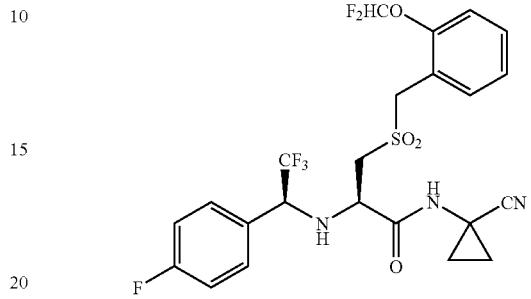

Step 1

A dried 50 mL of flask was charged sodium hydride, 60% dispersion in mineral oil (624 mg, 15.6 mmol) under N$_2$ and then washed with dried hexane (20 mL) twice. Dried ethyl ether (10 mL) was added and a solution of 2,2,2-trifluoro-1 (RS)-(4-fluorophenyl)ethanol (90% ee) (2.5 g, 12.89 mmol) in ethyl ether (10 mL) was added at 0° C. After completion of addition, the reaction mixture was allowed to warm up to room temperature and stirred for 1 h. A solution of trifluoromethanesulfonyl chloride (3.28 g, 19.5 mmol) in ethyl ether (10 mL) was added at 0° C. After completion of addition, the reaction was allowed to warm up to room temperature and stirred for 1 h. The solvent was removed under rot-vap and diluted with hexane (150 mL) and washed with a saturated NaHCO$_3$ n and brine. After drying with MgSO$_4$, the organic solvent was removed to give trifluoro-methanesulfonic acid 2,2,2-trifluoro-1(RS)-(4-fluorophenyl)ethyl ester (3.15 g) (90% ee) as a colorless oil which was used in the next step without further purification.

Step 2

Into a stirred suspension of 2(R)-amino-3-(2-difluoromethoxyphenylmethanesulfanyl)-propionic acid (277 mg, 1 mmol) in DCM (3 mL) was added DIPEA (323 mg, 2.5 mmol) and trifluoromethanesulfonic acid 2,2,2-trifluoro-1 (RS)-(4-fluorophenyl)ethyl ester (489 mg, 1.5 mmol) (90% ee) at 25° C. After 12 h, HPLC showed diastereomeric mixture of two major products 3-(2-difluoromethoxyphenylmethanesulfanyl)-2(R)-[2,2,2-trifluoro-1(RS)-(4-fluorophenyl)ethylamino]-propionic acid and 1(RS)-(4-fluorophenyl)-2,2,2-trifluoroethane 3-(2-difluoromethoxyphenylmethanesulfanyl)-2(R)-[2,2,2-trifluoro-1(RS)-(4-fluorophenyl)ethylamino]propionate (t=4.177, t=4.852). The reaction mixture was diluted with ethyl ether (150 mL) and washed with 1N HCl solution and brine. After drying with MgSO$_4$, the solvent was removed and the residue was purified by prep-HPLC to give 3-(2-difluoromethoxy-phenylmethanesulfanyl)-2(R)-[2,2,2-trifluoro-1(RS)-(4-fluorophenyl)ethylamino]propionic acid (178 mg) and 1(RS)-(4-fluorophenyl)-2,2,2-trifluoroethane 3-(2-difluoromethoxyphenylmethanesulfanyl)-2(R)-[2,2,2-trifluoro-1(RS)-(4-fluorophenyl)-ethylamino]propionate (203 mg)

Step 3

To a solution of 1(RS)-(4-fluorophenyl)-2,2,2-trifluoroethane 3-(2-difluoromethoxy-phenylmethanesulfanyl)-2(R)-

[2,2,2-trifluoro-1(RS)-(4-fluorophenyl)ethylamino]propionate in THF (2 mL) and MeOH (1 mL) was added 1N solution of LiOH (1 mL) at 25° C. After 30 min, the solvent was removed and the residue was diluted with water (10 mL) and extracted with hexane to remove alcohol. The water phase was acidified by 1N HCl to pH=1-2 and extracted with ethyl ether (120 mL). After drying with MgSO₄, the solvent was removed under rot-vap, to give 3-(2-difluoromethoxy-phenylmethaneuslfanyl)-2(R)-[2,2,2-trifluoro-1(RS)-(4-fluorophenyl)ethylamino]-propionic acid.

Step 4

In to a stirred solution of 3-(2-difluoromethoxyphenylmethanesulfanyl)-2(R)-[2,2,2-trifluoro-1(RS)-(4-fluorophenyl)ethylamino]propionic acid (153 mg, 0.338 mmol) in MeOH (10 mL) was added a solution of OXONE® (314 mg, 0.51 mmol) in water (10 mL) at room temperature. After stirring for 30 min, the methanol was removed and extracted with ethyl acetate (100 mL), then washed with brine and dried with MgSO₄. Removal of the solvent gave 3-(2-difluoromethoxy-phenylmethanesulfonyl)-2(R)-[2,2,2-trifluoro-1(RS)-(4-fluorophenyl)-ethylamino]propionic acid (157 mg).

Step 5

To a solution of 3-(2-difluoromethoxyphenylmethanesulfonyl)-2(R)-[2,2,2-trifluoro-1(RS)-(4-fluorophenyl)ethylamino]propionic acid (157 mg, 0.325 mmol) in DMF (5 mL) was added 1-aminocyclopropanecarbonitrile hydrochloride (46.4 mg, 0.39 mmol), HATU (186.3 mg, 0.49 mmol) and DIPEA (63.2 mg, 0.49 mmol). After 1 h, the reaction mixture was extracted with ethyl acetate (100 mL) and washed with satured NaHCO₃ and brine. After driying with MgSO₄, the solvent was removed and the residue was purified by column chromatograph yield the title compound (125 mg).

HNMR (CDCl₃): 7.69(1H, s), 7.5-7(8H, m), 6.5(1H, t, J=58.8 Hz), 4.47(2H, dd), 4.25(1H, dd), 3.65-3.6(1H, m), 3.45-3.35(1H, m), 3.3-3.1(1H, m), 1.2-1.1(2H, m), 1.01-0.9 (2H, m). LC-MS: 548(M−1), 550.1(M+1), 572(M+Na).

Example 7

Synthesis of N-(4-cyano-1,1-dioxohexahydro-1λ⁶-thiopyran-4-yl)-3-(2-difluoromethoxy-phenylmethanesulfonyl-2(R)-(2,2,2-trifluoro-1(S)-4-fluorophenylethylamino)propionamide

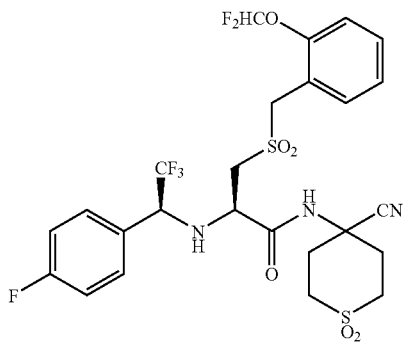

Proceeding as described in Example 6, Step 5 above, but substituting 1-aminocyclopropane-carbonitrile hydrochloride with 4-amino-4-cyanotetrahydrothiopyran provided N-(4-cyano-tetrahydrothiopyran-4-yl)-3-(2-difluoromethoxyphenylmethanesulfanyl-2(R)-(2,2,2-trifluoro-1 (RS)-4-fluorophenylethylamino)propionamide which was converted to N-(4-cyanotetrahydrothiopyran-4-yl)-3-(2-difluoromethoxyphenylmethanesulfonyl-2(R)-(2,2,2-trifluoro-1(RS)-4-fluorophenyl-ethylamino)propionamide as described in Example 3 above. The title compound was isolated via column chromatography.

HNMR (CDCl₃): 7.69(1H, s), 7.5-7(8H, m), 6.5(1H, t, J=74 Hz), 4.6(2H, dd), 4.2(1H, d), 3.8(1H, m), 3.5-2.8(4H, m), 2.7-1.9(3H, m), 1.8-1.4(2H, m), 1.2-1.1(2H, m). LC-MS: 640.2(M−1), 641.8(M+1)

Example 8

Synthesis of N-(4-cyanotetrahydropyran-4-yl)-3-(2-difluoromethoxyphenylmethane-sulfonyl-2(R)-(2,2,2-trifluoro-1(S)-4-fluorophenylethylamino)propionamide

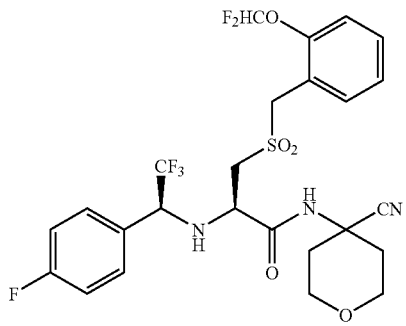

Proceeding as described in Example 6, Step 5 above, but substituting 1-aminocyclopropane-carbonitrile hydrochloride with 4-amino-4-cyanotetrahydropyran (prepared as described in PCT application publication No. WO 01/19816, page 141, Example 2) provided N-(4-cyanotetrahydropyran-4-yl)-3-(2-difluoromethoxyphenylmethanesulfanyl-2(R)-(2,2,2-trifluoro-1(RS)-4-fluorophenylethylamino)propionamide which was converted to N-(4-cyanotetrahydropyran-4-yl)-3-(2-difluoromethoxyphenylmethanesulfonyl-2(R)-(2,2,2-trifluoro-1(RS)-4-fluorophenylethylamino)propionamide as described in Example 3 above. The title compound was isolated via column chromatography.

HNMR (CDCl₃): 7.69(1H, s), 7.5-7(8H, m), 6.6(1H, t, J=73.6 Hz), 4.63(2H, dd), 4.38(1H, m), 4-3.2(8H, m), 2.3-2.1 (2H, dd), 1.8-1.5(2H, m). LC-MS: 592.2(M−1), 593.8(M+1),

Example 9

Synthesis of N-(1-cyanocyclopropyl)-3-(6-trifluoromethylpyridin-2-ylmethanesulfonyl)-2(R)-(2,2,2-trifluoro-1(S)-phenylethylamino)propionamide

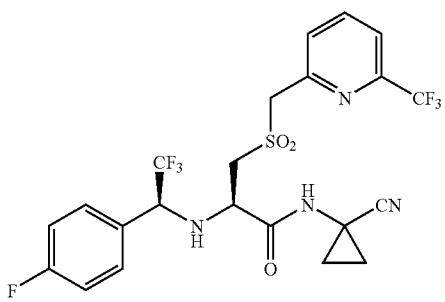

Step 1

6-Trifluoromethylpyridine-2-carboxylic acid was prepared as described in (Schlosser, M and Marull, M. *Eur. J Org. Chem.* 2003, 1569-1575.

Step 2

To a suspension of 6-trifluoromethylpyridine-2-carboxylic acid (2.53 g, 13.2 mmol) in THF (50 mL) cooled to −5° C. was added triethylamine (1.84 mL, 13.2 mmol) followed by addition of ethyl chloroformate (1.26 mL, 13.2 mmol) and the reaction mixture was stirred for 30 min at 0° C. Lithium borohydride (718 mg, 33 mmol) was added in portions, maintaining the temperature below −5° C. After the addition was complete, the reaction was allowed to warm to room temperature and stirred for 1 h. Temperature was lowered to −5° C. and methanol (10 mL) was added followed by addition of aqueous sodium hydroxide (10 mL, 10%). After the addition of ethyl acetate (50 mL) and water (40 mL), dilute hydrochloric acid was added to obtain pH=5.0. After washing aqueous layer thoroughly with ethyl acetate the combined organic extracts were dried over MgSO$_4$ and concentrated. Purification by flash column (30% EtOAc-Hexane) gave (6-trifluoromethylpyridin-2-yl)methanol (760 mg) as an oil.

Step 3

(6-Trifluoromethylpyridin-2-yl)methanol (760 mg, 4.3 mmol) was dissolved in CH$_2$Cl$_2$ and thionyl chloride was added slowly at room temperature. The reaction mixture was stirred at room temperature for 4 h. Solvent was removed under the reduced pressure, the pH was adjusted to 5, and the product was extracted with EtOAc. Purification by flash column (5% EtOAc-Hexane) gave 2-chloromethyl-6-trifluoromethylpyridine (200 mg) as a white solid.

Step 4

2(R)-N-tert-butoxycarbonylamino-3-(pyridin-2-ylmethylsulfanyl)propionic acid was prepared as described in Example 4, Step 1.

Step 5

2(R)-tert-Butoxycarbonylamino-3-(6-trifluoromethylpyridin-2-ylmethylsulfanyl)-propionic acid (760 mg, 2 mmol) was dissolved in DMF and 1-aminocyclopropanecarbonitrile hydrochloride (284 mg, 2.4 mmol), HATU (912 mg, 2.4 mmol) and N-methylmorpholine (0.9 mL, 8 mmol) were added. After stirring for 4 h at room temperature, saturated NaHCO$_3$ solution and ethyl acetate were added and stirring was continued for an additional 20 min. The reaction mixture was extracted with ethyl acetate and the combined organic layer was dried by MgSO$_4$, filtered, and concentrated under reduced pressure. Purification by flash column (100% CH$_2$Cl$_2$) gave [1-(1-cyano-cyclopropylcarbamoyl)-2(R)-(6-trifluoromethylpyridin-2-ylmethylsulfanyl)ethyl]carbamic acid tert-butyl ester (340 mg) as an oil.

Step 6

[1-(1-Cyanocyclopropylcarbamoyl)-2(R)-(6-trifluoromethylpyridin-2-ylmethyl-sulfanyl)ethyl]-carbamic acid tert-butyl ester (340 mg) was dissolved in THF and 3 eq. of methanesulfonic acid was added. After stirring overnight, water (1 mL) was added and solid NaHCO$_3$ was added until no bubbles were observed. The reaction mixture was extracted with ethyl acetate. The organic layer was dried with MgSO$_4$, filtered and concentrated under the reduced pressure to get 2(R)-amino-N-(1-cyanocyclopropyl)-3-(6-trifluoromethylpyridin-2-ylmethylsulfanyl)propionamide as an oil.

Step 7

(R)-Amino-N-(1-cyanocyclopropyl)-3-(6-trifluoromethylpyridin-2-ylmethylsulfanyl)-propionamide (86 mg, 0.25 mmol), NMM (0.054 mL, 0.5 mmol) and molecular sieves were added in THF. After 5 min, trifluoromethanesulfonic acid 2,2,2-trifluoro-1-(4-fluorophenyl)ethyl ester (122 mg, 0.37 mmol) was added at room temperature. The reaction mixture was stirred at room temperature overnight. Solvent was removed under the reduced pressure and N-(1-cyanocyclo-propyl)-2(R)-[2,2,2-trifluoro-1(RS)-(4-fluorophenyl)ethylamino]-3-(6-trifluoromethylpyridin-2-ylmethyl-sulfanyl)propionamide was purified by flash column (30% EtOAc-Hexane) to get (40 mg) of pure product as an oil. LC-MS: 521 (M+1), 543 (M+23), 519 (M−1). This was converted to N-(1-cyanocyclopropyl)-2(R)-[2,2,2-trifluoro-1(RS)-(4-fluorophenyl)ethylamino]-3-(6-trifluoromethylpyridin-2-ylmethyl-sulfonyl)propionamide compound as described in Example 3 above. Two diastereomers are separated by flash column (1% MeOH—CH$_2$Cl$_2$) to give the title compound.

NMR (DMSO-d$_6$): 0.74(1H, m), 0.97(1H, m), 1.33(2H, m), 3.27(1H, m), 3.45(2H, m), 3.72(1H, m), 4.39(1H, m), 4.93(2H, m), 7.19(2H, t), 7.42(2H, m), 7.77(1H, d), 7.92(1H, d), 8.15(1H, t), 9.01(1H, s). LC-MS: 553(M+1), 575(M+23), 551 (M−1).

Example 10

Synthesis of N-(1-cyanocyclopropyl)-3-pyrazin-2-ylmethanesulfonyl-2(R)-(2,2,2-trifluoro-1(S)-4-fluorophenylethylamino)propionamide and N-(1-cyanocyclopropyl)-3-pyrazin-2-ylmethane-sulfonyl-2(R)-(2,2,2-trifluoro-1(R)-4-fluorophenylethylamino)propionamide

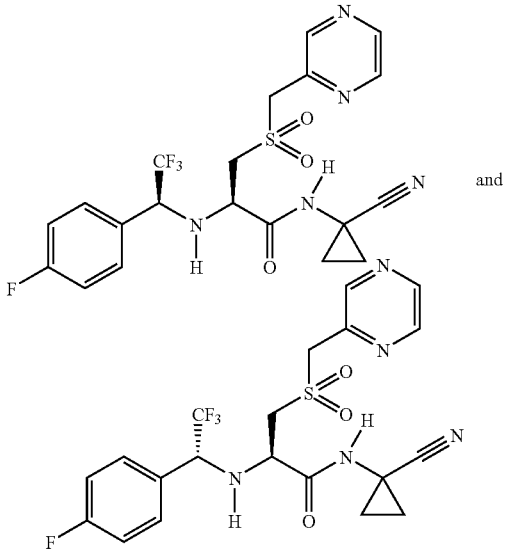

Step 1

A mixture of 2-methylpyrazine (7.0 g, 74.4 mmol), N-chlorosuccinamide (12.6 g, 94.4 mmol), and benzoyl peroxide (0.1 g, 0.41 mmol) in carbon tetrachloride (200 mL) was heated to reflux for 16 h. The resulting dark heterogeneous solution was filtered, the filtrate concentrated, and the residue purified by flash chromatography (EtOAC/hexanes) to give 2-chloromethyl-pyrazine.

Step 2

(Boc-NH-Cys-OH)$_2$ (1.04 g, 2.35 mmol) was dissolved in DMF (8.5 mL) and after adding tris (2-carboxyethyl) phosphine hydrochloride (0.81 g, 2.82 mmol) the resulting slight suspension was stirred for 10 min. 5N KOH (5.65 ml) was added dropwise over a 20 min period (slight exotherm noticed) and the resulting solution was stirred for 6 h at ambient temperature. A solution of 2-chloromethylpyrazine (1.16 g, 7.07 mmol) in DMF (2 mL) was added and the reaction mixture was allowed to stir overnight. The pH was adjusted to 4 with 1N HCl and the product was extracted with ethyl acetate. The combined organic layers were washed with brine and dried over MgSO$_4$. After concentration, the crude 2(R)-tert-butoxycarbonylamino-3-(pyrazin-2-ylmethanesulfonyl)-propionic acid (1.42 g, 4.53 mmol) was used in the next step.

Step 3

(R)-tert-Butoxycarbonylamino-3-(pyrazin-2-ylmethanesulfonyl)propionic acid (1.42 g, 4.53 mmol) was dissolved in mixture of MeOH (10 mL) and toluene (33 mL) and Me$_3$SiCHN$_2$ (2.0 M solution in hexanes, 3.06 ml) was added dropwise over 10 min. After stirring the reaction mixture overnight, the solvent was removed and the resulting residue was purified by flash chromatography with EtOAc/hexanes as eluent to afford methyl 2(R)-tert-butoxycarbonylamino-3-(pyrazin-2-ylmethanesulfonyl)propionate (0.755 g).

Step 4

Methyl 2(R)-tert-butoxycarbonylamino-3-(pyrazin-2-ylmethanesulfonyl)propionate was dissolved in THF (5 mL) and a solution of HCl/dioxane (4.0 M, 2.9 mL) was added. After stirring for 48 h, the solvent was removed in vacuo and the residue was precipitated with diethyl ether and dried under vacuum to give methyl 2(R)-amino-3-(pyrazin-2-ylmethanesulfonyl)propionate which was converted to the title compounds utilizing the procedure described in Example 4 above.

N-(1-cyanocyclopropyl)-3-pyrazin-2-ylmethanesulfonyl-2(R)-(2,2,2-trifluoro-1(S)-4-fluorophenylethylamino)propionamide. $^1$H NMR (400 MHz, DMSO) 9.1 (s, 1H), 8.75 (d, 6.5 Hz, 1H), 7.48 (m, 2 H), 7.27 (m, 2 H), 4.92 (m, 2 H), 4.42 (m, 2 H), 3.80 (m, 1 H), 3.90 (dd, 4.5, 11.2 Hz, 2 H), 3.45 (m, 2H), 1.40 (m, 2 H), 1.05 (m, 1 H), 0.87 (m, 1 H). MS: 484.0 (M−1).

N-(1-cyanocyclopropyl)-3-pyrazin-2-ylmethane-sulfonyl-2(R)-(2,2,2-trifluoro-1(R)-4-fluorophenylethylamino)propionamide. $^1$H NMR (400 MHz, DMSO) 9.05 (s, 1H), 8.75 (d, 6.5 Hz, 1H), 7.55 (m, 2 H), 7.32 (m, 2 H), 4.95 (dd, 2 H), 4.45 (m, 2 H), 3.80 (m,1H), 3.45 (m, 2H) 0.95-1.40 (m, 4H). MS: 484.0 M−1).

N-(1-cyanocyclopropyl)-3-pyrazin-2-ylmethanesulfanyl-2(R)-(2,2,2-trifluoro-1(R)-4-fluorophenyl-ethylamino)propionamide. MS: 454 (M+1).

N-(1-cyanocyclopropyl)-3-pyrazin-2-ylmethanesulfanyl-2(R)-(2,2,2-trifluoro-1(S)-4-fluorophenyl-ethylamino)propionamide. MS: 454 (M+1).

Example 11

Synthesis of N-(1-cyanocyclopropyl)-3-(pyridin-2-ylmethanesulfonyl)-2-(2,2,2-trifluoro-1-phenyl-1-trifluoromethylethylamino)propionamide

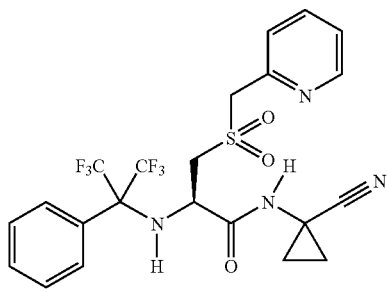

Step 1

Potassium hydride (1.05 g, 26.2 mmol) was suspended in ethyl ether (100 mL) and cooled in and ice water bath. 1,1,1,3,3,3-Hexafluoro-2-phenylpropan-2-ol (4.0 g, 16.4 mmol) in ethyl ether (20 mL) was added over a 5 min and the solution was stirred for an hour. Triflic anhydride (4.62 g, 16.4 mmol) was added neat over 5 min and the reaction mixture was allowed to warm to ambient temperature overnight. The reaction mixture was quenched with water and diluted with ether (300 mL). The organic layer was washed with saturated sodium bicarbonate and brine and dried over magnesium sulfate to give trifluoromethanesulfonic acid 2,2,2-trifluoro-1-phenyl-1-trifluoromethyl-ethyl ester Step 2

2(R)-Amino-N-(1-cyanocyclopropyl)-3-(pyridin-2-ylmethylsulfanyl)propionamide and trifluoromethanesulfonic acid 2,2,2-trifluoro-1-phenyl-1-trifluoromethyl-ethyl ester were converted to N-(1-cyanocyclopropyl)-3-(pyridin-2-yl-methylsulfanyl)-2(R)-(2,2,2-trifluoro-1-phenyl-1-trifluoromethylethylamino)propionamide utilizing the procedure described in reference J, step 3 above.

Step 3

N-(1-Cyanocyclopropyl)-3-(pyridin-2-ylmethylsulfanyl)-2(R)-(2,2,2-trifluoro-1-phenyl-1-trifluoromethylethylamino)propionamide was oxidized to the title compound utilizing a procedure outlined in Example 1, step 5 above.

Example 12

Synthesis of N-(1-cyanocyclopropyl)-3-cyclopropylmethanesulfonyl-2(R)-(2,2,2-trifluoro-1(S)-4-fluorophenylethylamino)propionamide

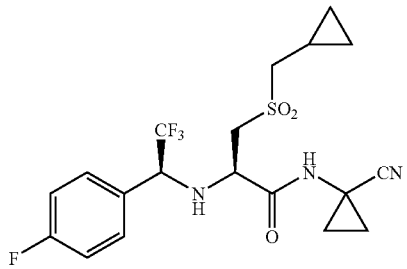

Step 1

A solution of 2(R)-amino-3-cyclopropylmethylsulfanyl-propan-1-ol (3.2 g, 20.0 mmol), prepared as described in Example 2, Steps 1 and 2 above, and trifluoroacetaldehyde methyl hemiacetal (2.6 g, 20.0 mmol) in toluene (20 mL) was heated at reflux with Dean Stark trapping of water for 24 h. The reaction mixture was concentrated to give 4-cyclopropylmethylsulfanylmethyl-2-trifluoromethyloxazolidine (4.18 g) as a pale yellow oil.

Step 2

Part A: A solution of 4-cyclopropylmethylsulfanylmethyl-2-trifluoromethyloxazolidine (4.18 g, 17.0 mmol) in anhydrous tetrahydrofuran (34 mL) was cooled in an ice water bath and treated with chlorotrimethylsilane (2.58 mL, 20.4 mmol) and lithium bis(trimethylsilyl)amide (20.4 mL of 1.0 M solution in tetrahydrofuran). The reaction mixture was allowed to stir under ice bath cooling for 30 minutes and then at room temperature for 1 hour.

Part B: A solution of 4-fluorobromobenzene (5.6 mL, 51 mmol) in anhydrous tetrahydrofuran (100 mL) was cooled to −78° C., treated with n-butyllithium (31.9 mL of 1.6M solution in hexanes, and allowed to stir for 15 min. The solution from Part A was transferred by cannula to this reaction mixture at −78° C. over 10 min. Stirring at −78° C. for 2 h was followed by addition of HCl (34 mL 1N), then the reaction mixture was allowed to warm to room temperature. Potassium hydroxide (9 mL of 25% solution in water) was added, but the resulting mixture appeared to have the trimethylsilyl ether protecting group still intact. Therefore, the mixture was acidified with more 1N HCl (20 mL) before it was extracted with ethyl acetate. The combined organic layers were dried over anhydrous sodium sulfate, concentrated, and chromatographed using an 8:1 to 5:1 gradient of hexane:ethyl acetate to give 3-cyclopropylmethylsulfanyl-2(R)-[2,2,2-trifluoro-1 (S)-(4-fluoro-phenyl)-ethylamino]propan-1-ol (2.36 g) and 3-cyclopropylmethylsulfanyl-2(R)-[2,2,2-trifluoro-1(R)-(4-fluorophenyl)-ethylamino]propan-1-ol (370 mg).

Step 3

Solutions of 0.41M periodic acid in dry acetonitrile and 0.02M chromium trioxide in dry acetonitrile were prepared 3 hours ahead, with stirring at room temperature. Periodic acid solution (36.5 mL) was chilled in an ice/acetone bath and treated first with chromium trioxide solution (3.6 mL), then a solution of 3-cyclopropylmethylsulfanyl-2(R)-[2,2,2-trifluoro-1S-(4-fluorophenyl)-ethylamino]propan-1-ol in acetonitrile (18 mL). The reaction was monitored by reverse phase HPLC and portions of the chromium trioxide solution were added (2 mL at 2 h reaction time, 2 mL at 4 h reaction time). After 1 more hour reaction time, the reaction was found to be complete by HPLC analysis. Isopropanol (50 mL) was added. The reaction mixture was allowed to warm to room temperature and then was concentrated. The resulting solids were partitioned between ethyl acetate (30 mL) and saturated aqueous $KH_2PO_4$ (30 mL). The aqueous layer was extracted with ethyl acetate and the combined organic layers were washed with brine and dried over anhydrous sodium sulfate. Removal of solvent gave 3-cyclopropylmethylsulfonyl-2(R)-[2,2,2-trifluoro-1(S)-(4-fluorophenyl)ethylamino]propionic acid (0.82 g ) as an amber oil which was converted to the title compounds as described in Example 2, step 8 above.

NMR ($CDCl_3$, 400 MHz): δ 7.61 (1H, br s), 7.42 (2H, dd, J=8.4 Hz, 5.6 Hz), 7.15 (2H, t, J=8.8 Hz), 4.41 (1H, q, J=7.2 Hz), 3.68 (1H, m), 3.62 (1H, dd, J=14.4 Hz, 6.4 Hz), 3.41 (1H, dd, J=14.4 Hz, 4.0 Hz), 3.06 (2H, d, J=6.8 Hz), 1.60 (2H, m), 1.24 (3H, m), 0.81 (2H, m), 0.48 (2H, m). MS: 448.3 (M+1). M+1=429.9; M+23=451.9; M−1=428.0.

N-(1-cyanocyclopropyl)-3-cyclopropylmethanesulfonyl-2(R)-(2,2,2-trifluoro-1(s)-3,4-difluorophenylethylamino) propionamide. MS: 466.1 (M+1).

N-(1-cyanocyclopropyl)-3-cyclopropylmethanesulfonyl-2(R)-(2,2,2-trifluoro-1(s)-3,4,5-trifluoro-phenylethylamino) propionamide. MS: 484.0 (M+1).

Example 13

Synthesis of N-(1-cyanocyclopropyl)-3-phenyl-methanesulfonyl-2(R)-(2,2,2-trifluoro-1(S)-methyl-ethylamino)propionamide

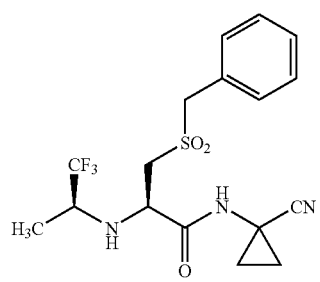

To a cold (0° C.), stirred mixture of 3-phenylmethanesulfanyl-2(R)-(2,2,2-trifluoro-1(RS)-hydroxyethylamino)propionic acid methyl ester (162 mg, 0.5 mmol) prepared as described in Example 1 above, in dichlomethane (2 mL) was added 2.0 M solution of trirethylaluminum in toluene dropwise via a microsyringe and the reaction mixture was allowed to warm to rt over 2 h. After stirring at rt for 2 h, the reaction was quenched with water, and extracted with dichloromethane. The combined organic extracts were dried ($MgSO_4$), concentrated under reduced pressure, and the residue was purified by flash chromatography on silica gel (eluted with 1:6 EtOAc/hexanes) to yield the title compound (55 mg) as a mixture of diastereomers in a 8:2 ratio. MS: 404.1 (M+1).

Example 14

Synthesis of N-(4-cyanocyclopropyl)-3-(4-fluorophenylmethanesulfonyl)-2(R)-(2,2,2-trifluoro-1 (S)-4-fluorophenylethylamino)propionamide

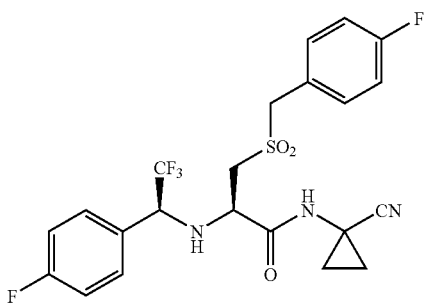

Step 1

L-cysteine (15.97 g) was dissolved in a mixture of 1.0 M aqueous sodium hydroxide (265 mL) and 1,4-dioxane (265 mL). 4-Fluorobenzylbromide (24.85 g) was added dropwise over 30 min. After stirring overnight, dioxane was removed and the pH of the residual aqueous solution was adjusted to pH-6 with 3M hydrochloric acid. A white precipitate began to form immediately upon addition of the acid and additional water (150 mL) was added to aid stirring of the thick suspension. The reaction mixture was cooled to 0° C. for 1 h and the precipitates were collected by filtration and washed with cold water, $Et_2O$, and hexane, and dried under high vacuum to give 2(R)-amino-3-(4-fluorobenzylsulfanyl)-propionic acid (28.68 g) as a white solid.

Step 2

A 1000 mL 3-neck round bottom flask fitted with a mechanical stirrer, reflux condenser, addition port, and nitrogen inlet was charged with a 1.0 M solution of lithium aluminum hydride (200 mL) in THF and anhydrous THF (200 mL). The solution was cooled in an ice/water bath and 2(R)-amino-3-(4-fluorobenzylsulfanyl)-propionic acid (24.08 g) was added with rapid stirring in small portions over 15 min. The ice bath was removed and the reaction mixture was heated to reflux overnight. After cooling the reaction mixture to room temperature, saturated aqueous potassium carbonate (50 mL) was added dropwise over 1 h. The solids were filtered off and the filter cake was washed with THF. The combined filtrate was dried over anhydrous $MgSO_4$ and concentrated to give 2(R)-amino-3-(4-fluoro-benzylsulfanyl)-propan-1-ol (16.16 g) as a pale amber resin.

Step 3

2(R)-Amino-3-(4-fluorobenzylsulfanyl)propan-1-ol (16.15 g), 4-dimethylamino-pyridine (554 mg), and triethylamine (16.7 mL) were weighed into a 1000 mL round bottom flask fitted with a stir bar, 250 mL addition funnel, septum, and nitrogen inlet. Methylene chloride (150 mL) was added to give a clear pale amber solution. A solution of tert-butyldimethylsilyl chloride (12.54 g) in $CH_2Cl_2$ (100 mL) was added dropwise over 40 min. After stirring overnight, the reaction mixture was poured into water and the organic phase was separated, dried over anhydrous $MgSO_4$ and removed the solvent on rotavap to give 2-(tert-butyldimethylsilanyloxy)-1(R)-(4-fluoro-benzylsulfanylmethyl)ethylamine (25.92 g) as a clear yellow oil.

Step 4

2(tert-Butyldimethylsilanyloxy)-1(R)-(4-fluorobenzylsulfanylmethyl)ethylamine (25.92 g) and trifluoroacetaldehyde methyl hemiacetal [10.78 g, Avocado, 95% technical grade] were weighed into a 1000 mL round bottom flask fitted with a Dean-Stark trap with condenser. Toluene (500 mL) was added and the reaction mixture was refluxed the reaction under anhydrous conditions overnight. The solvent was removed and the residue was purified by flash chromatography on silica gel using 9:1 hexane:EtOAc eluent to obtain [2-(tert-butyldimethylsilanyloxy)-1(R)-(4-fluorobenzylsulfanylmethyl)ethyl]-(2,2,2-trifluoromethyl-ethylidine)amine (21.25 g) as a clear yellow liquid.

Step 5

A solution of 4-fluoro-1-bromopyridine (1.88 g) was weighed into an oven-dried 100 mL flask fitted with a stir bar, septum, and nitrogen inlet in anhydrous THF (20 mL) was cooled to −78°. n-Butyllithium in hexanes (4.2 mL of a 2.5M solution) was added dropwise and the reaction mixture was stirred the reaction at −78° for 30 min. A solution of [2-(tert-butyldimethyl-silanyloxy)-1(R)-(4-fluorobenzylsulfanylmethyl)ethyl]-(2,2,2-trifluoromethylethylidine)amine in anhydrous THF (13.7 mL of a 0.366M solution) was added dropwise over 15 min. After stirring at −78° 2 h, the reaction mixture was poured into a vigorously stirred mixture of 250 mL water, 250 mL crushed ice, 25 mL saturated aqueous $NH_4Cl$, and 250 mL EtOAc. The organic layer was separated and the aqueous phase was extracted with EtOAc. The combined extracts were washed with brine and dried over $MgSO_4$. The solvent was removed and the residue was dissolved in THF (20 mL) and and stirred in an ice/water bath. Tetrabutylammonium fluoride (5.25 mL of a 1.0 M solution in THF) was added dropwise over 15 min. After stirring for 2 h in in ice bath, the reaction mixture was poured into a vigorously stirred mixture of 250 mL water, 250 mL crushed ice, 25 mL saturated aqueous ammonium chloride and 250 mL EtOAc and allowed to stand overnight. The organic layer was separated, washed with brine, and dried over $MgSO_4$. After concentration, the residue was purified by flash chromatography on 250 $cm^3$ silica gel using 5% $Et_2O/CH_2Cl_2$ eluent to obtain 3-(4-fluorobenzylsulfanyl)-2(R)-[2,2,2-trifluoro-1(S)-(4-fluorophenyl)-ethylamino]-propan-1-ol (822 mg) as a clear yellow resin.

Step 6

A 500 mL round bottom flask was charged with 10.2 mL of a stock solution of 25 mg chromium(VI) oxide in 25 mL HPLC grade acetonitrile containing 0.75% v/v water and 46 mL of a stock solution of 10.0 g periodic acid in 100 mL HPLC grade acetonitrile containing 0.75% v/v water. HPLC grade acetonitrile (50 mL, 0.001% $H_2O$) and HPLC grade acetonitrile (50 mL) containing 0.75% v/v water) were added and the solution was cooled in an ice/water bath. A solution of 3-(4-fluorobenzylsulfanyl)-2(R)-[2,2,2-trifluoro-1(S)-(4-fluorophenyl)ethylamino]-propan-1-ol (530 mg) in HPLC grade acetonitrile (8.2 mL containing 0.001% $H_2O$) was added over 30 min, maintaining the temperature below 5°. After stirring at 0° C. for 3 h, the reaction mixture was quenched with 2-propanol (10 mL) and stirred 30 min at 0° C. Phosphate buffer 50 mL of 0.40M pH 4) was added and the flask was removed from the ice bath and the organic solvent was removed on a rotary evaporator at 20°. The aqueous mixture was stirred with EtOAc and sufficient water to dissolve the solids. The organic phase was separated, dried over anhydrous $MgSO_4$, and removed to obtain 3-(4-fluorophenylmethanesulfonyl)-2(R)-[2,2,2-trifluoro-1(S)-(4-fluorophenyl)ethylamino]-propionic acid (489 mg) as an amber resin.

Step 7

3-(4-Fluorophenylmethanesulfonyl)-2(R)-[2,2,2-trifluoro-1(S)-(4-fluorophenyl)-ethylamino]propionic acid (76 mg) and 1-aminocyclopropanecarbonitrile hydrochloride (23 mg) were weighed into a 4 mL vial fitted with a stir bar and cap. DMF (600 µL) was added and the reaction mixture was irred to obtain a clear amber solution. Diisopropylethylamine (105 µL) and O-(7-azabenzotriazol-1-yl)-1,1,3,3-tetramethyluronium hexafluorophosphate (83 mg) were added and the vial was flushed with nitrogen and sealed with the cap. After 2 h, the reaction mixture was diltuted with 15 mL EtOAc and washed with 1.0M aqueous $KHSO_4$, water, saturated aqueous $NaHCO_3$, and brine, and dried over anhydrous $MgSO_4$. The solvent was removed and the residue was purified the residue by flash chromatography on 22 $cm^3$ silica gel using 3:1 $CH_2Cl_2$:EtOAc eluent to give the title compound (44 mg) as a white solid.

Example 15

Synthesis of N-(4-cyano-1,1-dioxohexahydro-1$\lambda^6$-thiopyran-4-yl)-3-(4-fluorophenyl-methanesulfonyl)-2(R)-(2,2,2-trifluoro-1(S)-4-fluorophenylethylamino)propionamide

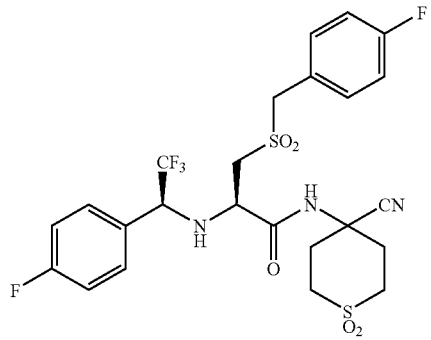

Step 1

3-(4-Fluorophenylmethanesulfonyl)-2(R)-[2,2,2-trifluoro-1(S)-(4-fluorophenyl)-ethylamino]propionic acid (146 mg) and 4-aminotetrahydrothiopyran-4-carbonitrile (104 mg) were weighed into a 4 mL vial fitted with a stir bar and cap and DMF (2 mL) was added to give a dark amber solution. Diisopropylamine (0.23 mL) and O-(7-azabenzotriazol-1-yl)-1,1,3,3-tetramethyluronium hexafluorophosphate (271 mg) were added and the vial was flushed the vial with nitrogen and sealed with the cap. After 1 h, the reaction mixture was diluted with a 9:1 mixture of $CH_2Cl_2$:EtOAc (40 mL)) and washed with 1.0M aqueous $KHSO_4$, water, a 1:1 $H_2O$:

saturated aqueous NaHCO₃, and brine and dried over anhydrous MgSO₄. After concentration, the residue was purified by flash chromatography on 20 cm³ silica gel using 9:1 CHCl₃: EtOAc eluent to give the N-(4-cyanotetrahydrothiopyran-4-yl)-3-(4-fluorophenylmethanesulfonyl)-2(R)-(2,2,2-trifluoro-1(S)-4-fluorophenylethylamino)-propionamide (30 mg) as a beige solid.

Step 2

N-(4-cyanotetrahydrothiopyran-4-yl)-3-(4-fluorophenylmethanesulfonyl)-2(R)-(2,2,2-trifluoro-1(S)-4-fluorophenylethylamino)propionamide (24 mg) was weighed into a 25 mL pear flask fitted with a stir bar and vented cap. Methanol (4.75 mL) was added and the reaction mixture was stirred at 50° C. to obtain a clear colorless solution. OXONE® (0.43 mL of a 0.30M aqueous solution) was added. A white precipitate formed. After 2 h, methanol was removed on a rotary evaporator and the residue was partitioned between 10 mL water and 10 mL dichloromethane. The organic phase was separated, washed with water and brine and dried over anhydrous MgSO₄ and concentrated to give the title compound (16 mg) as a white solid.

Example 16

Synthesis of N-(4-cyanocyclopropyl)-3-(4-fluorophenylmethanesulfonyl)-2(R)-(2,2,2-trifluoro-1(S)-3-phenoxyphenylethylamino)propionamide

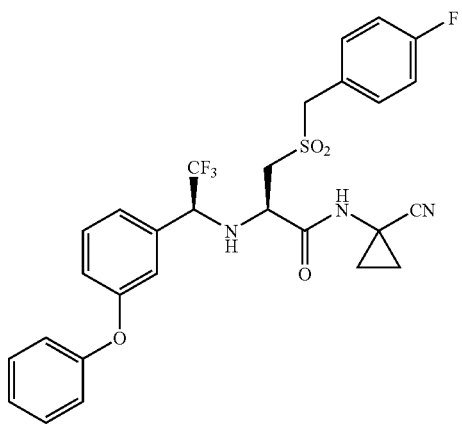

Step 1

3-Phenoxybromobenzene (552 mg, purchased from Apollo Scientific) was weighed into an oven-dried 20 mL vial fitted with a stir bar, septum, and nitrogen inlet and anhydrous THF (8 mL) was added and stirred to obtain a clear colorless solution. The reaction mixture was cooled to −78° and n-butyllithium in hexanes (0.84 mL of a 2.5M solution) was added dropwise. After 30 min, [2-(tert-butyldimethylsilanyloxy)-1(R)-(4-fluorobenzylsulfanylmethyl)ethyl]-(2,2,2-trifluoromethylethylidine (2.75 mL of a 0.366M solution in anhydrous THF) was added dropwise over 15 min. After 2 h, the reaction mixture was poured into a vigorously stirred mixture of 50 mL water, 50 mL crushed ice, 5 mL saturated aqueous NH₄Cl, and 25 mL EtOAc. The organic layre was separated and washed with brine and dried over MgSO₄. After concentration the residue was dissolved in 10 mL anhydrous THF and stirred in an ice/water bath. A 1.0M solution of tetrabutylammonium fluoride (1.10 mL) in THF was added dropwise over 15 min. After 2 h of stirring in an ice bath, the reaction mixture was poured into a vigorously stirred mixture of 50 mL water, 50 mL crushed ice, 5 mL saturated aqueous ammonium chloride and 50 mL EtOAc and allowed to stand overnight. The organic layer was separated and washed with brine and dried over MgSO₄. After concentrated the residue was purified by flash chromatography on 70 cm³ silica gel using 5% Et₂O/CH₂Cl₂ eluent to obtain 3-(4-fluorobenzylsulfanyl)-2(R)-[2,2,2-trifluoro-1(S)-(3-phenoxyphenyl)ethylamino]propan-1-ol (237 mg) as a clear colorless resin which was converted to the title compound by following the procedure described in Example 14, Steps 6 and 7 above.

Example 17

Synthesis of N-(4-cyanocyclopropyl)-3-(2-chlorophenyl)-2(S)-(2,2,2-trifluoro-1(RS)-3-phenylethylamino)propionamide

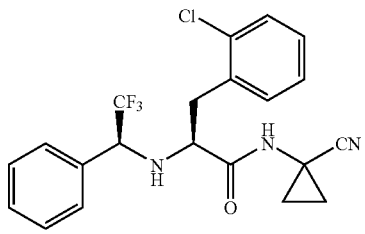

Step 1

2(S)-Amino-3-(2-chlorophenyl)propionic acid (1 g, commercially available) was dissolved in methanol (10 mL) and HCl gas was bubbled through the solution for 5 min. The reaction mixture was stirred at room temperature for 3 h and the solvent was evaporated using the rotavap to get 2(S)-amino-3-(2-chlorophenyl)propionic acid methyl ester hydrochloride (1.2 g).

Step 2

2,2,2-Trifluorol-phenylethanone (305 mg, 1.75 mmol) and 2(S)-amino-3-(2-chlorophenyl)-propionic acid methyl ester hydrochloride (500 mg, 1.75 mmol) were dissolved in DCM (10 mL). N,N-Diisopropylethylamine (1.2 mL, 7 mmol) was added followed by the addition 1M solution of TiCl₄ in DCM (1.75 mL, 1.75 mmol) and the reaction mixture was stirred for 18 h at room temperature. TiCl₄ (0.9 mL, 0.9 mmol) was added again and the solution was stirred at room temperature for 3 h. NaCNBH₃ (330 mg, 5.25 mmol) in MeOH (5 mL) was added and after stirring for 2 h, 1N NaOH solution (5 mL) was added. After 30 min, the suspension was filtered through celeite and the filtrate was extraced with ethylacetate. The organic layer was washed with brine and dried over MgSO₄. The solvent was evaporated to get methyl 3-(2-chlorophenyl)-2(S)-(2,2,2-trifluoro-1(RS)-phenylethylamino)propionate (600 mg) as a yellow solid which was used as such for the next step.

Step 3

Methyl 3-(2-chlorophenyl)-2(S)-(2,2,2-trifluoro-1(RS)-phenylethylamino)-propionate was dissolved in a mixture of MeOH (2 mL) and THF (5 mL) and 1N NaOH (4 mL) was added and the reaction mixture was stirred at room temperature for 4 h. The solvent was evaporated using a rotavap and the pH was adjusted to 6 using 1N HCl. The precipitated yellow solid was filtered and dried to give 3-(2-chlorophenyl)-2(S)-(2,2,2-trifluoro-1(RS)-phenylethylamino)propionic acid (500 mg).

Step 4

3-(2-chlorophenyl)-2(S)-(2,2,2-trifluoro-1(RS)-phenylethylamino)propionic acid (100 mg, 0.3 mmol) was dissolved in DMF (1 mL) and HATU (133 mg, 0.35 mmol), NMM (96 µl, 0.87 mmol) and 1-aminocyclopropylcarbonitrile (41.3 mg, 0.35 mmol) were added and the solution was stirred at room temperature for 4 h. The solution was diluted with ethylacetate (10 mL) and was washed with water, saturated solution of sodium bicarbonate, and brine. The organic layer was dried over $MgSO_4$ and the solvent was evaporated and the crude was purified by HPLC to give title compound (40 mg) as sticky solid. LCMS: $420.2(M-1)^{-1}$, $422.2(M+1)^{+1}$.

Proceeding as described in Example 17 above, but substituting 2,2,2-trifluoro1-phenyl-ethanone with 2,2,2-trifluoro 1-(4-fluorophenyl)ethanone provided N-(4-cyanocyclopropyl)-3-(2-chlorophenyl)-2(S)-[2,2,2-trifluoro-1(RS)-3-(4-fluorophenyl)ethylamino]propionamide LCMS: $438.3(M-1)^{-1}$, $440.2(M+1)^{+1}$.

Example 18

N-(1-cyanocyclopropyl)-3-cyclopropylmethanesulfonyl-2(R)-(2,2,2-trifluoro-1(S)-4-fluorophenylethylamino)propionamide

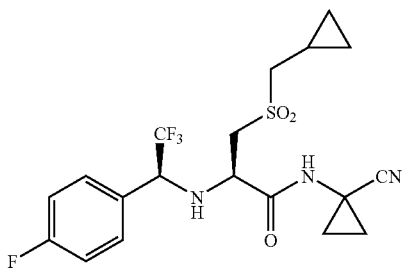

Step 1

To a slurry of S-trityl-L-cysteine (4.86 g, 13.37 mmol) in dichloromethane (97 mL, 20 mL/g AA) at room temperature was added diisopropylethylamine (9.32 mL, 53.48 mmol) followed by a solution of trifluoromethanesulfonic acid 2,2,2-trifluoro-1(RS)-phenylethyl ester (5.32 g, 16.04 mmol) (major enantiomer (S), 90 ee) in dichloromethane (15 mL) via syringe all at once. After 19 h, the reaction mixture was concentrated on the rotovap to give an oil. Diethyl ether was added and the solution was washed with 1N HCl and brine. The organic layer was dried over $MgSO_4$, filtered, and concentrated. Flash chromatography of the residue with 2 hexanes/1 ethyl acetate/0.25% acetic acid as the eluent provided 2(R)-[2,2,2-trifluoro-1(RS)-(4-fluorophenyl)ethylamino]-3-tritylsulfanyl-propionic acid (6 g) (major diastereomer (R,S), 90 de) as an oil/foam.

Step 2

Into a stirred solution of 2(R)-[2,2,2-trifluoro-1(RS)-(4-fluorophenyl)ethylamino]-3-tritylsulfanylpropionic acid (1.93 g, 3.58 mmol) in dichloromethane (5 mL) was added trifluoroacetic acid (489 mg, 4.29 mmol) and triethylsilane (498.9 mg, 4.29 mmol) at room temperature. After 16 h, the reaction was completed and the solvent was removed under vacuum. The residue was dissolved in 1N NaOH solution (15 mL) and extracted with hexane to remove the by products. To the aqueous solution, was added cyclopropylmethane bromide (482.9 mL, 3.58 mmol) in dioxane (15 mL) at room temperature. After 16 h, the organic solvent was removed under vacuum and the aqueous layer was acidified with 1N HCl, then extracted with ethyl ether (150 mL). The organic layer was washed with brine, dried with $MgSO_4$, and concentrated to give 2(R)-[2,2,2-trifluoro-1(RS)-(4-fluorophenyl) ethylamino]-3-cyclopropylmethanesulfanylpropionic acid (1.32 g).

Step 3

To a solution of 2(R)-[2,2,2-trifluoro-1(RS)-(4-fluorophenyl)ethylamino]-3-cyclopropyl-methanesulfanylpropionic acid (1.32 g) in DMF (10 mL) was added 1-aminocyclopropane-carbonitrile HCl salt (428.4 mg, 3.6 mg), HATU (1.64 g, 4.32 mmol), and DIPEA (1.39 g, 10.8 mmol) at room temperature. After 2 h, the reaction mixture was diluted with ethyl ether (150 mL) and washed with saturated $NaHCO_3$ and brine, dried over $MgSO_4$, and concentrated to provide N-(1-cyanocyclopropyl)-3-cyclopropyl-methanesulfanyl-2(R)-(2,2,2-trifluoro-1(RS)-4-fluorophenyl-ethylamino)propionamide (1.03 g). LC-MS: $414.1(M-1)$, $416.2(M+1)$, $438.1(M+Na)$.

Step 4

To a solution of N-(1-cyanocyclopropyl)-3-cyclopropyl-methanesulfanyl-2(R)-(2,2,2-trifluoro-1(RS)-4-fluorophenylethylamino)propionamide (1.03 g) in MeOH (10 mL) was added a solution of OXONE® (2.29 g, 3.72 mmol) in water (10 mL) at room temperature. After 2 h, the organics were removed under vacumn and the product was extracted into ethyl acetate (150 mL). The combined organic extracts were washed with brine, dried over $MgSO_4$, and concentrated to yield a white solid product (1.1 g). The solid was crystallized from a hot mixture of ethyl acetate (10 mL) and hexane (10 mL), to yield the title compound (622 mg) as a white crystalline product.

H-NMR($CDCl_3$): δ 8.56(1H, s, NH), 8.35-8.25(2H, m), 8.1-8(2H, m), 5.26(1H, ab), 4.65-4.55(1H, m), 4.46(1H, ab), 4.25(1H, ab), 4(2H, d), 2.48-2.4(3H, m), 2.12-2(3H, m), 1.7-1.6(2H, m), 1.4-1.3(2H, m). LC-MS: $446(M-1)$, $448(M+1)$, $470.3(M+Na)$.

BIOLOGICAL EXAMPLES

Example 1

Cathepsin B Assay

Solutions of test compounds in varying concentrations were prepared in 10 µl of dimethyl sulfoxide (DMSO) and then diluted into assay buffer (40 µL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 µL of assay buffer) was added to the dilutions. The assay solutions were mixed for 5-10 seconds on a shaker plate, covered and incubated for 30 min at room temperature. Z-FR-AMC (20 nMoles in 25 µL of assay buffer) was added to the assay solutions and hydrolysis was followed spectrophotometrically at (λ460 mn) for 5 min. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5-10 seconds on a shaker plate, covered and incubated for 30 min at room temperature. Z-Phe-Arg-AMC (4 nMoles in 25 μL of assay buffer) was added to the assay solutions and hydrolysis was followed spectrophotometrically at ($\lambda$460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5-10 seconds on a shaker plate, covered and incubated for 30 min at room temperature. Z-Phe-Arg-AMC (1 nMoles in 25 μL of assay buffer) was added to the assay solutions and hydrolysis was followed spectrophotometrically at ($\lambda$460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 μL of assay buffer) was added to the dilutions. The assay solutions were mixed for 5-10 seconds on a shaker plate, covered and incubated for 30 min at room temperature. Z-Val-Val-Arg-AMC (4 nMoles in 25 μL of assay buffer containing 10% DMSO) was added to the assay solutions and hydrolysis was followed spectrophotometrically (at $\lambda$460 nm) for 5 min. Apparent inhibition constants ($K_i$) were calculated from the enzyme progress curves using standard mathematical models.

Compounds of the invention were tested by the above-described assay and observed to exhibit cathepsin S inhibitory activity.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5-10 seconds on a shaker plate, covered and incubated for 30 min at room temperature. Z-Phe-Arg-AMC (2 nMoles in 25 μL of assay buffer containing 10% DMSO) was added to the assay solutions and hydrolysis was followed spectrophotometrically (at $\lambda$460 nm) for 5 min. Apparent inhibition constants ($K_i$) were calculated from the enzyme progress curves using standard mathematical models.

Compounds of the invention were tested by the above-described assay and observed to exhibit cathepsin F inhibitory activity.

Example 1

Representative pharmaceutical formulations Containing a Compound of Formula (I)

| ORAL FORMULATION | |
| --- | --- |
| Compound of Formula (I) | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
| --- | --- |
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
| --- | --- |
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:
1. A compound of Formula (I):

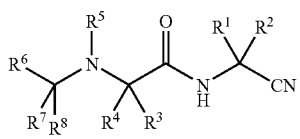

R$^1$ and R$^2$ taken together with the carbon atom to which both R$^1$ and R$^2$ are attached form (i) cycloalkylene optionally substituted with one or two R$^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl or (ii) heterocyclylalkylene optionally substituted with one to four R$^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R$^{14}$, -alkylene-S(O)$_{n2}$—R$^{15}$, —COOR$^{16}$, -alkylene-COOR$^{17}$, —CONR$^{18}$R$^{19}$, or -alkylene-CONR$^{20}$R$^{21}$ (where n2 is 0-2 and R$^{14}$-R$^{17}$, R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

R$^3$ is hydrogen or alkyl;

R$^4$ is aryl, aralkyl, heteroaryl, heteroaralkyl, heterocyclylalkyl, or -alkylene-X$^1$—R$^{22}$ (wherein X$^1$ is —NR$^{23}$—, —O—, —S(O)$_{n3}$—, —CO—, —COO—, —OCO—, —NR$^{23}$CO—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$, or —NR$^{23}$SO$_2$NR$^{24}$— where R$^{23}$ and R$^{24}$ are independently hydrogen, alkyl, or acyl, n3 is 0-2, and R$^{22}$ is hydrogen, alkyl, haloalkyl, cycloalkyl, cycloalkylalkyl, aryl, aralkyl, heteroaryl, heteroaralkyl, heterocyclyl, or heterocyclylalkyl) wherein said alkylene chain in R$^4$ is optionally substituted with one to six halo and wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

R$^5$ is hydrogen or alkyl;

R$^6$ is hydrogen, alkyl, haloalkyl, cycloalkyl, aryl, aralkyl, heteroaryl, heteroaralkyl, heterocyclyl, or -alkylene-X$^2$—R$^{25}$ (wherein X$^2$ is —NR$^{26}$—, —O—, —S(O)$_{n4}$—, —CO—, —COO—, —OCO—, —NR$^{26}$CO—, —CONR$^{26}$—, —NR$^{26}$SO$_2$—, —SO$_2$NR$^{26}$—, —NR$^{26}$COO—, —OCONR$^{26}$—, —NR$^{26}$CONR$^{27}$—, or —NR$^{26}$SO$_2$NR$^{27}$— where R$^{26}$ and R$^{27}$ are independently hydrogen, alkyl, or acyl, n4 is 0-2, and R$^{25}$ is hydrogen, alkyl, haloalkyl, cycloalkyl, cycloalkylalkyl, heterocyclyl, heterocyclylalkyl, aryl, aralkyl, heteroaryl, or heteroaralkyl) wherein said alkylene chain in R$^6$ is optionally substituted with one to six halo and the aromatic or alicyclic rings in R$^6$ are optionally substituted by one, two, or three R$^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl and further where the aromatic or alicyclic rings in R$^e$ is optionally substituted by one, two or three R$^f$ independently selected from alkyl, alkoxy, haloalkyl, haloalkoxy, halo, hydroxy, carboxy, cyano, nitro, aryl or cycloalkyl;

R$^7$ is haloalkyl; and

R$^8$ is hydrogen, alkyl, alkoxyalkyl or haloalkyl; or

R$^6$ and R$^8$ together with the carbon atom to which they are attached form cycloalkylene or heterocyclylalkylene wherein said cycloalkylene is optionally substituted with one or two substituents independently selected from alkyl, haloalkyl, hydroxy, or alkoxy and heterocyclylalkylene is optionally substituted with one or two substituents independently selected from alkyl, haloalkyl, hydroxy, or alkoxy; or a pharmaceutically acceptable salt thereof.

2. The compound of claim 1 wherein R$^1$ and R$^2$ together with the carbon atom to which they are attached form cycloalkylene optionally substituted with one or two R$^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl.

3. The compound of claim 1 where R$^1$ and R$^2$ together with the carbon atom to which they are attached form cyclopropylene, cyclopentylene, or cyclohexylene.

4. The compound of claim 1 wherein R$^1$ and R$^2$ together with the carbon atom to which they are attached form pyrrolidinyl, piperidin-4-yl substituted at the 1-position with methyl, ethyl, propyl, n-butyl, or 2,2,2-trifluoroethyl, tetrahydropyranyl, tetrahydrothiopyranyl, tetrahydrothiopyran-4-yl-1-oxide, or tetrahydrothiopyran-4-yl-1,1-dioxide.

5. The compound of claim 1 wherein:

R$^1$ and R$^2$ together with the carbon atom to which they are attached form cyclopropylene and R$^4$ is aralkyl, heteroaralkyl, heterocyclylalkyl, or -alkylene-X$^1$—R$^{22}$ (wherein X$^1$ is —NR$^{23}$—, —O—, —S(O)$_{n3}$—, —CO—, —COO—, —OCO—, —NR$^{23}$CO—, —CONR$^{23}$—, —NR$^{23}$SO$_2$—, —SO$_2$NR$^{23}$—, —NR$^{23}$COO—, —OCONR$^{23}$—, —NR$^{23}$CONR$^{24}$, or —NR$^{23}$SO$_2$NR$^{24}$— where R$^{23}$ and R$^{24}$ are independently hydrogen, alkyl, or acyl, n3 is 0-2, and R$^{22}$ is hydrogen, alkyl, haloalkyl, cycloalkyl, cycloalkylalkyl, aryl, aralkyl, heteroaryl, heteroaralkyl, heterocyclyl, or heterocyclylalkyl) wherein said alkylene chain in R$^4$ is optionally substituted with one to six halo and further wherein the aromatic or alicyclic ring in R$^4$ is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; and R$^3$ and R$^5$ are hydrogen.

6. The compound of claim 2 wherein:

R$^1$ and R$^2$ together with the carbon atom to which they are attached form cyclopropylene;

R$^4$ is ethylthiomethyl, ethylsulfinylmethyl, ethylsulfonylmethyl, isopropylthiomethyl, 2-methylthioethyl, 2-methylsulfinylethyl, 2-methysulfonylethyl, 2-methylpropylsulfonylmethyl, isobutylsulfanylmethyl, tert-butylthiomethyl, benzenesulfonylmethyl, 2-phenylsulfanylethyl, 2-phenylsulfonylethyl, naphth-2-ylmethanesulfonylmethyl, biphenyl-2-ylmethane-sulfonylmethyl, biphenyl-4-ylmethanesulfonylmethyl, phenylmethanesulfanylmethyl, phenylmethanesulfinyl-methyl, phenylmethanesulfonylmethyl, 2-phenyl-methanesulfonylethyl, 4-tert-butylphenylmethane-sulfonyl-methyl, 2-fluorophenylmethanesulfanylmethyl, 2-fluorophenyl-methanesulfonylmethyl, 3-fluorophenylmethanesulfo-nylmethyl, 4-fluorophenylmethanesulfonylmethyl, 2-chlorophenyl-methanesulfanylmethyl, 2-chlorophe-nylmethanesulfonylmethyl, 3-chlorophenylmethane-sulfonyl-methyl, 4-chlorophenylmethanesulfonyl-methyl, 2-methoxyphenylmethanesulfonylmethyl, 4-methoxyphenylmethanesulfonylmethyl, 2-trifluo-romethoxyphenylmethanesulfonylmethyl, 3-trifluo-romethoxyphenylmethane-sulfonylmethyl, 4-trifluo-romethoxyphenylmethane-sulfonylmethyl, 2-trifluoromethylphenylmethanesulfanylmethyl, 2-trif-luoromethylphenylmethane-sulfonylmethyl, 3-trifluo-romethylphenylmethane-sulfonylmethyl, 4-trifluorom-ethylphenylmethane-sulfonylmethyl, 2-cyanophenylmethane-sulfanylmethyl, 2-cyanophe-nylmethanesulfonylmethyl, 3-cyanophenylmethane-sulfonylmethyl, 2-bromophenylmethanesulfonylm-ethyl, 2-nitrophenyl-methanesulfanylmethyl, 2-nitrophenyl-methanesulfonylmethyl, 2-methylphe-nylmethane-sulfonylmethyl, 3-methylphenylmethane-sulfonylmethyl, 4-methylphenylmethanesulfonyl-methyl, 2-(4-trifluoromethoxy-benzenesulfonyl)ethyl, 2-(3-trifluoromethoxybenzenesulfonyl)-ethyl, 2-(2-trif-luoromethoxy-benzenesulfonyl)ethyl, 2-difluo-romethoxyphenylmethanesulfonylmethyl, 3-difluo-romethoxyphenylmethane-sulfonylmethyl, 4-difluoromethoxyphenylmethane-sulfonylmethyl, 2-(4-difluoromethoxybenzenesulfonyl)ethyl, 2-(2-dif-luoromethoxybenzene-sulfonyl)ethyl, 2-(3-difluo-romethoxybenzenesulfonyl)ethyl, 3-chloro-2-fluo-rophenylmethane-sulfonylmethyl, 3,5-dimethylphenylmethanesulfonylmethyl, 3,5-bis-trifluoromethylphenyl-methanesulfonylmethyl, 2,5-difluorophenyl-methanesulfonylmethyl, 2,6-difluorophenyl-methanesulfonylmethyl, 2,3-difluorophenyl-methanesulfonylmethyl, 3,4-difluorophenyl-methanesulfonylmethyl, 2,4-difluorophenyl-methanesulfonylmethyl, 2,5-dichloro-phenylmethane-sulfonylmethyl, 3,4-dichlorophenylmethanesulfonylmethyl, 2,6-dichlorophenylmethane-sulfonylmethyl, 2-fluoro-3-methylphenylmethanesulfonylmethyl, 4-fluoro-2-trifluoromethoxy-phenylmethanesulfonylmethyl, 2-fluoro-6-trifluoromethylphenyl-methanesulfonylm-ethyl, 2-fluoro-3-trifluoromethylphenyl-methanesulfo-nylmethyl, 2-fluoro-4-trifluoromethylphenyl-methane-sulfonylmethyl, 2-fluoro-5-trifluoromethyl-phenylmethanesulfonylmethyl, 4-fluoro-3-trifluoromethyl-phenylmethanesulfonylmethyl, 2-chloro-5-trifluoromethylphenyl-methanesulfonylm-ethyl, 2,4,6-trifluorophenylmethane-sulfonylmethyl, 2,4,5-trifluorophenylmethanesulfonylmethyl, 2,3,4-tri-fluorophenylmethane-sulfonylmethyl, 2,3,5-trifluo-rophenylmethanesulfonylmethyl, 2,5,6-trifluorophe-nylmethane-sulfonyl-methyl, 3,4,5-trimethoxyphenylmethanesulfonylmethyl, pyridin-2-ylmethanesulfonyl-methyl, pyridin-3-ylmethanesulfonylmethyl, pyridin-4-ylmethanesulfonylmethyl, 2-(pyridin-2-ylsulfonyl) ethyl, 2-(pyridin-4-ylsulfonyl)ethyl, oxypyridin-2-ylmethane-sulfonylmethyl, cyclohexylmethanesulfanylmethyl, cyclohexyl-methanesulfinylmethyl, cyclohexylmethane-sulfonylm-ethyl, 2-cyclohexylethanesulfonylmethyl, cyclohexyl-methanesulfonylmethyl, thiophene-2-sulfonylmethyl, 5-chlorothien-2-ylmethane-sulfonylmethyl, or 3,5-dim-ethyl-isoxazol-4-ylmethanesulfonylmethyl; and $R^3$ and $R^5$ are hydrogen.

7. The compound of claim 6
wherein:
$R^6$ is alkyl, haloalkyl, cycloalkyl, phenyl, benzyl, naphthyl, alkylSO$_2$alkyl, cycloalkylSO$_2$alkyl, arylSO$_2$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein the aromatic or alicyclic ring in $R^6$ is optionally substituted by one, two, or three $R^e$;
each $R^e$ is independently alkyl, halo, hydroxy, oxo, carboxy, cyano, nitro, cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, alkoxy, —COR (where R is alkyl), alkoxycarbonyl, aryloxycarbonyl where the aromatic or alicyclic rings in $R^e$ may be further optionally substituted by one, two or three $R^f$ independently selected from alkyl, alkoxy, haloalkyl, haloalkoxy, halo, hydroxy, carboxy, cyano, nitro, aryl or cycloalkyl.

8. The compound of claim 7 wherein:
$R^6$ is methyl, ethyl, isopropyl, trifluoromethyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, or pyrazinyl wherein the aromatic or alicyclic rings in $R^6$ are optionally substituted with one, two, or three $R^e$ independently selected from methyl ethyl, fluoro, chloro, bromo, iodo, hydroxy, oxo, carboxy, cyano, nitro, cyclopropyl, phenyl, pyrrolidinyl, piperidinyl, morpholinyl, thiomorpholinyl, piperazinyl, thienyl, imidazolyl, methoxy, acetyl, or methoxycarbonyl wherein the aromatic or alicyclic rings in $R^e$ are further optionally substituted with one, two, or three $R^f$ independently selected from methyl, cyclopropyl, phenyl, methoxy, fluoro, chloro, hydroxy, or carboxy.

9. The compound of claim 7 wherein:
$R^6$ is phenyl, 4-methoxyphenyl, 4-chlorophenyl, 2-fluorophenyl 4-fluorophenyl, 2-fluoro-4-chlorophenyl, naphthyl, piperidin-4-yl, furanyl, thienyl, pyridin-4-yl, or pyrazinyl and $R^8$ is hydrogen or haloalkyl.

10. The compound of claim 9 wherein $R^7$ is trifluoromethyl and $R^8$ is hydrogen.

11. The compound of claim 1 wherein:
$R^6$ and $R^8$ together with the carbon to which they are attached form cycloalkylene.

12. The compound of claim 1 wherein:
$R^6$ and $R^8$ together with the carbon to which they are attached form heterocyclylalkylene.

13. A compound of Formula (I):

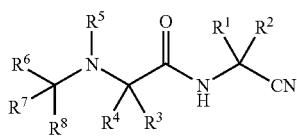

wherein:
R¹ and R² taken together with the carbon atom to which both R¹ and R² are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl, (ii) a four atom heterocyclylalkylene ring, or (iii) heterocyclylalkylene optionally substituted with one to four $R^c$ independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R¹⁴, -alkylene-S(O)$_{n2}$—R¹⁵, —COOR¹⁶, -alkylene-COOR¹⁷, —CONR¹⁸R¹⁹, or -alkylene-CONR²⁰R²¹ (where n2 is 0-2 and R¹⁴-R¹⁷, R¹⁸ and R²⁰ are independently hydrogen, alkyl, haloalkyl, aryl, aralkyl, heteroaryl, heteroaralkyl, cycloalkyl, cycloalkylalkyl, or heterocyclyl and R¹⁹ and R²¹ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, cycloalkyl, cycloalkylalkyl, aralkyl, aryloxycarbonyl, alkoxy, hydroxy, haloalkoxy, halo, carboxy, alkoxycarbonyl, amino, monsubstituted amino, disubstituted amino, or acyl;

R³ is hydrogen or alkyl;

R⁴ is -alkylene-S(O)₂—R²² where R²² is aralkyl, heteroaryalkyl, or cycloalkylalkyl wherein the alkylene chain in R⁴ is optionally substituted with one to six halo and further wherein the aromatic or alicyclic ring in R⁴ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

R⁵ is hydrogen or alkyl;

R⁶ is hydrogen, alkyl, haloalkyl, cycloalkyl, aryl, aralkyl, heteroaryl, heteroaralkyl, heterocyclyl, or -alkylene-X²—R²⁵ (where X² is —NR²⁶—, —O—, —S(O)$_{n4}$—, —CO—, —COO—, —OCO—, —NR²⁶CO—, —CONR²⁶—, —NR²⁶SO₂—, —SO₂NR²⁶—, —NR²⁶COO—, —OCONR²⁶—, —NR²⁶CONR²⁷—, or —NR²⁶SO₂NR²⁷— where R²⁶ and R²⁷ are independently hydrogen, alkyl, or acyl, n4 is 0-2, and R²⁵ is hydrogen, alkyl, haloalkyl, cycloalkyl, cycloalkylalkyl, heterocyclyl, heterocyclylalkyl, aryl, aralkyl, heteroaryl, or heteroaralkyl) wherein said alkylene chain in R⁶ is optionally substituted with one to six halo and the aromatic or alicyclic rings in R⁶ are optionally substituted by one, two, or three $R^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, aryl, aralkyl, aryloxy, aralkyloxy, arylsulfonyl, heteroaryl, heteroaralkyl, heteroaryloxy, heteroaralkyloxy, heteroarylsulfonyl, heterocyclyl, heterocyclylalkyl, cycloalkyl, cycloalkylalkyl, carboxy, alkoxycarbonyl, alkylsulfonyl, aminosulfonyl, or aminoalkyl and further where the aromatic or alicyclic rings in $R^e$ is optionally substituted with one, two or three $R^f$ independently selected from alkyl, alkoxy, haloalkyl, haloalkoxy, halo, hydroxy, carboxy, cyano, nitro, aryl or cycloalkyl;

R⁷ is haloalkyl optionally substituted with alkoxy or alkoxyalkyloxy; and R⁸ is hydrogen, alkyl, alkoxyalkyl or haloalkyl; or R⁶ and R⁸ together with the carbon atom to which they are attached form cycloalkylene or heterocyclylalkylene wherein said cycloalkylene is optionally substituted with one to four substituents independently selected from alkyl, halo, haloalkyl, hydroxy, or alkoxy and heterocyclylalkylene is optionally substituted with one or two substituents independently selected from alkyl, halo, haloalkyl, cycloalkyl, hydroxy, or alkoxy; or a pharmaceutically acceptable salts thereof.

14. The compound of claim 13 wherein:
R¹ and R² are hydrogen or R¹ and R² together with the carbon atom to which they are attached form cyclopropylene;
R³ is hydrogen;
R⁴ is —CH₂—S(O)₂—R²² where R²² is aralkyl, heteroaryalkyl, or cycloalkylalkyl wherein the the aromatic or alicyclic ring in R⁴ is optionally substituted with one, two, or three $R^d$ independently selected from alkyl, haloalkyl, alkoxy, hydroxy, haloalkoxy, halo, nitro, cyano, carboxy, alkoxycarbonyl, amino, monsubstituted amino, disubstituted amino, or acyl;
R⁵ is hydrogen;
R⁶ is aryl or heteroaryl wherein the aromatic or alicyclic rings in R⁶ are optionally substituted by one, two, or three $R^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, carboxy, alkoxycarbonyl, arylsulfonyl, alkylsulfonyl, aminosulfonyl, or aminoalkyl;
R⁷ is haloalkyl; and
R⁸ is hydrogen.

15. The compound of claim 14 wherein:
R¹ and R² together with the carbon atom to which they are attached form cyclopropylene;
R⁴ is phenylmethanesulfonylmethyl, 4-tert-butylphenylmethanesulfonylmethyl, 2-fluorophenylmethanesulfonylmethyl, 3-fluorophenylmethanesulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethane-sulfonylmethyl, 4-trifluoromethoxyphenylmethane-sulfonylmethyl, 2-trifluoromethylphenylmethanesulfonylmethyl, 3-trifluoromethylphenylmethanesulfonyl-methyl, 4-trifluoromethylphenylmethanesulfonylmethyl, 2-cyanophenylmethanesulfonyl-methyl, 3-cyanophenylmethanesulfonylmethyl, 2-bromophenylmethanesulfonylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-difluoromethoxyphenylmethanesulfonylmethyl, 3-difluoromethoxyphenylmethane-sulfonylmethyl, 4-difluoromethoxyphenylmethane-sulfonylmethyl, 3-chloro-2-fluorophenyl-methane-sulfonylmethyl, 3,5-dimethylphenylmethanesulfonylmethyl, 3,5-bis-trifluoromethylphenyl-methanesulfonylmethyl, 2,5-difluorophenylmethane-sulfonylmethyl, 2,6-difluorophenylmethanesulfonylmethyl, 2,3-difluorophenylmethane-sulfonylmethyl, 3,4-difluorophenylmethanesulfonylmethyl, 2,4-difluorophenylmethane-sulfonylmethyl, 2,5-dichlorophenylmethanesulfonylmethyl, 3,4-dichlorophenylmethane-sulfonylmethyl, 2,6-dichlorophenylmethanesulfonylmethyl, 2-fluoro-3-methylphenylmethane-sulfonyl-methyl, 4-fluoro-2-trifluoromethoxyphenylmethane-sulfonylmethyl, 2-fluoro-6-trifluoromethylphenylmethane-sulfonylmethyl, 2-fluoro-3-trifluoromethylphenyl-methanesulfonylmethyl, 2-fluoro-4-trifluoromethylphenylmethanesulfonylmethyl, 2-fluoro-5-trifluoromethyl-phenylmethanesulfonylmethyl, 4-fluoro-3-trifluoromethyl-phenylmethanesulfonylmethyl, 2-chloro-5-trifluoromethylphenylmethane-sulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 3,4,5-trimethoxyphenylmethanesulfonylmethyl, pyridin-2-ylmethanesulfonylmethyl, pyridin-3-ylmethanesulfonylmethyl, pyridin-4-ylmethanesulfonylmethyl, N-oxypyridin-2-ylmethanesulfonylmethyl, 2-trifluoropyridin-6-ylmethanesulfonylmethyl, pyrazin-2-ylmethanesulfonylmethyl, cyclohexylmethanesulfonylmethyl, cyclopropylmethanesulfonylmethyl, thiophene-2-sulfonylmethyl, 5-chloro-thien-2-yl-methanesulfonylmethyl, or 3,5-dimethylisoxazol-4-yl-methanesulfonylmethyl.

16. The compound of claim 14 wherein:
$R^1$ and $R^2$ together with the carbon atom to which they are attached form cyclopropylene;
$R^4$ phenylmethanesulfonylmethyl, 4-fluorophenyl-methanesulfonylmethyl, cyclopropylmethanesulfonylmethyl, pyridin-2-ylmethanesulfonylmethyl, 2-trifluoromethyl-pyridin-6-ylmethanesulfonylmethyl, 2-difluoromethoxyphenylmethanesulfonylmethyl, or pyrazin-2-ylmethanesulfonylmethyl; and
$R^6$ is furan-2-yl, indol-3-yl, thiophen-2-yl, 1-methylpyrrol-2-yl, 1-phenylsulfonylpyrrol-2-yl, pyridin-2-yl, or phenyl optionally substituted with one, two, or three $R^e$ independently selected from alkyl, hydroxyl, or halo.

17. The compound of claim 16 wherein:
$R^6$ is furan-2-yl, indol-3-yl, thiophen-2-yl, 1-methylpyrrol-2-yl, 1-phenylsulfonyl-pyrrol-2-yl, pyridin-2-yl, phenyl, 2-hydroxyphenyl, 4-hydroxyphenyl, 3-chloro-4-hydroxyphenyl, 3-bromophenyl, 4-fluorophenyl, 3,4-difluorophenyl, or 3,4,5-trifluorophenyl; and
$R^7$ is trifluoromethyl or difluoromethyl.

18. A compound selected from the group consisting of:
N-(1-cyanocyclopropyl)-3-phenylmethanesulfonyl-2(R)-(2,2,2-trifluoro-1(S)-phenylethylamino)-propionamide;
N-(4-cyano-1-ethylpiperidin-4-yl)-3-(phenylmethanesulfonyl-2(R)-(2,2,2-trifluoro-1(S)-phenyl-ethylamino)propionamide;
N-(4-cyano-1,1-dioxohexahydro-1$\lambda^6$-thiopyran-4-yl)-3-phenylmethanesulfonyl-2(R)-(2,2,2-trifluoro-1(S)-phenylethylamino)-propionamide;
N-(1-cyanocyclopropyl)-3-phenylmethanesulfanyl-2(R)-(2,2,2-trifluoro-1(S)-4-hydroxyphenyl-ethylamino)propionamide;
N-(1-cyanocyclopropyl)-3-cyclopropylmethanesulfonyl-2(R)-(2,2,2-trifluoro-1(S)-phenylethyl-amino)propionamide;
N-(1-cyanocyclopropyl)-3-phenylmethanesulfanyl-2(R)-(2,2,2-trifluoro-1(RS)-furan-2-ylethyl-amino)propionamide;
N-(1-cyanocyclopropyl)-3-phenylmethanesulfonyl-2(R)-(2,2,2-trifluoro-1(RS)-furan-2-ylethyl-amino)propionamide;
N-(1-cyanocyclopropyl)-3-cyclopropylmethanesulfonyl-2(R)-(2,2,2-trifluoro-1(S)-3-bromophenyl-ethylamino)propionamide;
N-(1-cyanocyclopropyl)-3-phenylmethanesulfanyl-2(R)-(2,2,2-trifluoro-1(RS)-indol-3-ylethyl-amino)propionamide;
N-(1-cyanocyclopropyl)-3-phenylmethanesulfonyl-2(R)-(2,2,2-trifluoro-1(RS)-indol-3-ylethyl-amino)propionamide;
N-(1-cyanocyclopropyl)-3-phenylmethanesulfanyl-2(R)-(2,2,2-trifluoro-1(RS)-thiophen-2-ylethyl-amino)propionamide;
N-(1-cyanocyclopropyl)-3-phenylmethanesulfonyl-2(R)-(2,2,2-trifluoro-1(RS)-thiophen-2-ylethyl-amino)propionamide;
N-(1-cyanocyclopropyl)-3-cyclopropylmethanesulfonyl-2(R)-(2,2,2-trifluoro-1(S)-4-fluorophenyl-ethylamino)propionamide;
N-(1-cyanocyclopropyl)-3-phenylmethanesulfonyl-2(R)-(2,2,2-trifluoro-1(S)-methylethylamino)-propionamide;
N-(1-cyanocyclopropyl)-3-phenylmethanesulfonyl-2(R)-(2,2,2-trifluoro-1(S)-1-methylpyrrol-2-yl-ethylamino)propionamide;
N-(1-cyanocyclopropyl)-3-(1-methylcyclopentyl)-2(S)-(2,2,2-trifluoro-1(S)-thiophen-2-ylethyl-amino)propionamide;
N-(1-cyanocyclopropyl)-3-(1-methylcyclopentyl)-2(S)-(2,2,2-trifluoro-1(R)-thiophen-2-ylethyl-amino)propionamide;
N-(1-cyanocyclopropyl)-3-phenylmethanesulfonyl-2(R)-(2,2,2-trifluoro-1(S)-4-fluorophenylethyl-amino)propionamide;
N-(1-cyanocyclopropyl)-3-pyridin-2-ylmethanesulfanyl-2(R)-(2,2,2-trifluoro-1(RS)-phenylethylamino)propionamide;
N-(1-cyanocyclopropyl)-3-pyridin-2-ylmethanesulfonyl-2(R)-(2,2,2-trifluoro-1(S)-phenylethylamino)propionamide;
N-(1-cyanocyclopropyl)-3-(1-methylcyclopentyl)-2(S)-(2,2,2-trifluoro-1(S)-2-hydroxyphenyl-ethylamino)propionamide;
N-(1-cyanocyclopropyl)-3-(1-methylcyclopentyl)-2(S)-(2,2,2-trifluoro-1(R)-4-hydroxyphenyl-ethylamino)propionamide;
N-(1-cyanocyclopropyl)-3-pyridin-2-ylmethanesulfonyl-2(R)-(2,2,2-trifluoro-1(R)-phenylethyl-amino)propionamide;
N-(1-cyanocyclopropyl)-3-(1-methylcyclopentyl)-2(S)-(2,2,2-trifluoro-1(S)-4-hydroxyphenyl-ethylamino)propionamide;

N-(1-cyanocyclopropyl)-3-(2-chlorophenyl)-2(S)-(2,2,2-trifluoro-1(RS)-phenylethylamino)-propionamide;

N-(1-cyanocyclopropyl)-3-(2-chlorophenyl)-2(S)-(2,2,2-trifluoro-1(RS)-4-fluorophenyl-ethylamino)-propionamide;

N-(1-cyanocyclopropyl)-3-pyridin-2-ylmethanesulfonyl-2(R)-(2,2,2-trifluoro-1(RS)-4-fluorophenyl-ethylamino)propionamide;

N-(1-cyanocyclopropyl)-3-phenylmethanesulfonyl-2(R)-(2,2,2-trifluoro-1(S)-4-hydroxyphenyl-ethylamino)propionamide;

N-(1-cyanocyclopropyl)-3-phenylmethanesulfanyl-2(R)-(2,2,2-trifluoro-1(R)-3-chloro-4-hydroxy-phenylethylamino)propionamide;

N-(1-cyanocyclopropyl)-3-phenylmethanesulfanyl-2(R)-(2,2,2-trifluoro-1(S)-3-chloro-4-hydroxy-phenylethylamino)propionamide;

N-(1-cyanocyclopropyl)-3-phenylmethanesulfonyl-2(R)-(2,2,2-trifluoro-1(R)-3-chloro-4-hydroxy-phenylethylamino)propionamide;

N-(1-cyanocyclopropyl)-3-phenylmethanesulfonyl-2(R)-(2,2,2-trifluoro-1(S)-3-chloro-4-hydroxy-phenylethylamino)propionamide;

N-(1-cyanocyclopropyl)-3-(1-methylcyclopentyl)-2(S)-(2,2-difluoro-1(R)-thiophen-2-ylethyl-amino)propionamide;

N-(1-cyanocyclopropyl)-3-phenylmethanesulfanyl-2(R)-(2,2-difluoro-1(RS)-thiophen-2-ylethyl-amino)propionamide;

N-(1-cyanocyclopropyl)-3-(1-methylcyclopentyl)-2(S)-(2,2,2-trifluoro-1(S)-3-fluoro-4-hydroxy-phenylethylamino)propionamide;

N-(1-cyanocyclopropyl)-3-phenylmethanesulfanyl-2(R)-(2,2,2-trifluoro-1(RS)-pyridin-2-ylethyl-amino)propionamide;

N-(1-cyanocyclopropyl)-4-pyridin-2-ylsulfanyl-2(S)-(2,2,2-trifluoro-1(RS)-4-fluorophenyl-ethylamino)butyramide;

N-(1-cyanocyclopropyl)-4-pyridin-2-ylsulfonyl-2(S)-(2,2,2-trifluoro-1(RS)-4-fluorophenyl-ethylamino)butyramide;

N-(1-cyanocyclopropyl)-3-phenylmethanesulfonyl-2(R)-(2,2,2-trifluoro-1(RS)-pyridin-2-yl-ethylamino)propionamide;

N-(1-cyanocyclopropyl)-3-phenylmethanesulfonyl-2(R)-(2,2-difluoro-1(R)-thiophen-2-yl-ethylamino)propionamide;

N-(1-cyanocyclopropyl)-3-(2-difluoromethoxyphenyl-methanesulfanyl)-2(R)-(2,2,2-trifluoro-1(RS)-thiophen-2-ylethylamino)propionamide;

N-(1-cyanocyclopropyl)-3-(2-difluoromethoxyphenyl-methanesulfonyl)-2(R)-(2,2,2-trifluoro-1(RS)-thiophen-2-ylethylamino)propionamide;

N-(1-cyanocyclopropyl)-3-pyridin-2-ylmethanesulfanyl-2(R)-(2,2,2-trifluoro-1(S)-4-fluorophenyl-ethylamino)propionamide;

N-(1-cyanocyclopropyl)-3-pyridin-2-ylmethanesulfonyl-2(R)-(2,2,2-trifluoro-1(S)-4-fluorophenyl-ethylamino)propionamide;

N-(1-cyanocyclopropyl)-3-pyridin-2-ylmethanesulfanyl-2(R)-(2,2,2-trifluoro-1(R)-4-fluorophenyl-ethylamino)propionamide;

N-(1-cyanocyclopropyl)-3-pyridin-2-ylmethanesulfonyl-2(R)-(2,2,2-trifluoro-1(R)-4-fluorophenyl-ethylamino)propionamide;

N-(1-cyanocyclopropyl)-3-cyclopropylmethanesulfonyl-2(R)-(2,2,2-trifluoro-1(S)-thiophen-3-ylethylamino)propionamide;

N-(1-cyanocyclopropyl)-3-cyclopropylmethanesulfanyl-2(R)-(2,2,2-trifluoro-1(RS)-thiophen-2-yl-ethylamino)propionamide;

N-(1-cyanocyclopropyl)-3-cyclopropylmethanesulfonyl-2(R)-(2,2,2-trifluoro-1(RS)-thiophen-2-yl-ethylamino)propionamide;

N-(1-cyanotetrahydropyran-4-yl)-3-cyclopropylmethanesulfonyl-2(R)-(2,2,2-trifluoro-1(S)-4-fluorophenyl-ethylamino)propionamide;

N-(1-cyanocyclopropyl)-3-cyclopropylmethanesulfonyl-2(R)-(2,2,2-trifluoro-1(S)-3,4-difluoro-phenylethylamino)propionamide;

N-(1-cyanocyclopropyl)-3-cyclopropylmethanesulfonyl-2(R)-(2,2,2-trifluoro-1(S)-1-methylpyrrol-2-ylethylamino)propionamide;

N-(1-cyanocyclopropyl)-3-cyclopropylmethanesulfonyl-2(R)-(2,2,2-trifluoro-1(S)-1-oxo-1-methyl-pyrrol-2-yl-ethylamino)propionamide;

N-(1-cyanocyclopropyl)-3-cyclopropylmethanesulfonyl-2(R)-(2,2,2-trifluoro-1(S)-3,4,5-trifluoro-phenylethylamino)propionamide;

N-(1-cyanocyclopropyl)-3-(4-fluorophenylmethanesulfonyl)-2(R)-(2,2,2-trifluoro-1(S)-4-fluoro-phenylethylamino)propionamide;

N-(1-cyanotetrahydrothiopyran-4-yl)-3-(4-fluorophenyl-methanesulfonyl)-2(R)-(2,2,2-trifluoro-1(S)-4-fluorophenyl-ethylamino)propionamide;

N-(1cyanocyclopropyl)-3-(4-fluorophenylmethanesulfonyl)-2(R)-(2,2,2-trifluoro-1(S)-3-phenoxy-phenylethylamino)propionamide;

N-(1-cyano-1,1-dioxohexahydro-1$\lambda^6$-thiopyran-4-yl)-3-(4-fluorophenylmethane-sulfonyl)-2(R)-(2,2,2-trifluoro-1(S)-4-fluorophenylethylamino)propionamide;

N-(1-cyanocyclopropyl)-3-(2-difluoromethoxyphenyl-methanesulfonyl)-2(R)-(2,2,2-trifluoro-1(RS)-1-phenylsulfonylpyrrol-2-ylethylamino)propionamide;

N-(1-cyanocyclopropyl)-3-(2-difluoromethoxyphenyl-methanesulfonyl)-2(R)-(2,2,2-trifluoro-1(S)-4-fluorophenyl-ethylamino)propionamide;

N-(1-cyanocyclopropyl)-3-(2-trifluoromethylpyridin-6-ylmethanesulfonyl)-2(R)-(2,2,2-trifluoro-1(RS)-4-fluorophenyl-ethylamino)propionamide;

N-(1-cyanocyclopropyl)-3-cyclopropylmethanesulfonyl-2(R)-(2,2,2-trifluoro-1(RS)-1-phenyl-sulfonylpyrrol-2-yl-ethylamino)propionamide;

N-(1-cyanocyclopropyl)-3-pyrazin-2-ylmethanesulfonyl-2(R)-(2,2,2-trifluoro-1(R)-4-fluorophenyl-ethylamino)propionamide;

N-(1-cyanocyclopropyl)-3-pyrazin-2-ylmethanesulfonyl-2(R)-(2,2,2-trifluoro-1(S)-4-fluorophenyl-ethylamino)propionamide;

N-(1-cyanotetrahydropyran-4-yl)-3-(2-difluoromethoxyphenylmethanesulfonyl)-2(R)-(2,2,2-trifluoro-1(S)-4-fluorophenylethylamino)propionamide;

N-(1-cyano1,1-dioxohexahydro-1$\lambda^6$-thiopyran-4-yl)-3-(2-difluoromethoxyphenyl-methanesulfonyl)-2(R)-(2,2,2-trifluoro-1(S)-4-fluorophenylethylamino)propionamide;

N-(1-cyanocyclopropyl)-3-(2-trifluoromethylpyridin-6-ylmethanesulfonyl)-2(R)-(2,2,2-trifluoro-1(S)-4-fluorophenyl-ethylamino)propionamide;

N-(1-cyanocyclopropyl)-3-pyrazin-2-ylmethanesulfanyl-2(R)-(2,2,2-trifluoro-1(R)-4-fluorophenyl-ethylamino)propionamide;

N-(1-cyanocyclopropyl)-3-pyrazin-2-ylmethanesulfanyl-2(R)-(2,2,2-trifluoro-1(S)-4-fluorophenyl-ethylamino)propionamide;

N-(1-cyanocyclopropyl)-3-(1-oxopyridin-2-ylmethanesulfonyl)-2(R)-(2,2,2-trifluoro-1(S)-4-fluorophenyl-ethylamino)propionamide; and N-(1-cyanocyclopropyl)-3-(pyridin-2-ylmethanesulfonyl)-2-(2,2,2-trifluoro-1-phenyl-1-trifluoromethylethylamino)-propionamide; or a pharmaceutically acceptable salt thereof.

19. The compound of claim 18 wherein:

N-(1-cyanocyclopropyl)-3-cyclopropylmethanesulfonyl-2(R)-(2,2,2-trifluoro-1(S)-phenyl-ethylamino)propionamide;

N-(1-cyanocyclopropyl)-3-cyclopropylmethanesulfonyl-2(R)-(2,2,2-trifluoro-1(S)-4-fluorophenyl-ethylamino)propionamide;

N-(1-cyanocyclopropyl)-3-pyridin-2-ylmethanesulfonyl-2(R)-(2,2,2-trifluoro-1(S)-phenylethyl-amino)propionamide;

N-(1-cyanocyclopropyl)-3-pyridin-2-ylmethanesulfonyl-2(R)-(2,2,2-trifluoro-1(S)-4-fluorophenyl-ethylamino)propionamide;

N-(1-cyanocyclopropyl)-3-cyclopropylmethanesulfonyl-2(R)-(2,2,2-trifluoro-1(S)-3,4-difluoro-phenylethylamino)propionamide;

N-(1-cyanocyclopropyl)-3-(4-fluorophenylmethanesulfonyl)-2(R)-(2,2,2-trifluoro-1(S)-4-fluoro-phenylethylamino)propionamide;

N-(1-cyanocyclopropyl)-3-(2-difluoromethoxyphenyl-methanesulfonyl)-2(R)-(2,2,2-trifluoro-1(S)-4-fluorophenylethylamino)propionamide;

N-(1-cyanocyclopropyl)-3-pyrazin-2-ylmethanesulfonyl-2(R)-(2,2,2-trifluoro-1(R)-4-fluoro-phenylethylamino)propionamide; and N-(1-cyanocyclopropyl)-3-pyrazin-2-ylmethanesulfonyl-2(R)-(2,2,2-trifluoro-1(S)-4-fluoro-phenylethylamino)propionamide; and N-(1-cyanocyclopropyl)-3-(2-trifluoromethylpyridin-6-ylmethanesulfonyl)-2(R)-(2,2,2-trifluoro-1(S)-4-fluorophenyl-ethylamino)propionamide; or a pharmaceutically acceptable salt thereof.

20. A pharmaceutical composition comprising a compound of claim 1 in admixture with one or more suitable excipients.

21. A pharmaceutical composition comprising a compound of claim 18 in admixture with one or more suitable excipients.

22. A pharmaceutical composition comprising a compound of claim 19 in admixture with one or more suitable excipients.

23. A compound of claim 19, wherein the compound is N-(1-cyanocyclopropyl)-3-cyclopropylmethanesulfonyl-2(R)-(2,2,2-trifluoro-1(S)-4-fluorophenyl-ethylamino)propionamide or a pharmaceutically acceptable salt thereof.

* * * * *